US012698495B2

(12) United States Patent  
Buller et al.

(10) Patent No.: US 12,698,495 B2  
(45) Date of Patent: Aug. 4, 2026

(54) ENGINEERED TRYPTOPHAN DECARBOXYLASES AND USES THEREOF FOR SYNTHESIZING TRYPTAMINE ANALOGS

(71) Applicant: Wisconsin Alumni Research Foundation, Madison, WI (US)

(72) Inventors: Andrew Buller, Madison, WI (US); Allwin McDonald, Jena (DE)

(73) Assignee: Wisconsin Alumni Research Foundation, Madison, WI (US)

( * ) Notice: Subject to any disclaimer, the term of this patent is extended or adjusted under 35 U.S.C. 154(b) by 456 days.

(21) Appl. No.: 18/311,698

(22) Filed: May 3, 2023

(65) Prior Publication Data

US 2023/0357744 A1 Nov. 9, 2023

Related U.S. Application Data

(60) Provisional application No. 63/337,851, filed on May 3, 2022.

(51) Int. Cl.
*C12N 9/88* (2006.01)
*C12P 13/00* (2006.01)

(52) U.S. Cl.
CPC .............. *C12N 9/88* (2013.01); *C12P 13/001* (2013.01); *C12Y 401/01028* (2013.01)

(58) Field of Classification Search
None
See application file for complete search history.

(56) References Cited

U.S. PATENT DOCUMENTS

| | | | |
|---|---|---|---|
| 5,525,491 | A | 6/1996 | Oppermann |
| 6,274,331 | B1 | 8/2001 | Looker |
| 6,479,626 | B1 | 11/2002 | Kim |
| 8,143,285 | B2 | 3/2012 | Kugimiya |
| 10,526,379 | B2 | 1/2020 | Howarth |
| 10,752,965 | B2 | 8/2020 | Chen |
| 11,123,438 | B2 | 9/2021 | Li |

OTHER PUBLICATIONS

Kalb et al., Active-Site Engineering Expands the Substrate Profile of the Basidiomycete I-Tryptophan Decarboxylase CsTDC, ChemBioChem 17, 2016, 132-36. (Year: 2016).*
Uniprot, Accession No. A7B1V0, 2020, www.uniprot.org. (Year: 2020).*
Guo et al., Protein tolerance to random amino acid change, Proc. Natl. Acad. Sci. USA 101, 2004, 9205-10. (Year: 2004).*
McDonald et al., Facile in vitro biocatalytic production of diverse tryptamines, ChemBioChem 20, 2019, 1939-44. (Year: 2019).*
Kalb et al., Active-site engineering expands the substrate profile of the basidiomycete L-tryptophan decarboxylase CsTDC, ChemBioChem 17, 2016, 132-36. (Year: 2016).*

Rassati et al., Highly Efficient One-Pot Bi-Enzymatic Cascade to 5-MeOTryptamine, ACS Catal. 15, 2015, 21115-23. (Year: 2015).*
McDonald et al., Substrate multiplexed protein engineering facilitates promiscuous biocatalytic synthesis, Nature Comm. 13, Sep. 2022, 5242. (Year: 2022).*
Altschul et al., Gapped BLAST and PSI-BLAST: a new generation of protein database search programs, Nucleic Acids Res. 25:3389-3402, 1997.
Amin, N. et al. Construction of stabilized proteins by combinatorial consensus mutagenesis. Protein Eng. Des. Sel. 17, 787-793 (2004).
Andorfer, M. C., Park, H. J., Vergara-Coll, J. & Lewis, J. C. Directed evolution of RebH for catalyst-controlled halogenation of indole C—H bonds. Chem. Sci. 7, 3720-3729 (2016).
Andorfer, M. C. et al. Understanding Flavin-Dependent Halogenase Reactivity via Substrate Activity Profiling. ACS Catal. 7, 1897-1904 (2017).
Bloom, J. D., Labthavikul, S. T., Otey, C. R. & Arnold, F. H. Protein stability promotes evolvability. Proc. Natl. Acad. Sci. U. S. A. 103, 5869-5874 (2006).
Buller, A. R. et al. Directed evolution of the tryptophan synthase β-subunit for stand-alone function recapitulates allosteric activation. Proc. Natl. Acad. Sci. 112, 14599-14604 (2015).
Buller, A. R., Van Roye, P., Murciano-Calles, J. & Arnold, F. H. Tryptophan Synthase Uses an Atypical Mechanism to Achieve Substrate Specificity. Biochemistry 55, 7043-7046 (2016).
Buller, A. R. et al. Directed evolution mimics allosteric activation by stepwise tuning of the conformational ensemble. J. Am. Chem. Soc. 140, 7256-7266 (2018).
Cornish-Bowden, A. Enzyme Specificity : Its Meaning in the General Case. J. theor. Biol. 108, 451-457 (1984).
Desai, B. J. & Gonzalez, R. L. Multiplexed genomic encoding of non-canonical amino acids for labeling large complexes. Nat. Chem. Biol. 16, 1129-1135 (2020).
Devereux, R. B., Lutas, E. M., Casale, P. N., Kligfield, P., Eisenberg, R. R., Hammond, I. W., . . . & Laragh, J. H. (1984). Standardization of M-mode echocardiographic left ventricular anatomic measurements. Journal of the American College of Cardiology, 4(6), 1222-1230.
Diefenbach, X. W. et al. Enabling Biocatalysis by High-Throughput Protein Engineering Using Droplet Microfluidics Coupled to Mass Spectrometry. ACS Omega 3, 1498-1508 (2018).
Ferrari et al., Genetics, in Hardwood et al., (eds.), Bacillus, Plenum Publishing Corp., pp. 57-72, 1989.
Fersht, A. Structure and Mechanism in Protein Science: A Guide to Enzyme Catalysis and Protein Folding. (W. H. Freeman and Company, 1999).
Fox, R. J. et al. Improving catalytic function by ProSAR-driven enzyme evolution. Nat. Biotechnol. 25, 338-344 (2007).
Fricke, J., Blei, F. & Hoffmeister, D. Enzymatic Synthesis of Psilocybin. Angew. Chemie—Int. Ed. 56, 12352-12355 (2017).

(Continued)

*Primary Examiner* — Todd M Epstein
(74) *Attorney, Agent, or Firm* — Daniel A. Blasiole; DeWitt LLP

(57) ABSTRACT

Unnatural, mutant tryptophan decarboxylase proteins and methods of using same. The mutants have an amino acid sequence at least 80% identical to SEQ ID NO:1 and have substitutions at one or more of amino acid positions 98, 99, 120, 126, 339, 349, and 355 of SEQ ID NO:1. The mutants can have enhanced activity and/or substrate promiscuity and be used for synthesizing tryptamine analogs.

21 Claims, 21 Drawing Sheets

Specification includes a Sequence Listing.

(56) References Cited

OTHER PUBLICATIONS

Glennon, R. A. Higher-End Serotonin Receptors: 5-HT5, 5-HT6, and 5-HT7. J. Med. Chem. 46, 2795-2812 (2003).

Goddard, J., Reymond, J. & Uni, V. Enzyme Activity Fingerprinting with Substrate Cocktails. JACS Commun. 11116-11117 (2004).

Goodwin, N. C., Morrison, J. P., Fuerst, D. E. & Hadi, T. Biocatalysis in Medicinal Chemistry: Challenges to Access and Drivers for Adoption. ACS Med. Chem. Lett. 10, 1363-1366 (2019).

Heilmann, H. D. On the mechanism of action of *Escherichia coli* tryptophan synthase Steady-state investigations. BBA—Enzymol. (1978) doi:10.1016/0005-2744(78)90092-X.

Herger, M. et al. Synthesis of β-Branched Tryptophan Analogues Using an Engineered Subunit of Tryptophan Synthase. J. Am. Chem. Soc. 138, 8388-8391 (2016).

Huffman, M. A. et al. Design of an in vitro biocatalytic cascade for the manufacture of islatravir. Science (80-. ). 366, 1255-1259 (2019).

Joiner, C. M., Levine, Z. G., Aonbangkhen, C., Woo, C. M. & Walker, S. Aspartate Residues Far from the Active Site Drive O-GlcNAc Transferase Substrate Selection. J. Am. Chem. Soc. 141, 12974-12978 (2019).

Jotun-Hein, Muscle et al., MUSCLE: a multiple sequence alignment method with reduced time and space complexity, BMC Bioinformatics 5: 113, 2004.

Kim, H. et al. A multi-substrate screening approach for the identification of a broadly applicable Diels—Alder catalyst. Nat. Commun. 1-6 (2019) doi:10.1038/s41467-019-08374-z.

Knorrscheidt, A. et al. Simultaneous screening of multiple substrates with an unspecific peroxygenase enabled modified alkane and alkene oxyfunctionalisations. Catal. Sci. Technol. 6058-6064 (2021) doi:10.1039/d0cy02457k.

Kuo, Y. M., Henry, R. A. & Andrews, A. J. Measuring specificity in multi-substrate/product systems as a tool to investigate selectivity in vivo. Biochim. Biophys. Acta—Proteins Proteomics 1864, 70-76 (2016).

Larkin M. A., et al., CLUSTALW2, ClustalW and ClustalX version 2, Bioinformatics 23(21): 2947-2948, 2007.

Matthews, B. W. Structural and genetic analysis of protein stability. Annual Review of Biochemistry vol. 62 139-160 (1993).

McDonald, A. D., Perkins, L. J. & Buller, A. R. Facile in Vitro Biocatalytic Production of Diverse Tryptamines. ChemBioChem 20, 1939-1944 (2019).

McLaren, D. G. et al. High-Throughput Mass Spectrometry for Hit Identification: Current Landscape and Future Perspectives. SLAS Discov. 26, 168-191 (2021).

Needleman and Wunsch, A General Method Applicable to the Search for Similarities in the Amino Acid Sequence of Two Proteins, J. Mol. Biol., 48:443-453, 1970.

Notredame et al., T-Coffee: A novel method for multiple sequence alignments, Journal of Molecular Biology 302: 205-217, 2000.

Obexer, R. et al. Emergence of a catalytic tetrad during evolution of a highly active artificial aldolase. (2016) Nature chemistry, Jan. 2017, vol. 9 (1), p. 50-56 doi:10.1038/NCHEM.2596.

Pearson and Lipman, Improved tools for biological sequence comparison, Proc. Natl. Acad. Sci. USA 85:2444-2448, 1988.

Reetz, M. T., Bocola, M., Carballeira, J. D., Zha, D. & Vogel, A. Expanding the range of substrate acceptance of enzymes: Combinatorial active-site saturation test. Angew. Chemie—Int. Ed. 44, 4192-4196 (2005).

Reetz, M. T. What are the Limitations of Enzymes in Synthetic Organic Chemistry ? Chem. Rec. 16, 2449-2459 (2016).

Romney, D. K., Murciano-Calles, J., Wehrmüller, J. E. & Arnold, F. H. Unlocking Reactivity of TrpB: A General Biocatalytic Platform for Synthesis of Tryptophan Analogues. J. Am. Chem. Soc. 139, 10769-10776 (2017).

Romney, D. K., Sarai, N. S. & Arnold, F. H. Nitroalkanes as Versatile Nucleophiles for Enzymatic Synthesis of Noncanonical Amino Acids. ACS Catal. 9, acscatal.9b02089 (2019).

Sandström, A. G., Wikmark, Y., Engström, K., Nyhlén, J. & Bäckvall, J. E. Combinatorial reshaping of the Candida antarctica lipase A substrate pocket for enantioselectivity using an extremely condensed library. PNAS 109, 78-83 (2012).

Savile, C. K. et al. Biocatalytic Asymmetric Synthesis of Chiral Amines from Ketones Applied to Sitagliptin Manufacture. Science (80-. ). 329, 305-310 (2010).

Schrittwieser, J. H., Velikogne, S., Hall, M. & Kroutil, W. Artificial Biocatalytic Linear Cascades for Preparation of Organic Molecules. Chemical Reviews vol. 118 270-348 (2018).

Smith and Waterman, Comparison of Biosequences, Adv. Appl. Math., 2:482-489, 1981.

Stanisic, A., Husken, A. & Kries, H. HAMA: a multiplexed LC-MS/MS assay for specificity profiling of adenylate-forming enzymes. Chem. Sci. 10, 10395-10399 (2019).

Staudt, S. et al. Direct Oxidation of Cycloalkanes to Cycloalkanones with Oxygen in Water. Angew. Chemie 52, 2359-2363 (2013).

Sattler, J. H. et al. Redox Self-Sufficient Biocatalyst Network for the Amination of Primary Alcohols. Angew. Chemie 51, 9156-9159 (2012).

Thompson J. D., Higgins D. G., Gibson T. J., CLUSTAL W: improving the sensitivity of progressive multiple sequence alignment through sequence weighting, position-specific gap penalties and weight matrix choice, Nucleic Acids Research 22: 4673-4680, 1994.

Truppo, M. D. Biocatalysis in the Pharmaceutical Industry: The Need for Speed. ACS Med. Chem. Lett. 8, 476-480 (2017).

Wang, L., Xie, J. & Schultz, P. G. Expanding the genetic code. Annu. Rev. Biophys. Biomol. Struct. 35, 225-249 (2006).

Watkins-Dulaney, E., Straathof, S. & Arnold, F. Tryptophan Synthase: Biocatalyst Extraordinaire. ChemBioChem vol. 22 5-16 (2021).

Weeks, A. M. & Wells, J. A. Engineering peptide ligase specificity by proteomic identification of ligation sites. Nat. Chem. Biol. 14, 50-57 (2018).

Williams, B. B. et al. Discovery and characterization of gut microbiota decarboxylases that can produce the neurotransmitter tryptamine. Cell Host Microbe 16, 495-503 (2014).

Wrenbeck, E. E., Azouz, L. R. & Whitehead, T. A. Single-mutation fitness landscapes for an enzyme on multiple substrates reveal specificity is globally encoded. Nat. Commun. 8, 1-10 (2017).

Ye, L., Yang, C. & Yu, H. From molecular engineering to process engineering: development of high-throughput screening methods in enzyme directed evolution. Appl. Microbiol. Biotechnol. 2017 1022 102, 559-567 (2017).

* cited by examiner

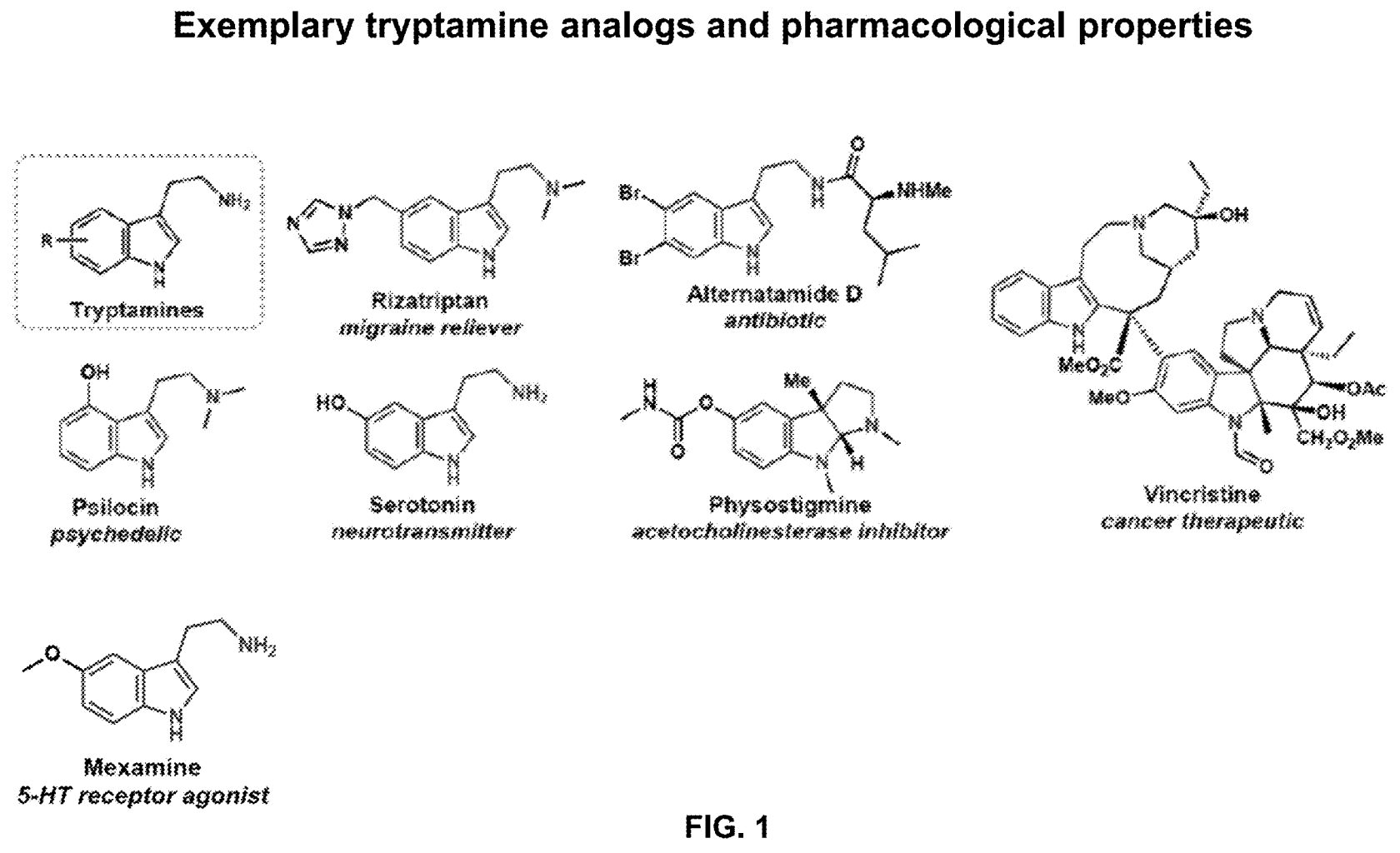

Exemplary tryptamine analogs and pharmacological properties

Vincristine
*cancer therapeutic*

Alternamide D
*antibiotic*

Physostigmine
*acetocholinesterase inhibitor*

Rizatriptan
*migraine reliever*

Serotonin
*neurotransmitter*

Tryptamines

Psilocin
*psychedelic*

Mexamine
*5-HT receptor agonist*

FIG. 1

*Ruminococcus gnavus tryptophan decarboxylase (RgnTDC) reaction*

FIG. 2

Synthetic cascade for tryptamine synthesis

FIG. 3

*Rgn*TDC active site model

Variant activity on single substrates

Kinetic characterization of improved variants

| Substrate | Variant | $k_{cat}$ $(s^{-1})$ | $K_M$ (mM) | $k_{cat}/K_M$ $(M^{-1} s^{-1})$ |
|---|---|---|---|---|
| | wt | 11 | 1.6 | 6900 |
| Trp | F98V | 8.7 | 2.8 | 3100 |
| | W349K | 1.0 | 1.4 | 700 |
| | L355M | 3.3 | 0.54 | 6200 |
| 4-Br-Trp | wt | 0.37 | 3.4 | 110 |
| | L355M | 1.1 | 0.7 | 1600 |
| 5-OMe-Trp | wt | 0.017 | 0.99 | 17 |
| | W349K | 0.25 | 1.1 | 240 |
| 6-Cl-Trp | wt | 0.52 | 0.14 | 3700 |
| | F98V | 0.91 | 0.60 | 1500 |

*Pyrococcus furiosus* tryptophan synthase (*Pf*TrpB)

FIG. 13

Biocatalytic cascade set-up

FIG. 14A

Synthesized cascade products

SEQUENCE LISTING

```
Sequence total quantity: 4
SEQ ID NO: 1              moltype = AA  length = 490
FEATURE                  Location/Qualifiers
source                   1..490
                         mol_type = protein
                         organism = Ruminococcus gnavus
SEQUENCE: 1
MSQVIKKKRN TFMIGTEYIL NSTQLEEAIK SFVHDFCAEK HEIHDQPVVV EAKEHQEDKI  60
KQIKIPEKGR PVNEVVSEMM NEVYRYRGDA NHPRFFSFVP GPASSVSWLG DIMTSAYNIH  120
AGGSKLAPMV NCIEQEVLKW LAKQVGFTEN PGGVFVSGGS MANITALTAA RDNKLTDINL  180
HLGTAYISDQ THSSVAKGLR IIGITDSRIR RIPTNSHFQM DTTKLEEAIE TDKKSGYIPF  240
VVIGTAGTTN TGSIDPLTEI SALCKKHDMW FHIDGAYGAS VLLSPKYKSL LTGTGLADSI  300
SWDAHKWLFQ TYGCAMVLVK DIRNLFHSFH VNPEYLKDLE NDIDNVNTWD IGMELTRPAR  360
GLKLWLTLQV LGSDLIGSAI EHGFQLAVWA EEALNPKKDW EIVSPAQMAM INFRYAPKDL  420
TKEEQDILNE KISHRILESG YAAIFTTVLN GKTVLRICAI HPEATQEDMQ HTIDLLDQYG  480
REIYTEMKKA                                                          490

SEQ ID NO: 2              moltype = DNA  length = 1473
FEATURE                  Location/Qualifiers
source                   1..1473
                         mol_type = genomic DNA
                         organism = Ruminococcus gnavus
SEQUENCE: 2
atgagtcaag taattaagaa aaagaggaat acctttatga tcggaaccga atatatttta  60
aacagtaccc agttggaaga ggccatcaaa tcatttgtgc atgatttttg tgcagaaaatc  120
cacgagatcc acgatcagcc tgttgttgtt gaagcaaagg aacatcagga ggacaaaatc  180
aaacagatca aaatcccgga aaaaggacgc ccggtaaacg aagttgtctc tgaaatgatg  240
aacgaagtgt accgctaccg cggagatgcc aaccatccac gttttttcag cttcgttccg  300
ggaccggctt cttcggtttc ctggctggga gatatcatga catctgctta caacattcat  360
gccggcggaa gcaaacttgc ccccatggtc aactgtattg aacaggaagt gttaaaatgg  420
ctggcaaaac aggtcggatt taccgagaat cccggaggtg tctttgtaag cggagggtct  480
atggcaaaca tcaccgctct gactgccgcc cgggacaata agctaacaga tatcaatctc  540
catctgggaa cagcttatat ttcggatcag acacacagct ccgtcgcaaa aggactgcgc  600
atcatcggaa tcacggacag ccggatccgc agaattccga caaactccca tttccagatg  660
gatacgacaa aactggaaga agccattgaa acagacaaaa aatccggcta tatcccgttt  720
gttgtcattg gtaccgcggg aaccacgaac accggaagta tagatccact tacagagatt  780
tccgcacttt gtaaaaaaca tgatatgtgg tttcacattg acggggctta cggtgcttct  840
gtactgttaa gcccgaaata caagtctctg ttaactggaa ccgggcttgc tgacagtatc  900
agctgggatg cacacaaatg gctcttccag acgtacggat gtgctatggt tcttgtaaaa  960
gatatccgta acctgttcca cagcttccat gtaaatccag agtatttaaa agatctggaa  1020
aatgacatcg acaatgtcaa tacatgggat atcggaatgg agctgacccg ccctgcccgc  1080
ggcttaaaac tatggctgac tctgcaggtg ctcggaagtg atctgatcgg atctgccatt  1140
gagcatggat tccagctggc agtctgggcc gaagaagctc tgaatccaaa aaaagactgg  1200
gagatcgtct cccctgcaca gatggcaatg atcaacttcc gctatgcccc aaaagatctg  1260
acaaaggaag aacaggacat tttgaatgaa aagatctccc atcggatcct cgaaagcggt  1320
tatgcagcga tatttactac tgttctcaat ggaaagaccg tacttcgaat ctgcgcgatc  1380
catccggaag caacacagga agatatgcag catacgatcg atctgttgga tcagtatggt  1440
cgtgaaattt atacggaaat gaaaaaagct taa                               1473

SEQ ID NO: 3              moltype = AA  length = 396
FEATURE                  Location/Qualifiers
source                   1..396
                         mol_type = protein
                         organism = Pyrococcus furiosus
SEQUENCE: 3
MWFGEFGGQY VPETLVGPLK ELEKAYKRFK DDEEFNRQLN YYLKTWAGRP TPLYYAKRLT  60
EKIGGAKVYL KREDLVHGGA HKTNNAIGQA LLAKLMGKTR LIAETGAGQH GVATAMAGAL  120
LGMKVDIYMG AEDVERQKMN VFRMKLLGAN VIPVNSGSRT LKDAINEALR DWVATFEYTH  180
YLIGSVVGPH PYPTIVRDFQ SVIGREAKAQ ILEAEGQLPD VIVACVGGGS NAMGIFYPFV  240
NDKKVKLVGV EAGGKGLESG KHSASLNAGQ VGVSHGMLSY FLQDEEGQIK PSHSIAPGLD  300
YPGVGPEHAY LKKIQRAEYV AVTDEEALKA FHELSRTEGI IPALESAHAV AYAMKLAKEM  360
```

-continued

```
SRDEIIIVNL SGRGDKDLDI VLKASGNVLE HHHHHH                        396

SEQ ID NO: 4          moltype = DNA  length = 1191
FEATURE               Location/Qualifiers
source                1..1191
                      mol_type = genomic DNA
                      organism = Pyrococcus furiosus
SEQUENCE: 4
atgtggttcg gtgaatttgg tggtcagtac gtgccagaaa cgctggttgg acccctgaaa   60
gagctggaaa aagcttacaa acgtttcaaa gatgacgaag aattcaatcg tcagctgaat  120
tactacctga aaacctgggc aggtcgtcca accccactgt actacgcaaa acgcctgact  180
gaaaaaatcg gtggtgctaa agtctacctg aaacgtgaag acctggttca cggtggtgca  240
cacaagacca acaacgccat cggtcaggca ctgctggcaa agctcatggg taaaactcgt  300
ctgatcgctg agaccggtgc tggtcagcac ggcgtagcga ctgcaatggc tggtgcactg  360
ctgggcatga aagtggacat ttacatgggt gctgaggacg tagaacgtca gaaaatgaac  420
gtattccgta tgaagctgct gggtgcaaac gtaattccag ttaactccgg ttctcgcacc  480
ctgaaagacg caatcaacga ggctctgcgt gattgggtgg ctacttttga atacacccac  540
tacctaatcg gttccgtggt cggtccacat ccgtatccga ccatcgttcg tgattttcag  600
tctgttatcg gtcgtgaggc taaagcgcag atcctggagg ctgaaggtca gctgccagat  660
gtaatcgttg cttgtgttgg tggtggctct aacgcgatgg gtatctttta cccgttcgtg  720
aacgacaaaa aagttaagct ggttggcgtt gaggctggtg gtaaaggcct ggaatctggt  780
aagcattccg ctagcctgaa cgcaggtcag gttggtgtgt cccatggcat gctgtcctac  840
tttctgcagg acgaagaagg tcagatcaaa ccaagccact ccatcgcacc aggtctggat  900
tatccaggtg ttggtccaga acacgcttac ctgaaaaaaa ttcagcgtgc tgaatacgtg  960
gctgtaaccg atgaagaagc actgaaagcg ttccatgaac tgagccgtac cgaaggtatc 1020
atcccagctc tggaatctgc gcatgctgtg gcttacgcta tgaaactggc taaggaaatg 1080
tctcgtgatg agatcatcat cgtaaacctg tctggtcgtg gtgacaaaga cctggatatt 1140
gtcctgaaag cgtctggcaa cgtgctcgag caccaccacc accaccactg a          1191
```

ENGINEERED TRYPTOPHAN DECARBOXYLASES AND USES THEREOF FOR SYNTHESIZING TRYPTAMINE ANALOGS

CROSS-REFERENCE TO RELATED APPLICATIONS

This application claims priority to U.S. Provisional Application No. 63/337,851, filed May 3, 2022, which is incorporated herein by reference in its entirety.

STATEMENT REGARDING FEDERALLY SPONSORED RESEARCH

This invention was made with government support under GM137417 awarded by the National Institutes of Health. The government has certain rights in the invention.

SEQUENCE LISTING

The instant application contains a Sequence Listing which has been electronically submitted in XML format and is hereby incorporated by reference in its entirety. The XML copy was created on Mar. 22, 2023, is named Seq_List— P220120US02.xml and is 8,086 bytes in size.

FIELD OF THE INVENTION

The invention is directed to engineered tryptophan decarboxylases with enhanced activity and/or substrate promiscuity and uses thereof for synthesizing tryptamine analogs.

BACKGROUND

Tryptamine analogs, including substituted tryptamines, have diverse mechanisms of biological activity and have been shown to act as neurotransmitters, anti-depressants, and anti-migraine drugs (FIG. 1). Hence, testing the biological activity of new tryptamines is dependent upon being able to produce a varied set of tryptamine analogs. Current methodologies to produce tryptamines require multiple steps and harsh reaction conditions and are often inefficient for the production of desirable, tryptamine analogs.

Previous chemoenzymatic routes have relied on using eukaryotic aromatic amino acid decarboxylase (AADC, EC 4.1.1.28) enzymes to effect the decarboxylation of substituted tryptophans. However, the AADCs generally have low activity with substituted tryptophans. The *Ruminococcus gnavus* tryptophan decarboxylase (RgnTDC, EC 4.1.1.105) is a specialist for tryptophan over other aromatic amino acids. This enzyme has high promiscuous activity with some substituted tryptophans, but struggles with the pharmacologically-prominent 4- and 5-substituted tryptophans and has no activity with β-branched tryptophans. Hence, mutations that increase decarboxylase activity with substituted tryptophans and other tryptophan analogs would facilitate efficient biocatalytic production of tryptamine analogs.

SUMMARY OF THE INVENTION

One aspect of the invention is directed to mutant tryptophan decarboxylase proteins. In some versions, the mutant tryptophan decarboxylase protein comprises an amino acid sequence at least 90% identical to SEQ ID NO:1.

In some versions, the amino acid sequence of the mutant tryptophan decarboxylase protein comprises one or more of:

a residue other than phenylalanine at a position corresponding to position 98 of SEQ ID NO:1; a residue other than valine at a position corresponding to position 99 of SEQ ID NO:1; a residue other than histidine at a position corresponding to position 120 of SEQ ID NO:1; a residue other than leucine at a position corresponding to position 126 of SEQ ID NO:1; a residue other than leucine at a position corresponding to position 339 of SEQ ID NO:1; a residue other than tryptophan at a position corresponding to position 349 of SEQ ID NO:1; and a residue other than leucine at a position corresponding to position 355 of SEQ ID NO:1.

In some versions, the amino acid sequence of the mutant tryptophan decarboxylase protein comprises one or more of: methionine or valine at a position corresponding to position 98 of SEQ ID NO:1; alanine at a position corresponding to position 99 of SEQ ID NO:1; valine at a position corresponding to position 339 of SEQ ID NO:1; lysine, phenylalanine, serine, or tryptophan at a position corresponding to position 349 of SEQ ID NO:1; and alanine or methionine at a position corresponding to position 355 of SEQ ID NO:1.

In some versions, the mutant tryptophan decarboxylase protein exhibits an increased activity with respect to a protein comprising an amino acid sequence 100% identical to SEQ ID NO: 1. In some versions, the increased activity comprises increased activity in decarboxylating a substituted tryptophan substrate. In some versions, the increased activity comprises increased activity in decarboxylating a substituted tryptophan substrate comprising a substituent at any one or more of a 2 position, a 4 position, a 5 position, a 6 position, or a 7 position on the substituted tryptophan. In some versions, the increased activity comprises increased activity in decarboxylating a first substrate relative to a second substrate, wherein the first substrate is not the second substrate, wherein the first substrate is selected from the group consisting of any one or more of 2-substituted tryptophan, 4-substituted tryptophan, 5-substituted tryptophan, 6-substituted tryptophan, and 7-substituted tryptophan, and wherein the second substrate is selected from the group consisting of any one or more of unsubstituted tryptophan, 2-substituted tryptophan, 4-substituted tryptophan, 5-substituted tryptophan, 6-substituted tryptophan, and 7-substituted tryptophan. In some versions, the increased activity comprises increased combined activity in decarboxylating any two or more different substrates, wherein the two more different substrates are selected from the group consisting of unsubstituted tryptophan, one or more 2-substituted tryptophans, one or more 4-substituted tryptophans, one or more 5-substituted tryptophans, one or more 6-substituted tryptophans, and one or more 7-substituted tryptophans.

Another aspect of the invention is directed to methods of generating a product. In some versions, the method comprises contacting a substrate with a mutant tryptophan decarboxylase protein of the invention to thereby generate the product. In some versions, the substrate comprises a tryptophan analog. In some versions, the substrate comprises one or more of tryptophan and substituted tryptophan. In some versions, the product comprises one or more of tryptamine or substituted tryptamine. In some versions, the substrate comprises substituted tryptophan, and the product comprises substituted tryptamine.

In some versions, the methods further comprise generating the substrate. In some versions, generating the substrate comprises contacting an upstream substrate with a tryptophan synthase to thereby generate the substrate. In some versions, the upstream substrate comprises an indole analog. In some versions, the upstream substrate comprises one or more of indole or substituted indole. In some versions, the upstream substrate comprises substituted indole, and the substrate comprises substituted tryptophan.

BRIEF DESCRIPTION OF THE DRAWINGS

FIG. 1. Exemplary tryptamine analogs and their pharmacological properties. The tryptamine motif is highlighted.

FIG. 2. *Ruminococcus gnavus* tryptophan decarboxylase (RgnTDC) reaction. The labile bond and carbon numbers are highlighted.

FIG. 3. Exemplary two-step cascade to generate substituted tryptamines from indole precursors.

FIG. 11A. Library data for F98 (no proline or serine mutations were sequenced from this library). The most abundant product is 6-Cl—. FIG. 11B. Library data for V99X. The most abundant product is 6-Cl—. FIG. 11C. Library data for H120X (no alanine or phenylalanine mutations were sequenced from this library). The most abundant products are 6-Cl— and 7-I—. FIG. 11D. Library data for L339 (no tryptophan mutations were sequenced from this library). The most abundant product is 6-Cl—. FIG. 11E. Library data for W349. The most abundant product is 6-Cl—. FIG. 11F. Library data for L355 (no proline mutations were sequenced from this library). The most abundant products are 6-Cl— (L, M), 7-I— (V, C, T, I, Q, E, S, H, N), 4-Br— (A, F, Y), and 2-Me- (G, K, D, W, R).

FIG. 12A. Select improved variants from active-site libraries. Screening conditions use a mixture of 0.2 mM Trp and 7-I-Trp, and 2 mM 2-Me-Trp, 4-Br-Trp, 5-OMe-Trp, and 6-Cl-Trp. Stacked bars indicate relative abundances of each product (from top to bottom: tryptamine, 2-Me-, 4-Br—, 5-OMe-, 6-Cl—, and 7-I—), and black diamonds indicate the total product formed. The most abundant products are 6-Cl— (wt, F98V, W349K, and L355M) and 4-Br— (L355A). FIG. 12B. Turnover numbers of wild-type RgnTDC and the top improved variant for each substrate. Different variants are depicted by different bars: wt TDC (left) and F98V (right) for 2-Me-; wt TDC (left) and L355M (right) for 4-Br—; wt TDC (left) and W349K (right) for 5-OMe-; wt TDC (left) and W349K (right) for 5-OEt-; wt TDC (left) and F98V (right) for 6-Cl—; and wt TDC (left) and F98V (right) for 6-$NO_2$—. FIG. 12C. Michaelis-Menten parameters for wild-type RgnTDC and activated variants for Trp analogs as well as with Trp.

FIG. 13. General reaction scheme for PfTrpB. The carbon numbers are highlighted.

FIGS. 14A-14B. Engineered biocatalytic cascade for synthesis of tryptamine analogs. FIG. 14A. Utilized biocatalytic cascade for the telescoped biosynthesis of tryptamine analogs. FIG. 14B. Synthesized tryptamines, with the RgnTDC variants used for different syntheses highlighted. *1.4 mmol substrate used for 6-chlorotryptamine synthesis.

DETAILED DESCRIPTION OF THE INVENTION

Figure 4:
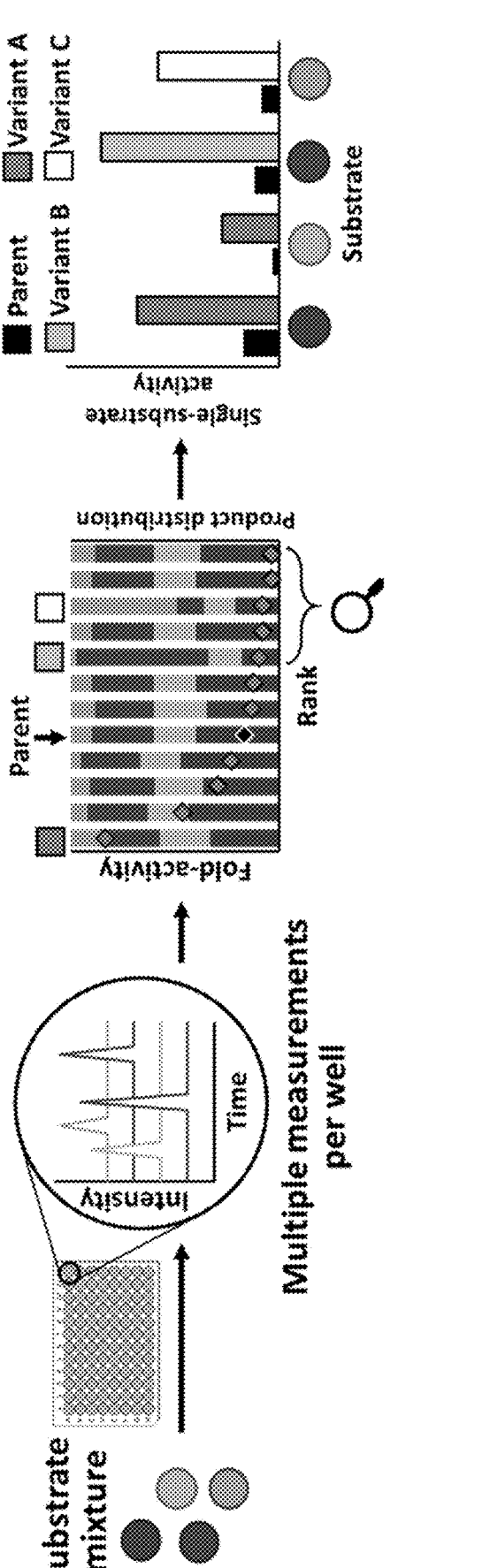
FIG. 4. Engineering for a promiscuous biocatalytic cascade using substrate multiplexed screening (SUMS). SUMS generally mimics a traditional library screening workflow, but the inclusion of multiple substrates leads to richer data on each screened variant. Single-substrate activity, total product formed, and changes in product distribution can all be leveraged to identify variants for further investigation through single-substrate activity validation.

One aspect of the invention is directed to mutant tryptophan decarboxylase proteins. The mutant tryptophan decarboxylase proteins comprise an amino acid sequence with at least one mutation with respect to a native amino acid sequence. "Native amino acid sequence" refers to the full amino acid sequence, or any contiguous portion thereof, of any protein found in nature.

An exemplary tryptophan decarboxylase protein with a native amino acid sequence is the *Ruminococcus gnavus* tryptophan decarboxylase (RgnTDC, EC 4.1.1.105) protein, which has the amino acid sequence of SEQ ID NO:1:

(SEQ ID NO: 1)
MSQVIKKKRNTFMIGTEYILNSTQLEEAIKSFVHDFCAEKHEIHDQPVVV

EAKEHQEDKIKQIKIPEKGRPVNEVVSEMMNEVYRYRGDANHPRFFSFVP

GPASSVSWLGDIMTSAYNIHAGGSKLAPMVNCIEQEVLKWLAKQVGFTEN

PGGVFVSGGSMANITALTAARDNKLTDINLHLGTAYISDQTHSSVAKGLR

IIGITDSRIRRIPTNSHFQMDTTKLEEAIETDKKSGYIPFVVIGTAGTTN

TGSIDPLTEISALCKKHDMWFHIDGAYGASVLLSPKYKSLLTGTGLADSI

SWDAHKWLFQTYGCAMVLVKDIRNLFHSFHVNPEYLKDLENDIDNVNTWD

IGMELTRPARGLKLWLTLQVLGSDLIGSAIEHGFQLAVWAEEALNPKKDW

EIVSPAQMAMINFRYAPKDLTKEEQDILNEKISHRILESGYAAIFTTVLN

GKTVLRICAIHPEATQEDMQHTIDLLDQYGREIYTEMKKA

An exemplary coding sequence for the tryptophan decarboxylase protein represented by SEQ ID NO:1 is SEQ ID NO:2:

(SEQ ID NO: 2)
ATGAGTCAAGTAATTAAGAAAAAGAGGAATACCTTTATGATCGGAACCGA

ATATATTTTAAACAGTACCCAGTTGGAAGAGGCCATCAAATCATTTGTGC

ATGATTTTTGTGCAGAAAAACACGAGATCCACGATCAGCCTGTTGTTGTT

GAAGCAAAGGAACATCAGGAGGACAAAATCAAACAGATCAAAATCCCGGA

AAAAGGACGCCCGGTAAACGAAGTTGTCTCTGAAATGATGAACGAAGTGT

ACCGCTACCGCGGAGATGCCAACCATCCACGTTTTTTCAGCTTCGTTCCG

GGACCGGCTTCTTCGGTTTCCTGGCTGGGAGATATCATGACATCTGCTTA

CAACATTCATGCCGGCGGAAGCAAACTTGCCCCCATGGTCAACTGTATTG

AACAGGAAGTGTTAAAATGGCTGGCAAAACAGGTCGGATTTACCGAGAAT

CCCGGAGGTGTCTTTGTAAGCGGAGGGTCTATGGCAAACATCACCGCTCT

GACTGCCGCCCGGGACAATAAGCTAACAGATATCAATCTCCATCTGGGAA

CAGCTTATATTTCGGATCAGACACACAGCTCCGTCGCAAAAGGACTGCGC

ATCATCGGAATCACGGACAGCCGGATCCGCAGAATTCCGACAAACTCCCA

TTTCCAGATGGATACGACAAAACTGGAAGAAGCCATTGAAACAGACAAAA

AATCCGGCTATATCCCGTTTGTTGTCATTGGTACCGCGGGAACCACGAAC

ACCGGAAGTATAGATCCACTTACAGAGATTTCCGCACTTTGTAAAAAACA

TGATATGTGGTTTCACATTGACGGGGCTTACGGTGCTTCTGTACTGTTAA

GCCCGAAATACAAGTCTCTGTTAACTGGAACCGGGCTTGCTGACAGTATC

AGCTGGGATGCACACAAATGGCTCTTCCAGACGTACGGATGTGCTATGGT

TCTTGTAAAAGATATCCGTAACCTGTTCCACAGCTTCCATGTAAATCCAG

AGTATTTAAAAGATCTGGAAAATGACATCGACAATGTCAATACATGGGAT

ATCGGAATGGAGCTGACCCGCCCTGCCCGCGGCTTAAAACTATGGCTGAC

TCTGCAGGTGCTCGGAAGTGATCTGATCGGATCTGCCATTGAGCATGGAT

TCCAGCTGGCAGTCTGGGCCGAAGAAGCTCTGAATCCAAAAAAAGACTGG

GAGATCGTCTCCCCTGCACAGATGGCAATGATCAACTTCCGCTATGCCCC

AAAAGATCTGACAAAGGAAGAACAGGACATTTTGAATGAAAAAGATCTCCC

ATCGGATCCTCGAAAGCGGTTATGCAGCGATATTTACTACTGTTCTCAAT

-continued

GGAAAGACCGTACTTCGAATCTGCGCGATCCATCCGGAAGCAACACAGGA

AGATATGCAGCATACGATCGATCTGTTGGATCAGTATGGTCGTGAAATTT

ATACGGAAATGAAAAAAGCTTAA

The mutant tryptophan decarboxylase proteins of the invention may comprise an amino acid sequence at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO:1.

The mutant tryptophan decarboxylase proteins of the invention may have one or more substitutions at positions corresponding to particular positions of SEQ ID NO:1. In some versions, the mutant tryptophan decarboxylase proteins comprise any one or more of: a residue other than phenylalanine at a position corresponding to position 98 of SEQ ID NO:1; a residue other than valine at a position corresponding to position 99 of SEQ ID NO:1; a residue other than histidine at a position corresponding to position 120 of SEQ ID NO:1; a residue other than leucine at a position corresponding to position 126 of SEQ ID NO:1; a residue other than leucine at a position corresponding to position 339 of SEQ ID NO:1; a residue other than tryptophan at a position corresponding to position 349 of SEQ ID NO:1; and a residue other than leucine at a position corresponding to position 355 of SEQ ID NO:1.

In some versions, the mutant tryptophan decarboxylase proteins of the invention comprise any one or more of: a residue other than phenylalanine at a position corresponding to position 98 of SEQ ID NO:1; a residue other than valine at a position corresponding to position 99 of SEQ ID NO:1; a residue other than leucine at a position corresponding to position 339 of SEQ ID NO:1; a residue other than tryptophan at a position corresponding to position 349 of SEQ ID NO:1; and a residue other than leucine at a position corresponding to position 355 of SEQ ID NO:1.

In some versions, the mutant tryptophan decarboxylase proteins of the invention comprise any one or more of: methionine or valine at a position corresponding to position 98 of SEQ ID NO:1; alanine at a position corresponding to position 99 of SEQ ID NO:1; valine at a position corresponding to position 339 of SEQ ID NO:1; lysine, phenylalanine, serine, or tryptophan at a position corresponding to position 349 of SEQ ID NO:1; and alanine or methionine at a position corresponding to position 355 of SEQ ID NO:1.

In some versions, the mutant tryptophan decarboxylase proteins of the invention comprise methionine at a position corresponding to position 98 of SEQ ID NO:1. In some versions, the mutant tryptophan decarboxylase proteins of the invention comprise valine at a position corresponding to position 98 of SEQ ID NO: 1. In some versions, the mutant tryptophan decarboxylase proteins of the invention comprise alanine at a position corresponding to position 99 of SEQ ID NO: 1. In some versions, the mutant tryptophan decarboxylase proteins of the invention comprise valine at a position corresponding to position 339 of SEQ ID NO: 1. In some versions, the mutant tryptophan decarboxylase proteins of the invention comprise lysine at a position corresponding to position 349 of SEQ ID NO:1. In some versions, the mutant tryptophan decarboxylase proteins of the invention comprise phenylalanine at a position corresponding to position 349 of SEQ ID NO: 1. In some versions, the mutant tryptophan decarboxylase proteins of the invention comprise serine at a position corresponding to position 349 of SEQ ID NO:1. In some versions, the mutant tryptophan decarboxylase proteins of the invention comprise tryptophan at a position corresponding to position 349 of SEQ ID NO: 1. In some versions, the mutant tryptophan decarboxylase proteins of the invention comprise alanine at a position corresponding to position 355 of SEQ ID NO: 1. In some versions, the mutant tryptophan decarboxylase proteins of the invention comprise methionine at a position corresponding to position 355 of SEQ ID NO:1.

The mutant tryptophan decarboxylase proteins of the invention may comprise any one or more mutations at any one or more positions corresponding to the mutations exemplified for *Ruminococcus gnavus* tryptophan decarboxylase herein. See, e.g., FIGS. 7-9 11A-11F, and 12A-12B and the following examples.

In some versions, the mutant tryptophan decarboxylase proteins of the invention comprise an amino acid sequence at least about 90%, at least about 91%, at least about 92%, at least about 93%, at least about 94%, at least about 95%, at least about 96%, at least about 97%, at least about 98%, or at least about 99% identical to SEQ ID NO:1 fused to a heterologous amino acid sequence. The heterologous amino acid sequence can constitute a primary structure of any of a number of heterologous domains. Exemplary domains include linkers, affinity tags, or other catalytically active domains, among others. Linkers employed to fuse two heterologous polypeptides or domains to generate fusion proteins are well known in the art. See, e.g., U.S. Pat. Nos. 5,525,491, 6,274,331, 6,479,626, 10,526,379, 10,752,965, and 11,123,438, among others. Exemplary linkers include linkers comprising glycine and serine, such as a -G-S- linker or a -G-S-G- linker. Exemplary linker lengths can be from 1-20 residues in length, such as from 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2 residues in length. Exemplary affinity tags include the His tag, the Strep II tag, the T7 tag, the FLAG tag, the S tag, the HA tag, the c-Myc tag, the dihydrofolate reductase (DHFR) tag, the chitin binding domain tag, the calmodulin binding domain tag, and the cellulose binding domain tag. The sequences of each of these tags are well-known in the art. Preferred affinity tags are those smaller than about 20 amino acids, such as the His tag, the Strep II tag, the T7 tag, the FLAG tag, the S tag, the HA tag, the c-Myc tag. Domains fused to the amino acid sequence of at least about 90%, at least about 91%, at least about 92%, at least about 93%, at least about 94%, at least about 95%, at least about 96%, at least about 97%, at least about 98%, or at least about 99% identical to SEQ ID NO:1 can be fused either directly or indirectly via a linker and, in various versions, can have a size less than 500 amino acids in length, less than 475 amino acids in length, less than 450 amino acids in length, less than 425 amino acids in length, less than 400 amino acids in length, less than 375 amino acids in length, less than 350 amino acids in length, less than 325 amino acids in length, less than 300 amino acids in length, less than 275 amino acids in length, less than 250 amino acids in length, less than 225 amino acids in length, less than 200 amino acids in length, less than 175 amino acids in length, less than 150 amino acids in length, less than 125 amino acids in length, less than 100 amino acids in length, less than 75 amino acids in length, less than 50 amino acids in length, or less than 25 amino acids in length. The heterologous amino acid sequence can be fused to the N-terminus or the C-terminus of the amino acid sequence at least about 90%, at least about 91%, at least about 92%, at least about 93%, at least about 94%, at least about 95%, at least about 96%, at least about 97%, at least about 98%, or at least about 99% identical to SEQ ID NO:1.

The mutant tryptophan decarboxylase proteins of the invention may have mutations with respect to a corresponding tryptophan decarboxylase protein. "Corresponding tryptophan decarboxylase protein" refers to a protein comprising or consisting of a corresponding amino acid sequence. A corresponding sequence is a sequence that aligns to the sequence of a given mutant tryptophan decarboxylase protein, or any portion thereof, using bioinformatic techniques, for example, using the methods described herein for preparing a sequence alignment. The corresponding sequence preferably has at least 90% identity, at least 91% identity, at least 92% identity, at least 93% identity, at least 94% identity, at least 95% identity, at least 96% identity, at least 97% identity, at least 98% identity, at least 99% identity, or 100% identity to the mutant tryptophan decarboxylase sequence over the aligned portions of each sequence. The corresponding amino acid sequence is preferably a native amino acid sequence. An exemplary corresponding amino acid sequence is the sequence of SEQ ID NO:1. An exemplary corresponding tryptophan decarboxylase protein is a protein consisting of or comprising the sequence of SEQ ID NO:1.

The mutant tryptophan decarboxylase proteins of the invention exhibit activity in decarboxylating unsubstituted and/or substituted tryptophan substrates. In some versions, the substituted tryptophan substrates have a substituent at one or more of the 2 position, the 4 position, the 5 position, the 6 position, or the 7 position on the substituted tryptophan. See FIG. 2 for the tryptophan position numbering.

The mutant tryptophan decarboxylase proteins of the invention preferably have at least one altered property compared to the properties of a corresponding tryptophan decarboxylase protein. In some versions, the corresponding tryptophan decarboxylase protein is a protein comprising an amino acid sequence 100% identical to SEQ ID NO:1. In some versions, the corresponding tryptophan decarboxylase protein is a protein consisting of an amino acid sequence 100% identical to SEQ ID NO:1.

The altered property preferably comprises an enhancement of activity in decarboxylating unsubstituted and/or substituted tryptophan substrates. The altered property may be exhibited in vitro, in vivo, or both in vitro and in vivo.

Figure 11A:
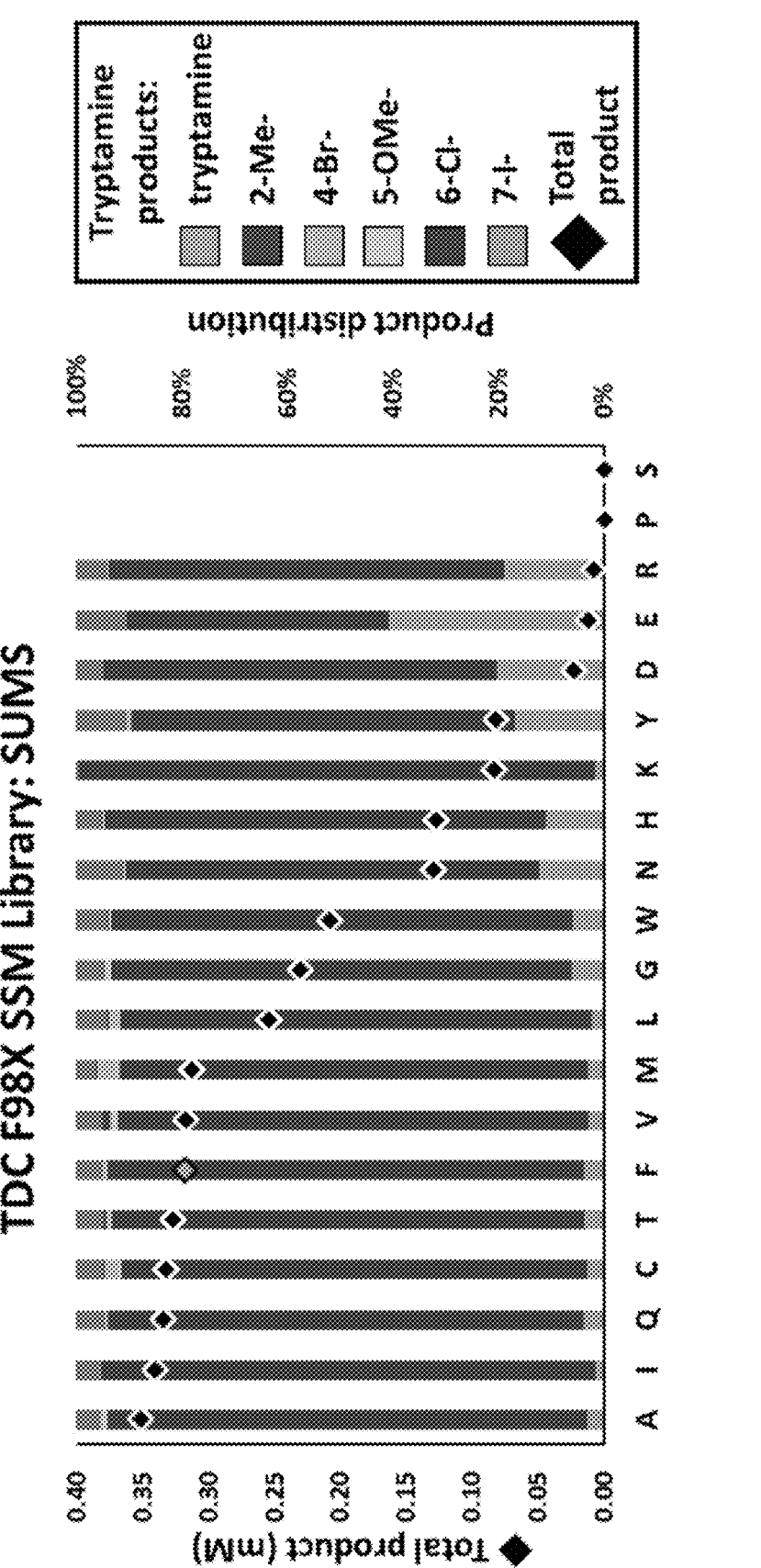
FIGS. 11A-11F. Retention of function (ROF) curves from substrate-multiplexed screening (SUMS) of site-saturation mutagenesis (SSM) libraries. Stacked bars represent relative amounts of each product formed (from top to bottom: tryptamine, 2-Me-, 4-Br—, 5-OMe-, 6-Cl—, and 7-I—), and diamonds represent mM total product produced, as determined by single-ion retention standard curves. The wild-type sequence is denoted by a grey diamond. Relative product amounts and mM total product were averaged from all wells with the given sequence.
Figure 11B:
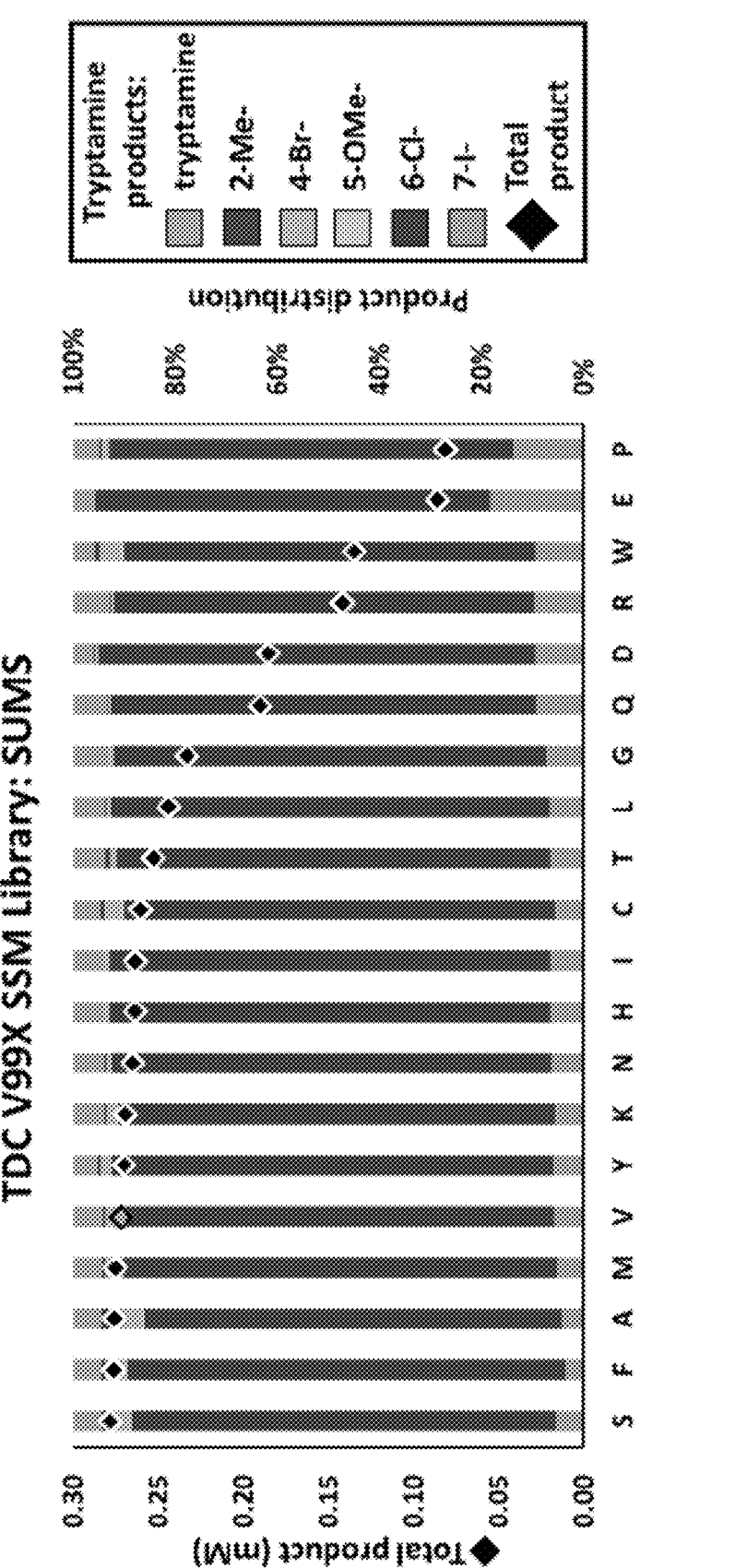
Figure 11C:
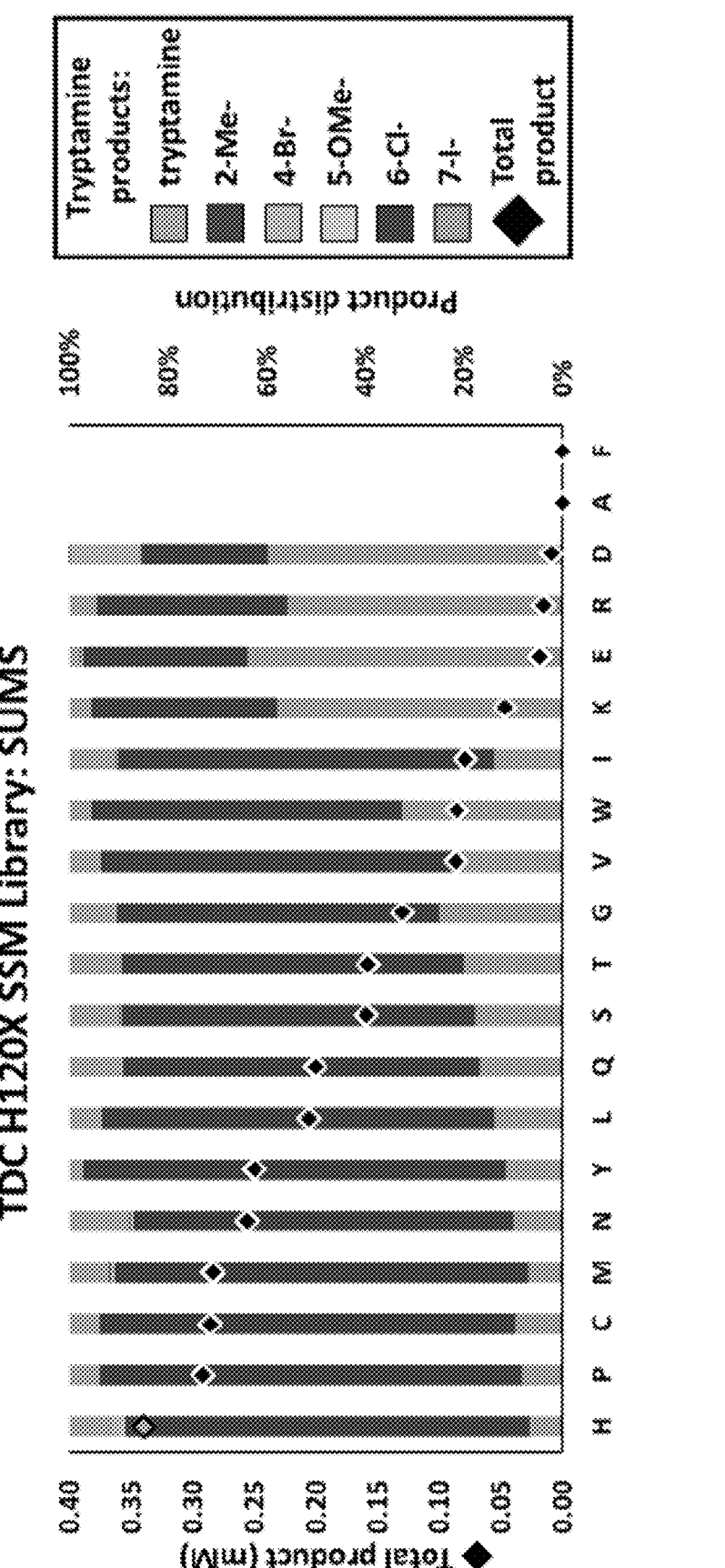
Figure 11D:
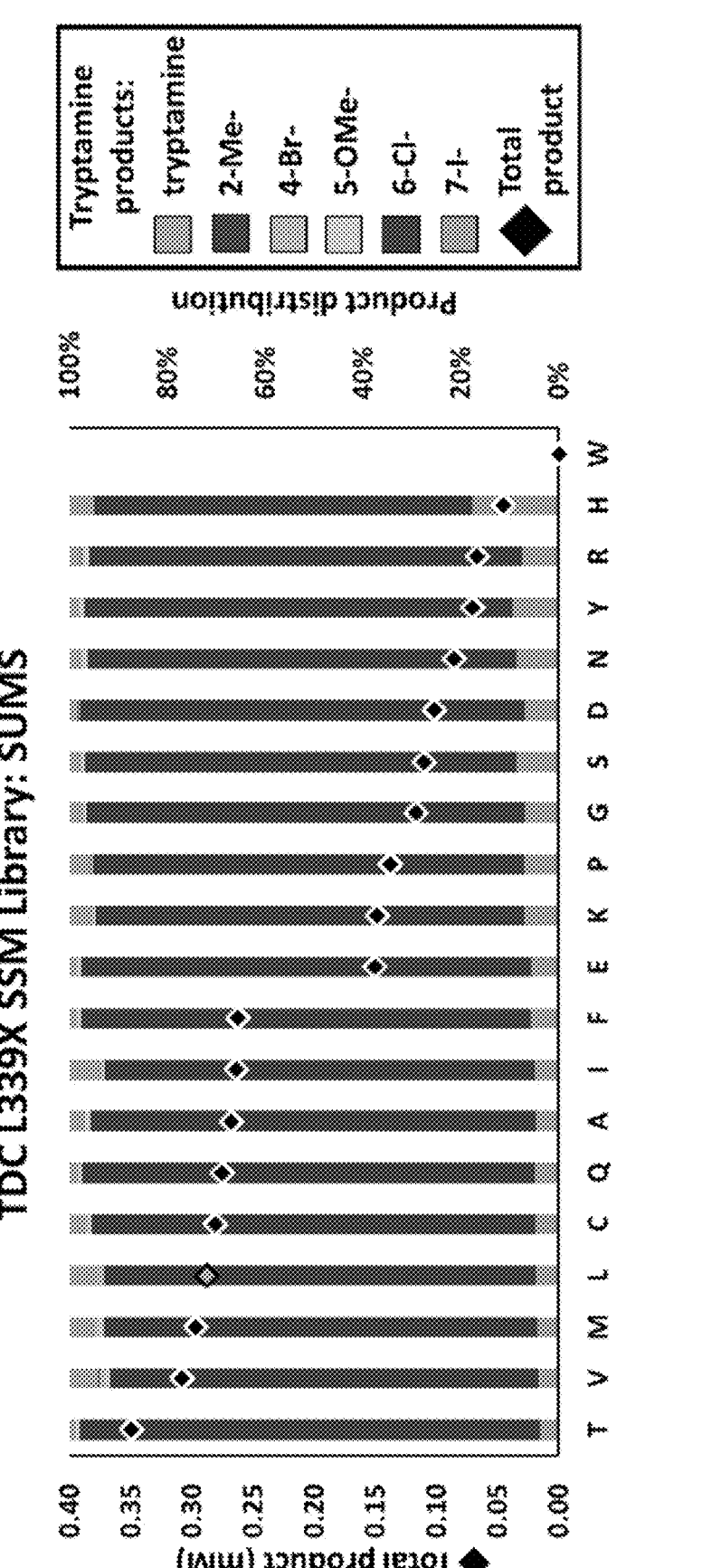
Figure 11E:
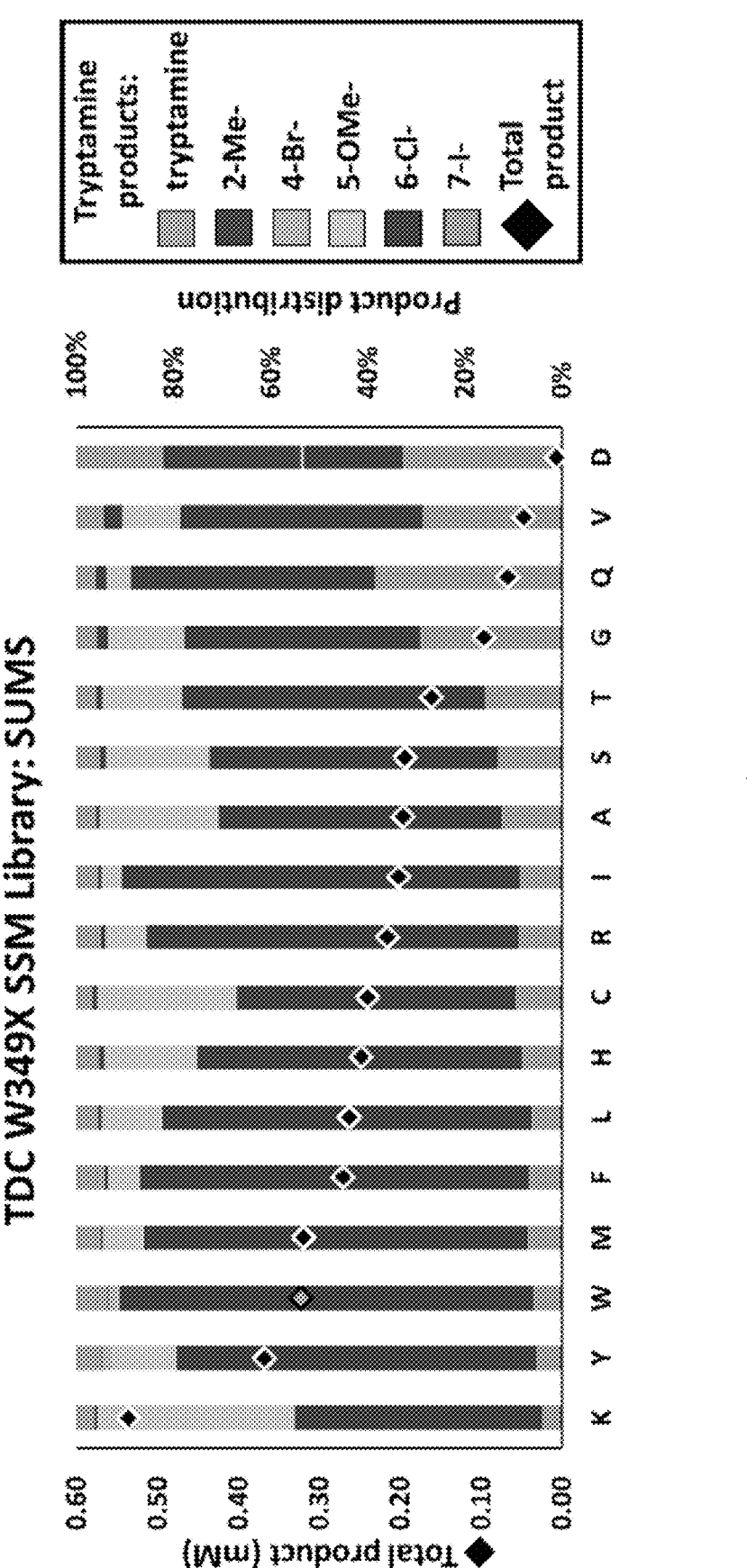
Figure 11F:
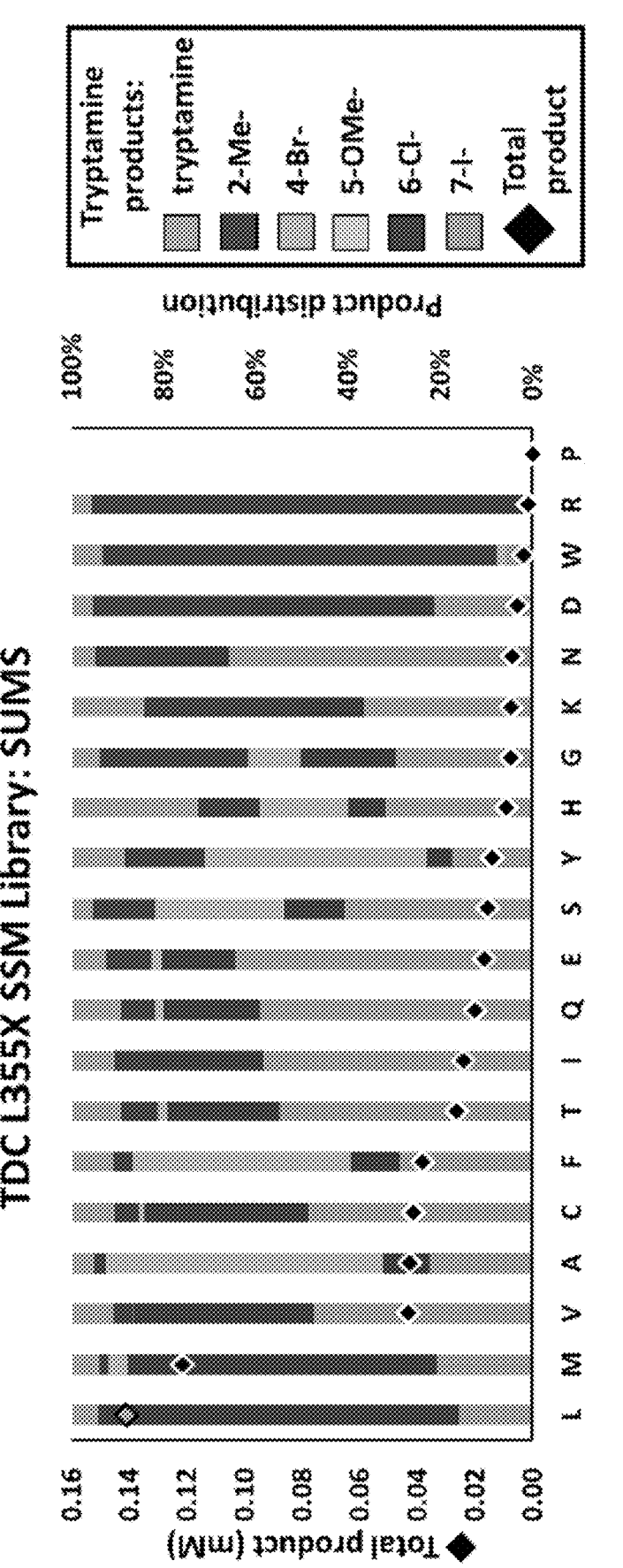
Figure 12A:
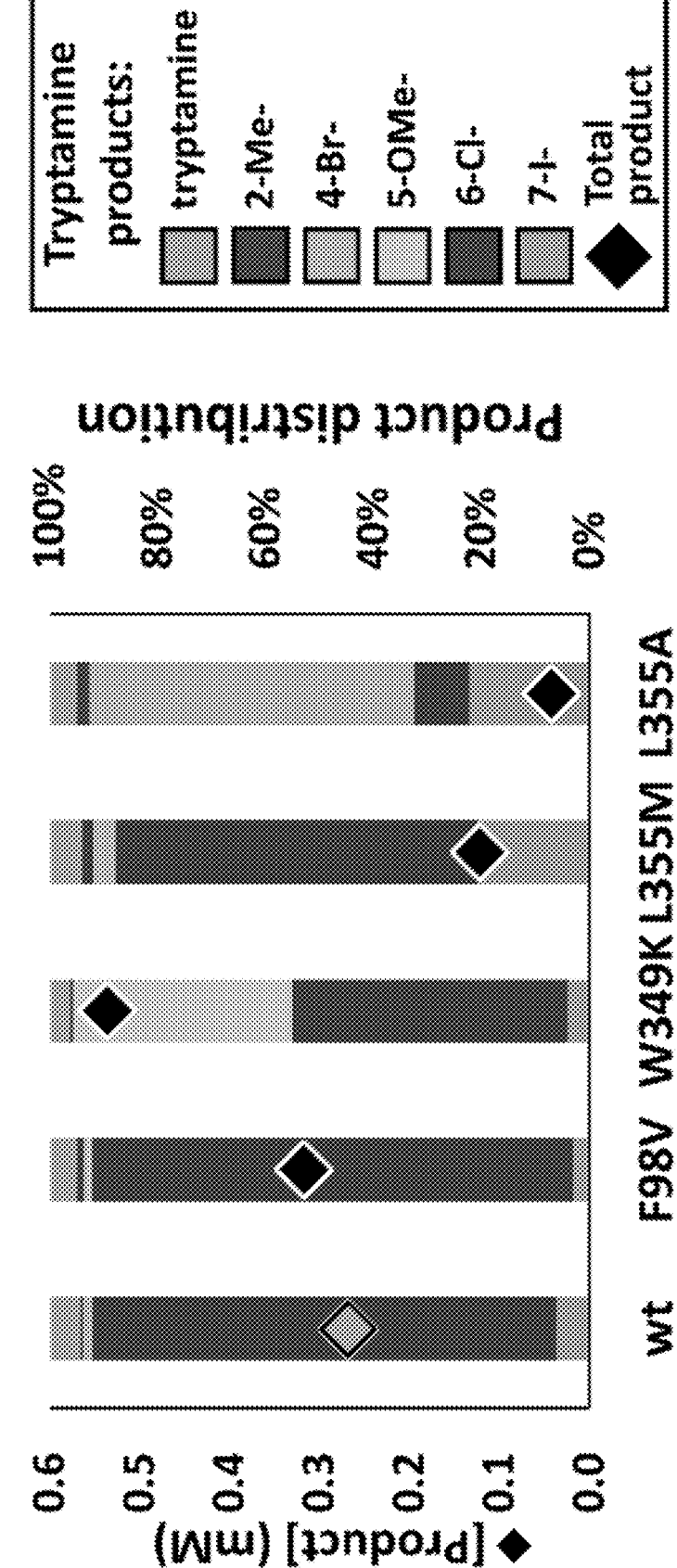
FIGS. 12A-12C. SUMS identifies RgnTDC active site mutation that improve activity for a range of substrates.
Figures 12B, 12C:
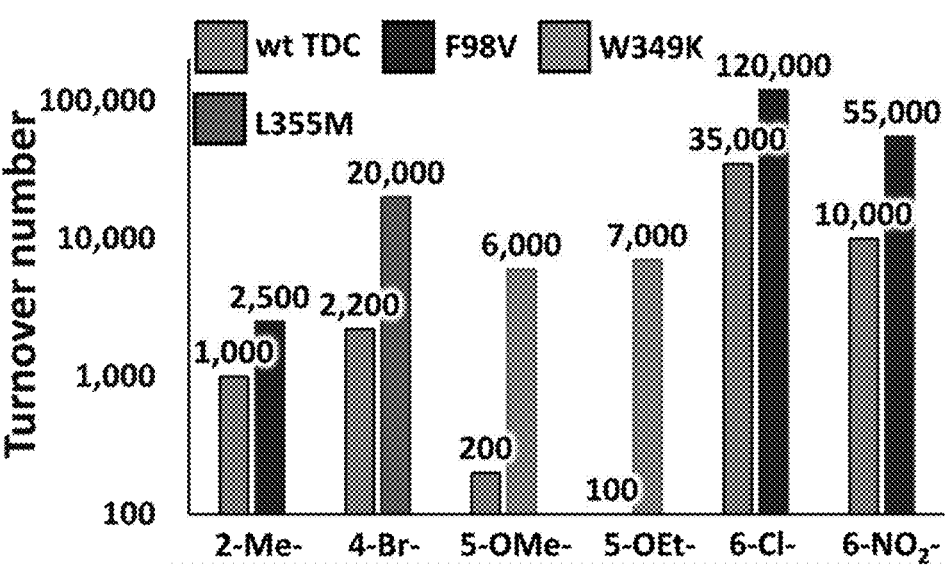

In some versions, the altered property comprises increased activity in decarboxylating a tryptophan analog substrate, such as a substituted tryptophan substrate. The substituted tryptophan substrate in some versions comprises a substituent at any one or more, any two or more, any three or more, any four or more, or each of a 2 position, a 4 position, a 5 position, a 6 position, or a 7 position on the substituted tryptophan. Exemplary substitutions conferring increased activity in decarboxylating a substituted tryptophan substrates are provided in FIGS. 11A-11F and 12A-12C. As shown in FIG. 12C, for example, an L355M substitution in SEQ ID NO:1 increases the activity in decarboxylating 4-bromotryptophan, a W349K substitution in SEQ ID NO:1 increases the activity in decarboxylating 5-methoxytryptophan, and an F98V substitution in SEQ ID NO:1 increases the activity in decarboxylating 6-chlorotryptophan.

Figure 7:
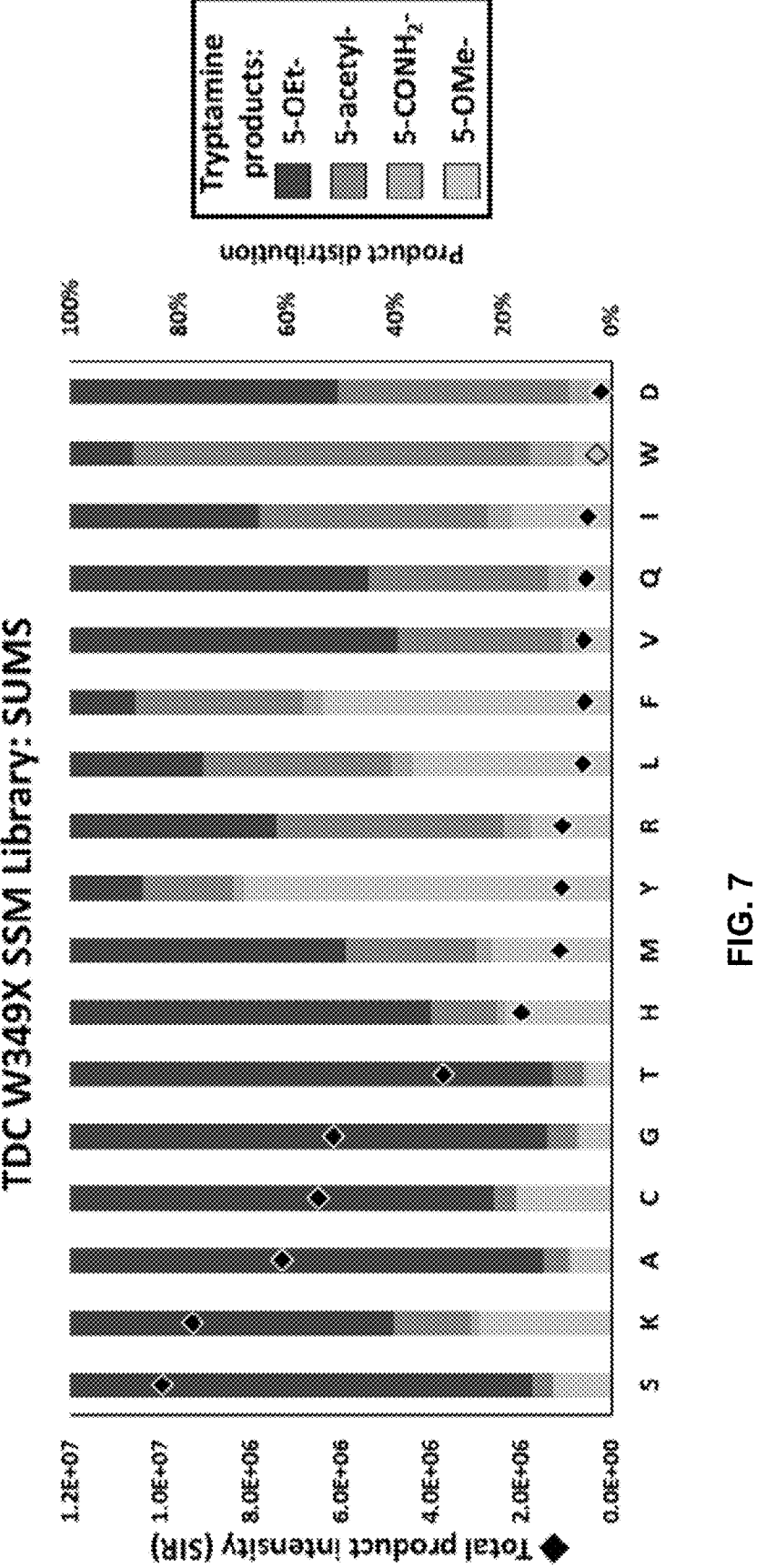
FIG. 7. Results from substrate-multiplexed screening (SUMS) of the W349 site-saturation mutagenesis (SSM) library with various 5-substituted tryptophan analogs. Stacked bars represent relative amounts of each product formed (from top to bottom: 5-OEt-, 5-acetyl-, 5-$CONH_2$—, and 5-OMe-), and black diamonds indicate total intensity of single ion retention (SIR) from each product's unique m/z. The wild-type sequence is denoted by a grey diamond. Relative product amounts and SIR intensity were averaged from all wells with the given sequence. 2-methyl, 5-methoxytryptophan was also included as a potential substrate, but no product was observed.

In some versions, the altered property comprises increased activity in decarboxylating a first substrate relative to a second substrate, wherein the first substrate is not the second substrate. The first substrate in some versions is selected from the group consisting of any one or more, any two or more, any three or more, any four or more, or each of 2-substituted tryptophan, 4-substituted tryptophan, 5-substituted tryptophan, 6-substituted tryptophan, and 7-substituted tryptophan. The second substrate in some versions is selected from the group consisting of any one or more, any two or more, any three or more, any four or more, any five or more, or each of unsubstituted tryptophan, 2-substituted tryptophan, 4-substituted tryptophan, 5-substituted tryptophan, 6-substituted tryptophan, and 7-substituted tryptophan. Exemplary substitutions conferring increased activity in decarboxylating various first substrates relative to various second substrates are provided in FIGS. 7-9, 11A-11F, and 12A-12C. As shown in FIG. 7, for example, a W349S substitution in SEQ ID NO:1 increases, compared to unmodified SEQ ID NO:1, the activity in decarboxylating 5-ethoxytryptophan relative to 5-acetyltryptophan. As shown in FIG. 11E, a W349K substitution in SEQ ID NO:1 increases, compared to unmodified SEQ ID NO:1, the activity in decarboxylating a 5-substituted tryptophan (5-methoxytryptophan) relative to a 6-substituted tryptophan (6-chlorotryptophan).

In some versions, the altered property comprises increased combined activity in decarboxylating any two or more different substrates. In some versions, the two or more different substrates are selected from the group consisting of unsubstituted tryptophan, one or more 2-substituted tryptophans, one or more 4-substituted tryptophans, one or more 5-substituted tryptophans, one or more 6-substituted tryptophans, and one or more 7-substituted tryptophans. Exemplary substitutions conferring increased combined activity in decarboxylating any two or more different substrates are provided in FIGS. 7-9, 11A-11F, and 12A-12C. As shown in FIG. 7, for example, W349S, W349K, W349A, W349C, W349G, W349T, W349H, and other substitutions in SEQ ID NO:1 increase the combined activity in decarboxylating 5-ethoxy tryptophan, 5-acetyltryptophan, 5-carboxamidotryptophan, and 5-methoxytryptophan compared to unmodified SEQ ID NO:1. As shown in FIG. 11A, F98A, F981, F98Q, F98C, and F98T substitutions in SEQ ID NO:1 increase the combined activity in decarboxylating 2-methyltryptophan, 4-bromotryptophan, 5-methoxytryptophan, 6-chlorotryptophan, 7-iodotryptophan, and tryptophan compared to unmodified SEQ ID NO:1.

In some versions, the increase in activity comprises an increase in $k_{cat}$ in decarboxylating a given substrate. In some versions, the increase in activity comprises a decrease in $K_m$ in decarboxylating a given substrate. In some versions, the increase in activity comprises an increase in $k_{cat}/K_m$ in decarboxylating a given substrate. In some versions, the increase in activity comprises an increase in the amount (e.g., in mM) of a product produced through decarboxylating a given substrate over a period of time.

Another aspect of the invention is a polynucleotide (or a gene) encoding a mutant tryptophan decarboxylase protein of the invention. Another aspect of the invention is a vector comprising the polynucleotide (or the gene) according to the invention. Vectors of the invention can be transformed into suitable host cells to produce recombinant host cells.

Another aspect of the invention is a recombinant host cell comprising a polynucleotide encoding a mutant tryptophan decarboxylase protein of the invention. In some versions, known genomic alteration or modification techniques can be employed to alter or modify the endogenous tryptophan decarboxylase protein of the host cell, effectuating one or more of the aforementioned mutations, such that at least one of the mutant endogenous tryptophan decarboxylase proteins has at least one altered property. In other versions, the recombinant host cell is engineered to include a plasmid comprising a polynucleotide encoding a mutant tryptophan decarboxylase protein. In yet other versions, the recombinant host cell is engineered to include the polynucleotide encoding the mutant tryptophan decarboxylase protein integrated into the chromosome of the host cell.

The recombinant host cell of the invention can be selected from any cell capable of expressing a recombinant gene construct, and can be selected from a microbial, plant or animal cell. In a particular embodiment, the host cell is bacterial, cyanobacterial, fungal, yeast, algal, human or mammalian in origin. In a particular embodiment, the host cell is selected from any of Gram positive bacterial species such as Actinomycetes; Bacillaceae, including *Bacillus alkalophilus, Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, B. thuringiensis; Brevibacteria* sp., including *Brevibacterium flavum, Brevibacterium lactofermentum, Brevibacterium ammoniagenes, Brevibacterium butanicum, Brevibacterium divaricatum, Brevibacterium healii, Brevibacterium ketoglutamicum, Brevibacterium ketosoreductum, Brevibacterium lactofermentum, Brevibacterium linens, Brevibacterium paraffinolyticum; Corynebacterium* spp. such as *C. glutamicum* and *C. melassecola, Corynebacterium herculis, Corynebacterium lilium, Corynebacterium acetoacidophilum, Corynebacterium acetoglutamicum, Corynebacterium acetophilum, Corynebacterium ammoniagenes, Corynebacterium fujiokense, Corynebacterium nitrilophilus*; or lactic acid bacterial species including *Lactococcus* spp. such as *Lactococcus lactis; Lactobacillus* spp. including *Lactobacillus reuteri; Leuconostoc* spp.; *Pediococcus* spp.; *Serratia* spp. such as *Serratia marcescens; Streptomyces* species, such as *Streptomyces lividans, Streptomyces murinus, S. coelicolor* and *Streptococcus* spp. Alternatively, strains of a Gram negative bacterial species belonging to Enterobacteriaceae including *E. coli, Cellulomonas* spp.; or to Pseudomonadaceae including *Pseudomonas aeruginosa, Pseudomonas alcaligenes, Pseudomonas fluorescens, Pseudomonas putida, Pseudomonas syringae* and *Burkholderia cepacia, Salmonella* sp., *Stenotrophomonas* spp., and *Stenotrophomonas maltophilia*. Microorganisms such as *Rhodococcus* spp, *Rhodococcus opacus, Ralstonia* spp., and *Acetinobacter* spp. are useful as well. Furthermore, yeasts and filamentous fungal strains can be useful host cells, including *Absidia* spp.; *Acremonium* spp.; *Agaricus* spp.; *Anaeromyces* spp.; *Aspergillus* spp., including *A. aculeatus, A. awamori, A. flavus, A. foetidus, A. fumaricus, A. fumigatus, A. nidulans, A. niger, A. oryzae, A. terreus; A. tubingensis* and *A. versicolor; Aeurobasidium* spp.; *Cephalosporum* spp.; *Chaetomium* spp.; *Coprinus* spp.; *Dactyllum* spp.; *Fusarium* spp., including *F. conglomerans, F. decemcellulare, F. javanicum, F. lini, F. oxysporum* and *F. solani; Gliocladium* spp.; *Kluyveromyces* sp.; *Hansenula* sp.; *Humicola* spp., including *H. insolens* and *H. lanuginosa; Hypocrea* spp.; *Mucor* spp.; *Neurospora* spp., including *N. crassa* and *N. sitophila; Neocallimastix* spp.; *Orpinomyces* spp.; *Penicillium* spp.; *Phanerochaete* spp.; *Phlebia* spp.; *Pichia* sp.; *Piromyces* spp.; *Rhizopus* spp.; *Rhizomucor* species such as *Rhizomucor miehei; Saccaromyces* species such as *S. cerevisiae, S. pastorianus, S. eubayanus*, and *S. fragilis; Schizophyllum* spp.; *Schizosaccharomyces* such as, for example, *S. pombe* species; *chytalidium* sp., *Sulpholobus* sp., *Thermoplasma* sp., *Thermomyces* sp.; *Trametes* spp.; *Trichoderma* spp., including *T. reesei, T. reesei (longibrachiatum)* and *T. viride; Yarrowinia* sp.; and *Zygorhynchus* spp and in particular include oleaginous yeast just *Phafia* spp., *Rhorosporidium toruloides* Y4, *Rhodotorula Glutinis* and *Candida* 107.

In some versions of the invention, genes encoding mutant tryptophan decarboxylase proteins and/or other recombinantly expressed genes in a recombinant host cell are modified to optimize at least one codon for expression in the recombinant host cell.

In some versions of the invention, a method is provided wherein the recombinant host cell according to the invention is cultured under conditions that permit expression or over-expression of a mutant tryptophan decarboxylase protein of the invention. The mutant tryptophan decarboxylase protein can be recovered, and more preferably substantially purified, after the host cell is harvested and/or lysed.

Another aspect of the invention is directed to methods of generating products with the mutant tryptophan decarboxylase proteins of the invention. The methods preferably comprise contacting a substrate with a mutant tryptophan decarboxylase protein of the invention to thereby generate the product. The substrate preferably comprises a tryptophan analog. In some versions, the substrate comprises one or more of tryptophan and substituted tryptophan. The product in some versions comprises one or more of tryptamine or substituted tryptamine. In some versions, the substituted tryptophan comprises a substituent at any one or more of a 2 position, a 4 position, a 5 position, a 6 position, or a 7 position on the substituted tryptophan. See FIG. 2 for the position numbering on the substituted tryptophan.

The methods of the invention can further comprise generating the substrate. Generating the substrate can comprise contacting an upstream substrate with a tryptophan synthase to thereby generate the substrate. The upstream substrate preferably comprises an indole analog. In some versions, the upstream substrate comprises one or more of indole or substituted indole. In some versions, the substituted indole comprises a substituent at any one or more of a 2 position, a 4 position, a 5 position, a 6 position, or a 7 position on the substituted indole. See FIG. 13 for the position numbering on the substituted indole. In some versions, generating the substrate comprises contacting the upstream substrate and serine with the tryptophan synthase. In some versions, generating the substrate comprises contacting the upstream substrate and serine with the tryptophan synthase in the presence of pyridoxal 5'-phosphate (PLP).

The generation of the product and/or the substrate can be performed in any of a number of formats.

In some versions, the generation of the product and/or the substrate is performed in vitro. In such versions, the tryptophan synthase and/or the tryptophan decarboxylase are preferably in a purified form, e.g., are not present within a cell. In some versions, the tryptophan synthase and/or the tryptophan decarboxylase are in a purified form in a reaction medium also comprising the substrate and/or the upstream substrate, respectively. In some versions, the generation of the product is performed in vitro. In some versions, the generation of the substrate is performed in vitro. In some versions, the generation of the product and the substrate are performed separately in vitro. Some versions can comprise an in vitro biosynthetic cascade in which purified forms of the tryptophan synthase and the tryptophan decarboxylase are present in a reaction medium in the presence of the upstream substrate, wherein the tryptophan synthase converts the upstream substrate to the substrate and the tryptophan decarboxylase converts the substrate to the product.

In some versions, the generation of the product and/or the substrate is performed intracellularly in vivo. In such versions, the tryptophan synthase and/or the tryptophan decarboxylase are preferably comprised within a cell. In some versions, the tryptophan synthase and/or the tryptophan decarboxylase are comprised within a cell also comprising the substrate and/or the upstream substrate, respectively. In some versions, the generation of the product is performed intracellularly. In some versions, the generation of the substrate is performed intracellularly. Some versions can comprise an intracellular biosynthetic cascade in which the tryptophan synthase and the tryptophan decarboxylase are both contained within a cell in the presence of the upstream substrate, wherein the tryptophan synthase converts the upstream substrate to the substrate and the tryptophan decarboxylase converts the substrate to the product.

Any tryptophan synthase can be used in the methods described herein. An exemplary tryptophan synthase is the tryptophan synthase from *Pyrococcus furiosus* (PfTrpB) (TrpB2B9) comprising the amino acid sequence of SEQ ID NO:3):

```
                                              (SEQ ID NO: 3)
MWFGEFGGQYVPETLVGPLKELEKAYKRFKDDEEFNRQLNYYLKTWAGRP

TPLYYAKRLTEKIGGAKVYLKREDLVHGGAHKTNNAIGQALLAKLMGKTR

LIAETGAGQHGVATAMAGALLGMKVDIYMGAEDVERQKMNVFRMKLLGAN

VIPVNSGSRTLKDAINEALRDWVATFEYTHYLIGSVVGPHPYPTIVRDFQ

SVIGREAKAQILEAEGQLPDVIVACVGGGSNAMGIFYPFVNDKKVKLVGV

EAGGKGLESGKHSASLNAGQVGVSHGMLSYFLQDEEGQIKPSHSIAPGLD

YPGVGPEHAYLKKIQRAEYVAVTDEEALKAFHELSRTEGIIPALESAHAV

AYAMKLAKEMSRDEIIIVNLSGRGDKDLDIVLKASGNVLEHHHHHH
```

An exemplary coding sequence for the tryptophan synthase protein represented by SEQ ID NO:3 is SEQ ID NO:4:

```
                                              (SEQ ID NO: 4)
ATGTGGTTCGGTGAATTTGGTGGTCAGTACGTGCCAGAAACGCTGGTTGG

ACCCCTGAAAGAGCTGGAAAAAGCTTACAAACGTTTCAAAGATGACGAAG

AATTCAATCGTCAGCTGAATTACTACCTGAAAACCTGGGCAGGTCGTCCA

ACCCCACTGTACTACGCAAAACGCCTGACTGAAAAAATCGGTGGTGCTAA

AGTCTACCTGAAACGTGAAGACCTGGTTCACGGTGGTGCACACAAGACCA

ACAACGCCATCGGTCAGGCACTGCTGGCAAAGCTCATGGGTAAAACTCGT

CTGATCGCTGAGACCGGTGCTGGTCAGCACGGCGTAGCGACTGCAATGGC

TGGTGCACTGCTGGGCATGAAAGTGGACATTTACATGGGTGCTGAGGACG

TAGAACGTCAGAAAATGAACGTATTCCGTATGAAGCTGCTGGGTGCAAAC

GTAATTCCAGTTAACTCCGGTTCTCGCACCCTGAAAGACGCAATCAACGA

GGCTCTGCGTGATTGGGTGGCTACTTTTGAATACACCCACTACCTAATCG

GTTCCGTGGTCGGTCCACATCCGTATCCGACCATCGTTCGTGATTTTCAG

TCTGTTATCGGTCGTGAGGCTAAAGCGCAGATCCTGGAGGCTGAAGGTCA

GCTGCCAGATGTAATCGTTGCTTGTGTTGGTGGTGGCTCTAACGCGATGG

GTATCTTTTACCCGTTCGTGAACGACAAAAAAGTTAAGCTGGTTGGCGTT

GAGGCTGGTGGTAAAGGCCTGGAATCTGGTAAGCATTCCGCTAGCCTGAA

CGCAGGTCAGGTTGGTGTGTCCCATGGCATGCTGTCCTACTTTCTGCAGG
```

```
-continued
ACGAAGAAGGTCAGATCAAACCAAGCCACTCCATCGCACCAGGTCTGGAT

TATCCAGGTGTTGGTCCAGAACACGCTTACCTGAAAAAAATTCAGCGTGC

TGAATACGTGGCTGTAACCGATGAAGAAGCACTGAAAGCGTTCCATGAAC

TGAGCCGTACCGAAGGTATCATCCCAGCTCTGGAATCTGCGCATGCTGTG

GCTTACGCTATGAAACTGGCTAAGGAAATGTCTCGTGATGAGATCATCAT

CGTAAACCTGTCTGGTCGTGGTGACAAAGACCTGGATATTGTCCTGAAAG

CGTCTGGCAACGTGCTCGAGCACCACCACCACCACCACTGA
```

Homologs of PfTrpB are also suitable for the methods described herein, including homologs comprising a sequence at least 80%, 80%, 80%, 85%, 90%, 95%, or 99% identical to SEQ ID NO:3. The tryptophan synthase can have any substitutions corresponding to the exemplary substitutions provided herein.

Throughout the specification, a reference may be made using an abbreviation of a gene name or a protein name, but it is understood that such an abbreviated gene or protein name represents the genus of genes or proteins, respectively. Such gene names include all genes encoding the same protein and homologous proteins having the same physiological function. Protein names include all proteins that have the same activity (e.g., that catalyze the same fundamental chemical reaction).

Unless otherwise indicated, the accession numbers referenced herein are derived from the NCBI database (National Center for Biotechnology Information) maintained by the National Institute of Health, U.S.A.

EC numbers are established by the Nomenclature Committee of the International Union of Biochemistry and Molecular Biology (NC-IUBMB) (available at www.chem.qmul/ac/uk/iubmb/enzyme/). The EC numbers referenced herein are derived from the KEGG Ligand database, maintained by the Kyoto Encyclopedia of Genes and Genomics, sponsored in part by the University of Tokyo.

The term "tryptophan decarboxylase protein," refers to an enzyme that has activity as defined under Enzyme Commission Number: 4.1.1.105. The term "mutant tryptophan decarboxylase protein" refers to a mutated form of a tryptophan decarboxylase protein that has activity in decarboxylating unsubstituted and/or substituted tryptophan substrates The term "altered property" refers to a modification in one or more properties of a mutant polynucleotide or mutant protein with reference to a corresponding polynucleotide or precursor protein.

The term "alignment" refers to a method of comparing two or more polynucleotides or polypeptide sequences for the purpose of determining their relationship to each other. Alignments are typically performed by computer programs that apply various algorithms, however it is also possible to perform an alignment by hand. Alignment programs typically iterate through potential alignments of sequences and score the alignments using substitution tables, employing a variety of strategies to reach a potential optimal alignment score. Commonly-used alignment algorithms include, but are not limited to, CLUSTALW, (see, Thompson J. D., Higgins D. G., Gibson T. J., CLUSTAL W: improving the sensitivity of progressive multiple sequence alignment through sequence weighting, position-specific gap penalties and weight matrix choice, Nucleic Acids Research 22: 4673-4680, 1994); CLUSTALV, (see, Larkin M. A., et al., CLUSTALW2, ClustalW and ClustalX version 2, Bioinformatics 23(21): 2947-2948, 2007); Jotun-Hein, Muscle et al., MUSCLE: a multiple sequence alignment method with reduced time and space complexity, BMC Bioinformatics 5: 113, 2004); Mafft, Kalign, ProbCons, and T-Coffee (see Notredame et al., T-Coffee: A novel method for multiple sequence alignments, Journal of Molecular Biology 302: 205-217, 2000). Exemplary programs that implement one or more of the above algorithms include, but are not limited to MegAlign from DNAStar (DNAStar, Inc. 3801 Regent St. Madison, Wis. 53705), MUSCLE, T-Coffee, CLUSTALX, CLUSTALV, JalView, Phylip, and Discovery Studio from Accelrys (Accelrys, Inc., 10188 Telesis Ct, Suite 100, San Diego, Calif. 92121). In a non-limiting example, MegAlign is used to implement the CLUSTALW alignment algorithm with the following parameters: Gap Penalty 10, Gap Length Penalty 0.20, Delay Divergent Seqs (30%) DNA Transition Weight 0.50, Protein Weight matrix Gonnet Series, DNA Weight Matrix IUB.

The term "chromosomal integration" means the process whereby an incoming sequence is introduced into the chromosome of a host cell. The homologous regions of the transforming DNA align with homologous regions of the chromosome. Then, the sequence between the homology boxes can be replaced by the incoming sequence in a double crossover (i.e., homologous recombination). In some embodiments of the present invention, homologous sections of an inactivating chromosomal segment of a DNA construct align with the flanking homologous regions of the indigenous chromosomal region of the microbial chromosome. Subsequently, the indigenous chromosomal region is deleted by the DNA construct in a double crossover.

The term "consensus sequence" or "canonical sequence" refers to an archetypical amino acid sequence against which all variants of a particular protein or sequence of interest are compared. Either term also refers to a sequence that sets forth the nucleotides that are most often present in a polynucleotide sequence of interest. For each position of a protein, the consensus sequence gives the amino acid that is most abundant in that position in the sequence alignment.

The term "conservative substitutions" or "conserved substitutions" refers to, for example, a substitution of an amino acid with a conservative variant.

"Conservative variant" refers to residues that are functionally similar to a given residue. Amino acids within the following groups are conservative variants of one another: glycine, alanine, serine, and proline (very small); alanine, isoleucine, leucine, methionine, phenylalanine, valine, proline, and glycine (hydrophobic); alanine, valine, leucine, isoleucine, methionine (aliphatic-like); cysteine, serine, threonine, asparagine, tyrosine, and glutamine (polar); phenylalanine, tryptophan, tyrosine (aromatic); lysine, arginine, and histidine (basic); aspartate and glutamate (acidic); alanine and glycine; asparagine and glutamine; arginine and lysine; isoleucine, leucine, methionine, and valine; and serine and threonine.

The terms "corresponds to" and "corresponding to" used with reference to an amino acid residue or position refer to an amino acid residue or position in a first protein sequence being positionally equivalent to an amino acid residue or position in a second reference protein sequence by virtue of the fact that the residue or position in the first protein sequence aligns to the residue or position in the reference sequence using bioinformatic techniques, for example, using the methods described herein for preparing a sequence alignment. The corresponding residue in the first protein sequence is then assigned the position number in the second reference protein sequence.

The term "deletion," when used in the context of an amino acid sequence, means a deletion in or a removal of one or more residues from the amino acid sequence of a corresponding protein, resulting in a mutant protein having at least one less amino acid residue as compared to the corresponding protein. The term can also be used in the context of a nucleotide sequence, which means a deletion in or removal of a nucleotide from the polynucleotide sequence of a corresponding polynucleotide.

The term "DNA construct" and "transforming DNA" (wherein "transforming" is used as an adjective) are used interchangeably herein to refer to a DNA used to introduce sequences into a host cell or organism. Typically a DNA construct is generated in vitro by PCR or other suitable technique(s) known to those in the art. In certain embodiments, the DNA construct comprises a sequence of interest (e.g., an incoming sequence). In some embodiments, the sequence is operably linked to additional elements such as control elements (e.g., promoters, etc.). A DNA construct can further comprise a selectable marker. It can also comprise an incoming sequence flanked by homology targeting sequences. In a further embodiment, the DNA construct comprises other non-homologous sequences, added to the ends (e.g., stuffer sequences or flanks). In some embodiments, the ends of the incoming sequence are closed such that the DNA construct forms a closed circle. The transforming sequences may be wildtype, mutant or modified. In some embodiments, the DNA construct comprises sequences homologous to the host cell chromosome. In other embodiments, the DNA construct comprises non-homologous sequences. Once the DNA construct is assembled in vitro it may be used to: 1) insert heterologous sequences into a desired target sequence of a host cell; 2) mutagenize a region of the host cell chromosome (i.e., replace an endogenous sequence with a heterologous sequence); 3) delete target genes; and/or (4) introduce a replicating plasmid into the host.

A polynucleotide is said to "encode" an RNA or a polypeptide if, in its native state or when manipulated by methods known to those of skill in the art, it can be transcribed and/or translated to produce the RNA, the polypeptide, or a fragment thereof. The antisense strand of such a polynucleotide is also said to encode the RNA or polypeptide sequences. As is known in the art, a DNA can be transcribed by an RNA polymerase to produce an RNA, and an RNA can be reverse transcribed by reverse transcriptase to produce a DNA. Thus a DNA can encode an RNA, and vice versa.

The term "expressed genes" refers to genes that are transcribed into messenger RNA (mRNA) and then translated into protein, as well as genes that are transcribed into types of RNA, such as transfer RNA (tRNA), ribosomal RNA (rRNA), and regulatory RNA, which are not translated into protein.

The terms "expression cassette" or "expression vector" refer to a polynucleotide construct generated recombinantly or synthetically, with a series of specified elements that permit transcription of a particular polynucleotide in a target cell. A recombinant expression cassette can be incorporated into a plasmid, chromosome, mitochondrial DNA, plasmid DNA, virus, or polynucleotide fragment. Typically, the recombinant expression cassette portion of an expression vector includes, among other sequences, a polynucleotide sequence to be transcribed and a promoter. In particular embodiments, expression vectors have the ability to incorporate and express heterologous polynucleotide fragments in a host cell. Many prokaryotic and eukaryotic expression vectors are commercially available. Selection of appropriate expression vectors is within the knowledge of those of skill in the art. The term "expression cassette" is also used interchangeably herein with "DNA construct," and their grammatical equivalents.

"Gene" refers to a polynucleotide (e.g., a DNA segment), which encodes a polypeptide, and may include regions preceding and following the coding regions as well as intervening sequences (introns) between individual coding segments (exons).

The term "homologous genes" refers to a pair of genes from different but related species, which correspond to each other and which are identical or similar to each other. The term encompasses genes that are separated by the speciation process during the development of new species) (e.g., orthologous genes), as well as genes that have been separated by genetic duplication (e.g., paralogous genes).

The term "endogenous protein" refers to a protein that is native or naturally occurring. "Endogenous polynucleotide" refers to a polynucleotide that is in the cell and was not introduced into the cell using recombinant engineering techniques; for example, a gene that was present in the cell when the cell was originally isolated from nature.

The term "heterologous" used with reference to a protein or a polynucleotide in a host cell refers to a protein or a polynucleotide that does not naturally occur in the host cell.

The term "heterologous" used to describe two different amino acid or nucleic acid sequences refers to two sequences that are not naturally present together in the same protein or nucleic acid. The term "heterologous" used to describe two different protein domains refers to two protein domains that are not naturally present together in the same protein. As used herein, "domain" refers to any portion of protein that confers a particular structural and/or functional characteristic to a protein. Exemplary protein domains include signal peptides, extracellular domains, transmembrane domains, cytoplasmic domains, catalytic domains, affinity tags, and linkers, among others.

The term "homologous recombination" refers to the exchange of DNA fragments between two DNA molecules or paired chromosomes at sites of identical or nearly identical nucleotide sequences. In certain embodiments, chromosomal integration is homologous recombination.

The term "homologous sequences" as used herein refers to a polynucleotide or polypeptide sequence having, for example, about 100%, about 99% or more, about 98% or more, about 97% or more, about 96% or more, about 95% or more, about 94% or more, about 93% or more, about 92% or more, about 91% or more, about 90% or more, about 88% or more, about 85% or more, about 80% or more, about 75% or more, about 70% or more, about 65% or more, about 60% or more, about 55% or more, about 50% or more, about 45% or more, or about 40% or more sequence identity to another polynucleotide or polypeptide sequence when optimally aligned for comparison. In particular embodiments, homologous sequences can retain the same type and/or level of a particular activity of interest. In some embodiments, homologous sequences have between 85% and 100% sequence identity, whereas in other embodiments there is between 90% and 100% sequence identity. In particular embodiments, there is 95% and 100% sequence identity.

"Homology" refers to sequence similarity or sequence identity. Homology is determined using standard techniques known in the art (see, e.g., Smith and Waterman, Adv. Appl. Math., 2:482, 1981; Needleman and Wunsch, J. Mol. Biol., 48:443, 1970; Pearson and Lipman, Proc. Natl. Acad. Sci. USA 85:2444, 1988; programs such as GAP, BESTFIT, FASTA, and TFASTA in the Wisconsin Genetics Software Package (Genetics Computer Group, Madison, Wis.); and Devereux et al., Nucl. Acid Res., 12:387-395, 1984). A non-limiting example includes the use of the BLAST program (Altschul et al., Gapped BLAST and PSI-BLAST: a new generation of protein database search programs, Nucleic Acids Res. 25:3389-3402, 1997) to identify sequences that can be said to be "homologous." A recent version such as version 2.2.16, 2.2.17, 2.2.18, 2.2.19, or the latest version, including sub-programs such as blastp for protein-protein comparisons, blastn for nucleotide-nucleotide comparisons, tblastn for protein-nucleotide comparisons, or blastx for nucleotide-protein comparisons, and with parameters as follows: Maximum number of sequences returned 10,000 or 100,000; E-value (expectation value) of 1e-2 or 1e-5, word size 3, scoring matrix BLOSUM62, gap cost existence 11, gap cost extension 1, may be suitable. An E-value of 1e-5, for example, indicates that the chance of a homologous match occurring at random is about 1 in 10,000, thereby marking a high confidence of true homology.

The term "host strain" or "host cell" refers to a suitable host for an expression vector comprising a DNA of the present invention. The host may comprise any organism, without limitation, capable of containing and expressing the nucleic acids or genes disclosed herein. The host may be prokaryotic or eukaryotic, single-celled or multicellular, including mammalian cells, plant cells, fungi, etc. Examples of single-celled hosts include cells of *Escherichia, Salmonella, Bacillus, Clostridium, Streptomyces, Staphyloccus, Neisseria, Lactobacillus, Shigella*, and *Mycoplasma*. Suitable *E. coli* strains (among a great many others) include BL21(DE3), C600, DH5αF', HB101, JM83, JM101, JM103, JM105, JM107, JM109, JM110, MC1061, MC4100, MM294, NM522, NM554, TGI, χ1776, XL1-Blue, and Y1089+, all of which are commercially available.

The term "identical" (or "identity"), in the context of two polynucleotide or polypeptide sequences, means that the residues in the two sequences are the same when aligned for maximum correspondence, as measured using a sequence comparison or analysis algorithm such as those described herein. For example, if when properly aligned, the corresponding segments of two sequences have identical residues at 5 positions out of 10, it is said that the two sequences have a 50% identity. Most bioinformatic programs report percent identity over aligned sequence regions, which are typically not the entire molecules. If an alignment is long enough and contains enough identical residues, an expectation value can be calculated, which indicates that the level of identity in the alignment is unlikely to occur by random chance.

The term "increased," when used with respect to an increased activity, refers to an increase in activity over a baseline level of activity, regardless of whether the baseline level activity is a positive level of activity or a null level of activity.

The term "insertion," when used in the context of an amino acid sequence, refers to an insertion of an amino acid with respect to the amino acid sequence of a corresponding polypeptide, resulting in a mutant polypeptide having an amino acid that is inserted between two existing contiguous amino acids, i.e., adjacent amino acids residues, which are present in the corresponding polypeptide. The term "insertion," when used in the context of a polynucleotide sequence, refers to an insertion of one or more nucleotides in the corresponding polynucleotide between two existing contiguous nucleotides, i.e., adjacent nucleotides, which are present in the corresponding polynucleotides.

The term "introduced" refers to, in the context of introducing a polynucleotide sequence into a cell, any method suitable for transferring the polynucleotide sequence into the cell. Such methods for introduction include but are not limited to protoplast fusion, transfection, transformation, conjugation, and transduction (see, e.g., Ferrari et al., Genetics, in Hardwood et al, (eds.), *Bacillus*, Plenum Publishing Corp., pp. 57-72, 1989).

The term "isolated" or "purified" means a material that is removed from its original environment, for example, the natural environment if it is naturally occurring, or a cultivation broth if it is produced in a recombinant host cell cultivation medium. A material is said to be "purified" when it is present in a particular composition in a higher concentration than the concentration that exists prior to the purification step(s). For example, with respect to a composition normally found in a naturally-occurring or wild type organism, such a composition is "purified" when the final composition does not include some material from the original matrix. As another example, where a composition is found in combination with other components in a recombinant host cell cultivation medium, that composition is purified when the cultivation medium is treated in a way to remove some component of the cultivation, for example, cell debris or other cultivation products, through, for example, centrifugation or distillation. As another example, a naturally-occurring polynucleotide or polypeptide present in a living animal is not isolated, but the same polynucleotide or polypeptide, separated from some or all of the coexisting materials in the natural system, is isolated, whether such process is through genetic engineering or mechanical separation. Such polynucleotides can be parts of vectors. Alternatively, such polynucleotides or polypeptides can be parts of compositions. Such polynucleotides or polypeptides can be considered "isolated" because the vectors or compositions comprising thereof are not part of their natural environments. In another example, a polynucleotide or protein is said to be purified if it gives rise to essentially one band in an electrophoretic gel or a blot.

The term "mutation" refers to, in the context of a polynucleotide, a modification to the polynucleotide sequence resulting in a change in the sequence of a polynucleotide with reference to a corresponding polynucleotide sequence. A mutation to a polynucleotide sequence can be an alteration that does not change the encoded amino acid sequence, for example, with regard to codon optimization for expression purposes, or that modifies a codon in such a way as to result in a modification of the encoded amino acid sequence. Mutations can be introduced into a polynucleotide through any number of methods known to those of ordinary skill in the art, including random mutagenesis, site-specific mutagenesis, oligonucleotide directed mutagenesis, gene shuffling, directed evolution techniques, combinatorial mutagenesis, site saturation mutagenesis among others.

"Mutation" or "mutated" means, in the context of a protein, a modification to the amino acid sequence resulting in a change in the sequence of a protein with reference to a corresponding protein sequence. A mutation can refer to a substitution of one amino acid with another amino acid, an insertion of one or more amino acid residues, or a deletion of one or more amino acid residues. A mutation can include the replacement of an amino acid with a non-natural amino acid, or with a chemically-modified amino acid or like residues. A mutation can also be a truncation (e.g., a deletion or interruption) in a sequence or a subsequence from the corresponding sequence. A mutation can be made by modifying the DNA sequence corresponding to the corresponding protein. Mutations can be introduced into a protein sequence by known methods in the art, for example, by creating synthetic DNA sequences that encode the mutation with reference to corresponding proteins, or chemically altering the protein itself. A "mutant" as used herein is a protein comprising a mutation.

A "naturally-occurring equivalent," in the context of the present invention, refers to a naturally-occurring tryptophan decarboxylase protein, or a portion thereof that comprises a naturally-occurring residue.

The term "operably linked," in the context of a polynucle-otide sequence, refers to the placement of one polynucle-otide sequence into a functional relationship with another polynucleotide sequence. For example, a DNA encoding a secretory leader (e.g., a signal peptide) is operably linked to a DNA encoding a polypeptide if it is expressed as a preprotein that participates in the secretion of the polypep-tide. A promoter or an enhancer is operably linked to a coding sequence if it affects the transcription of the sequence. A ribosome binding site is operably linked to a coding sequence if it is positioned so as to facilitate trans-lation. Generally, "operably linked" means that the DNA sequences being linked are contiguous, and, in the case of a secretory leader, contiguous and in the same reading frame.

The term "optimal alignment" refers to the alignment giving the highest overall alignment score.

"Overexpressed" or "overexpression" in a host cell occurs if the enzyme is expressed in the cell at a higher level than the level at which it is expressed in a corresponding wild-type cell.

The terms "percent sequence identity," "percent amino acid sequence identity," "percent gene sequence identity," and/or "percent polynucleotide sequence identity," with respect to two polypeptides, polynucleotides and/or gene sequences (as appropriate), refer to the percentage of resi-dues that are identical in the two sequences when the sequences are optimally aligned. Thus, 80% amino acid sequence identity means that 80% of the amino acids in two optimally aligned polypeptide sequences are identical. The percent identities expressed herein with respect to a given named reference sequence are determined over the entire reference sequence, rather than only a portion thereof. Thus, an amino acid sequence at least about 80% identical to SEQ ID NO:1, for example, is at least about 80% identical to the entire sequence of SEQ ID NO:1, as opposed merely to subsequences thereof.

The term "plasmid" refers to a circular double-stranded (ds) DNA construct used as a cloning vector, and which forms an extrachromosomal self-replicating genetic element in some eukaryotes or prokaryotes, or integrates into the host chromosome.

A "production host" is a cell used to produce products. As disclosed herein, a production host is modified to express or overexpress selected genes, and/or to have attenuated expression of selected genes. Non-limiting examples of production hosts include plant, animal, human, bacteria, yeast, cyanobacteria, algae, and/or filamentous fungi cells.

A "promoter" is a polynucleotide sequence that functions to direct transcription of a downstream gene. In preferred embodiments, the promoter is appropriate to the host cell in which the target gene is being expressed. The promoter, together with other transcriptional and translational regula-tory polynucleotide sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

The terms "protein" and "polypeptide" are used inter-changeably herein. The 3-letter code as well as the 1-letter code for amino acid residues as defined in conformity with the IUPAC-IUB Joint Commission on Biochemical Nomen-clature (JCBN) is used throughout this disclosure. It is also understood that a polypeptide may be coded for by more than one polynucleotide sequence due to the degeneracy of the genetic code. An enzyme is a protein. The terms "amino acid sequence" and "polypeptide sequence" are used inter-changeably herein.

The terms "nucleic acid" and "polynucleotide" are used interchangeably herein.

The term "recombinant," when used to modify the term "cell" or "vector" herein, refers to a cell or a vector that has been modified by the introduction of a heterologous poly-nucleotide sequence, or that the cell is derived from a cell so modified. Thus, for example, recombinant cells express genes that are not found in identical form within the native (non-recombinant) form of the cells or express, as a result of deliberate human intervention, native genes that are other-wise abnormally expressed, underexpressed, or not expressed at all. The terms "recombinant," used with respect to proteins and nucleic acids refers to mutant proteins and nucleic acids, respectively.

The terms "regulatory segment," "regulatory sequence," or "expression control sequence" refer to a polynucleotide sequence that is operatively linked with another polynucle-otide sequence that encodes the amino acid sequence of a polypeptide chain to effect the expression of that encoded amino acid sequence. The regulatory sequence can inhibit, repress, promote, or even drive the expression of the oper-ably-linked polynucleotide sequence encoding the amino acid sequence.

The term "substantially identical," in the context of two polynucleotides or two polypeptides refers to a polynucle-otide or polypeptide that comprises at least 70% sequence identity, for example, at least 75%, at least 80%, at least 85%, at least 90%, at least 91%, at least 92%, at least 93%, at least 94%, at least 95%, at least 96%, at least 97%, at least 98%, or at least 99% sequence identity as compared to a reference sequence using the programs or algorithms (e.g., BLAST, ALIGN, CLUSTAL) using standard parameters..

"Substantially purified" means molecules that are at least about 60% free, preferably at least about 75% free, about 80% free, about 85% free, and more preferably at least about 90% free from other components with which they are naturally associated. As used herein, the term "purified" or "to purify" also refers to the removal of contaminants from a sample.

"Substitution" means replacing an amino acid in the sequence of a corresponding protein with another amino acid at a particular position, resulting in a mutant of the corresponding protein. The amino acid used as a substitute can be a naturally-occurring amino acid, or can be a syn-thetic or non-naturally-occurring amino acid.

The term "transformed" or "stably transformed" cell refers to a cell that has a non-native (heterologous) poly-nucleotide sequence integrated into its genome or as an episomal plasmid that is maintained for at least two genera-tions.

"Tryptamine analog" refers to tryptamine, substituted tryptamine, and any other product produced from decar-boxylating a tryptophan analog with a mutant tryptophan decarboxylase protein of the invention.

Figure 2:
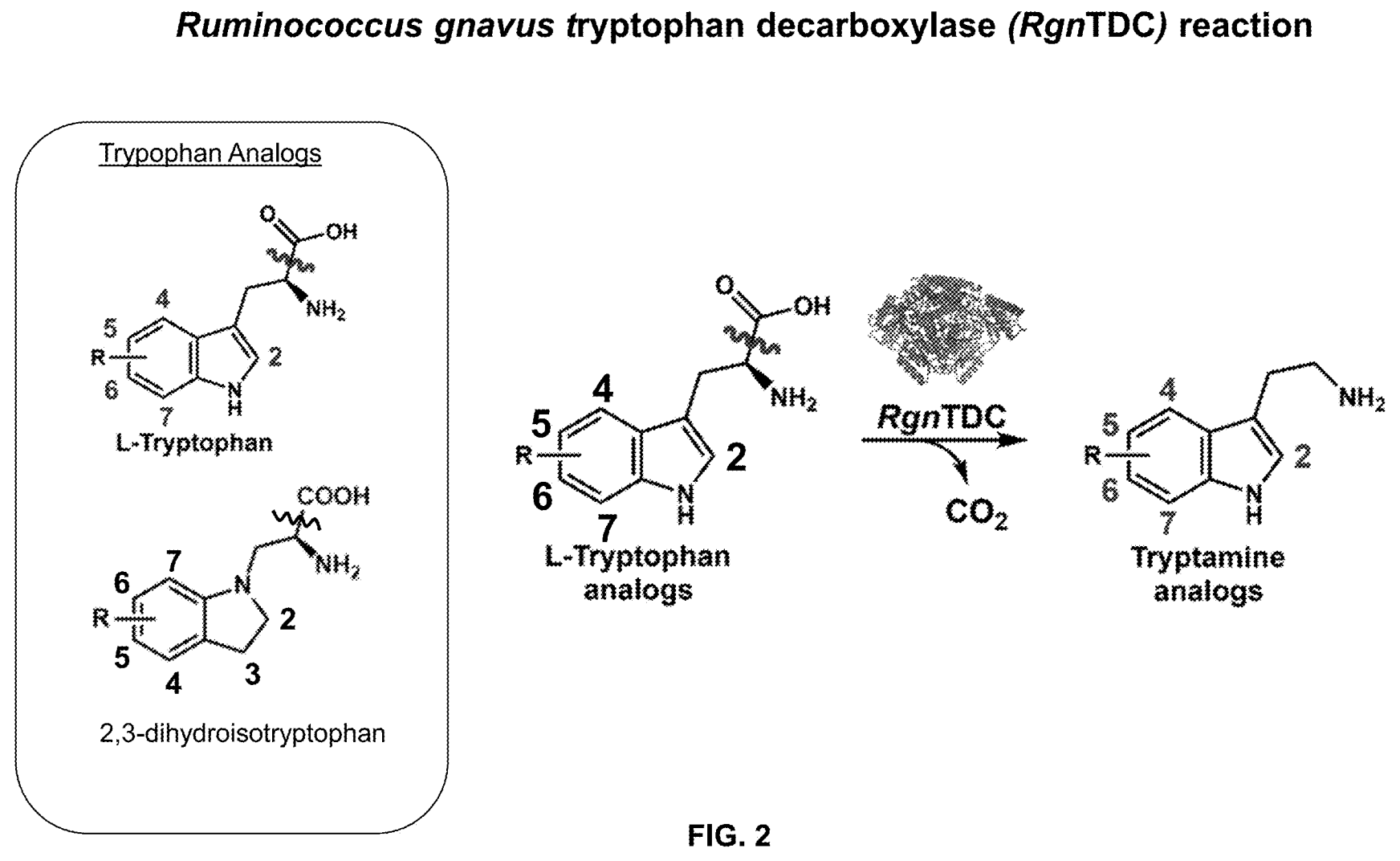

"Tryptophan analog" refers to tryptophan, substituted tryptophan, 2,3-dihydroisotryptophan, and substituted 2,3-dihydroisotryptophan (see FIG. 2 for exemplary tryptophan analogs, including tryptophan, 2,3-dihydroisotryptophan, and exemplary positions for substituting on same).

Figure 13:
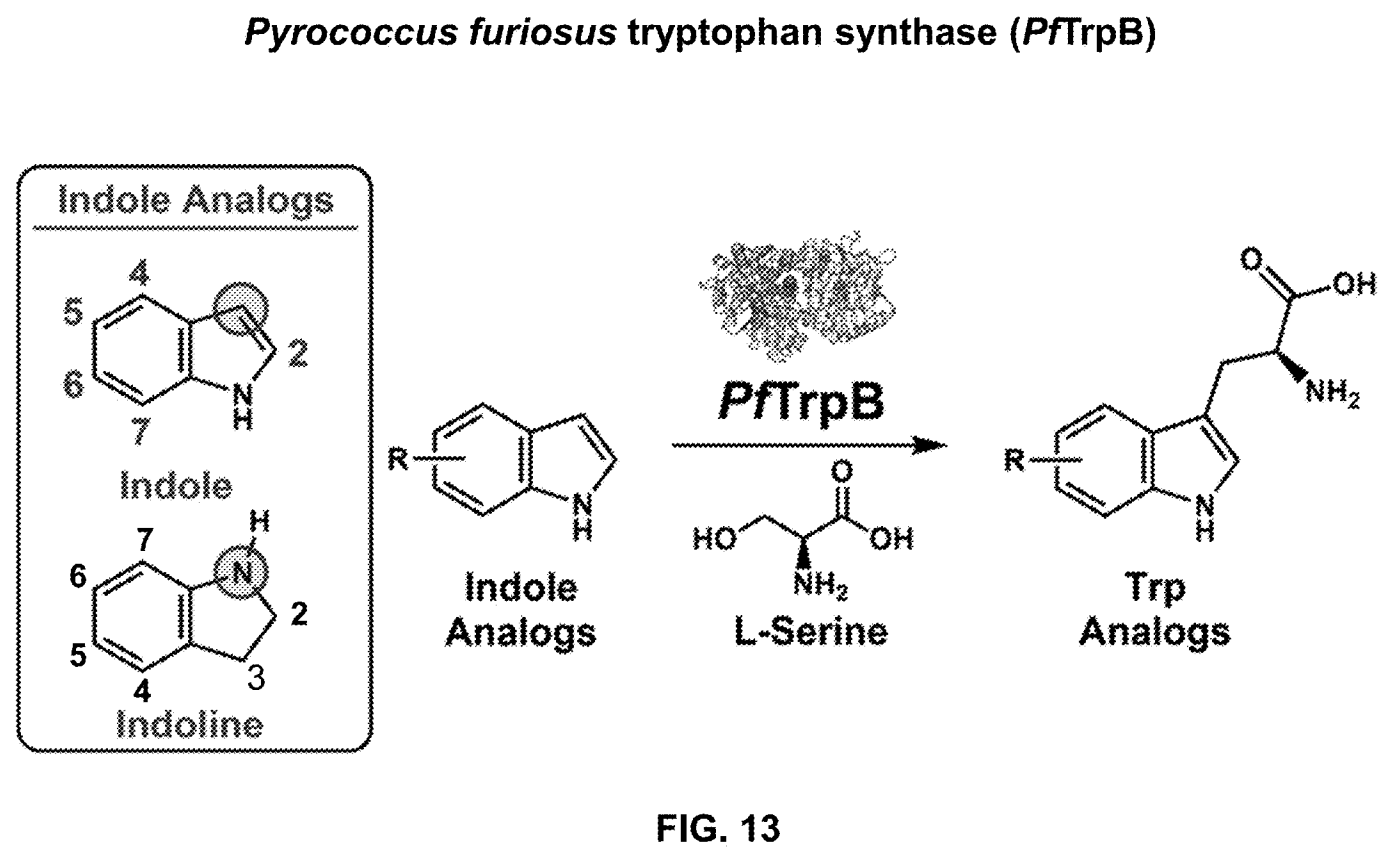

"Indole analog" refers to indole, substituted indole, indoline, and substituted indoline (see FIG. 13 for exemplary indole analogs, including indole and indoline and exemplary positions for substituting on same).

"Vector" refers to a polynucleotide construct designed to introduce polynucleotides into one or more cell types. Vectors include cloning vectors, expression vectors, shuttle vectors, plasmids, cassettes and the like. In some embodiments, the polynucleotide construct comprises a polynucleotide sequence encoding a mutant tryptophan decarboxylase protein that is operably linked to a suitable prosequence capable of effecting the expression of the polynucleotide or gene in a suitable host.

"Wild type" means, in the context of a gene or protein, a polynucleotide or protein sequence that occurs in nature. In some embodiments, the wild-type sequence refers to a sequence of interest that is a starting point for protein engineering. "Wild type" is used interchangeably with "native."

"Substituted tryptamine" refers to a tryptamine comprising one or more substituents at any one or more positions, such as at any one or more of the 2, 4, 5, 6, and 7 positions.

"Substituted tryptophan" refers to a tryptophan comprising one or more substituents at any one or more positions, such as at any one or more of the 2, 4, 5, 6, and 7 positions.

"Substituted 2,3-dihydroisotryptophan" refers to 2,3-dihydroisotryptophan comprising one or more substituents at any one or more positions, such as at any one or more of the 2, 3, 4, 5, 6, and 7 positions.

"Substituted indole" refers to indole comprising one or more substituents at any one or more positions, such as at any one or more of the 2, 4, 5, 6, and 7 positions.

"Substituted indoline" refers to indoline comprising one or more substituents at any one or more positions, such as at any one or more of the 2, 3, 4, 5, 6, and 7 positions.

"Substituent" refers to a moiety other than hydrogen.

In some versions, each of the one or more substituents on the substituted compounds described herein is independently halogen, optionally substituted alkyl, optionally substituted alkenyl, optionally substituted alkynyl, optionally substituted cycloalkyl, optionally substituted cycloalkenyl, hydroxyl, carboxyl, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group.

"Optionally substituted" is used interchangeably herein with "substituted or un substituted."

In some versions, each optionally substituted alkyl, optionally substituted alkyloxy, optionally substituted alkylthio, optionally substituted alkylsulfinyl, optionally substituted alkylsulfonyl, optionally substituted alkylsulfonyloxy, and optionally substituted alkyloxycarbonyl, when substituted, is independently substituted with one to three substituent(s) selected from the group consisting of cycloalkyl, alkylene optionally containing one or two heteroatom(s), hydroxy, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, aryl optionally substituted with a substituent group B at one to three position(s), heteroaryl optionally substituted with a substituent group C at one to three position(s), an optionally substituted non-aromatic heterocyclic ring group optionally substituted with a substituent group C at one to three position(s), aryloxy optionally substituted with a substituent group B at one to three position(s), and alkylsulfonyl.

In some versions, each optionally substituted alkenyl, optionally substituted alkynyl, optionally substituted alkenyloxy, optionally substituted alkynyloxy, optionally substituted alkenylthio, optionally substituted alkynylthio, optionally substituted alkenyloxycarbonyl, optionally substituted alkynyloxycarbonyl, optionally substituted cycloalkyl, optionally substituted cycloalkenyl, optionally substituted cycloalkyloxy, optionally substituted cycloalkenyloxy, optionally substituted cycloalkylthio, optionally substituted cycloalkenylthio, optionally substituted cycloalkylsulfinyl, optionally substituted cycloalkenylsulfinyl, optionally substituted cycloalkylsulfonyl, optionally substituted cycloalkenylsulfonyl, optionally substituted cycloalkylsulfonyloxy, optionally substituted cycloalkenylsulfonyloxy, and optionally substituted alkylene optionally containing one or two heteroatom(s), when substituted, is independently substituted with one or more substituent(s) selected from the group consisting of alkyl optionally substituted with a substituent group D at one to three position(s), cycloalkyl, hydroxy, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, acyloxy, aryl optionally substituted with a substituent group B at one to three position(s), heteroaryl optionally substituted with a substituent group C at one to three position(s), non-aromatic heterocyclic group optionally substituted with a substituent group C at one to three position(s), aryloxy optionally substituted with a substituent group C at one to three position(s), and alkylsulfonyl.

In some versions, each optionally substituted aryl, optionally substituted aryloxy, optionally substituted aryloxycarbonyl, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, and optionally substituted non-aromatic heterocyclic group, when substituted, are each independently substituted with one or more substituent(s) selected from the group consisting of alkyl optionally substituted with a substituent group D at one to three position(s), cycloalkyl, alkenyl, alkynyl, hydroxy, alkyloxy optionally substituted with a substituent group A at one to three position(s), aryloxy optionally substituted with a substituent group B at one to three position(s), mercapto, alkylthio, a halogen atom, nitro, cyano, carboxy, alkyloxycarbonyl, acyl, alkylsulfonyl, optionally substituted amino, optionally substituted carbamoyl, aryl optionally substituted with a substituent group B at one to three position(s), heteroaryl optionally substituted with a substituent group C at one to three position(s), and non-aromatic heterocyclic group optionally substituted with a substituent group C at one to three position(s).

In some versions, each optionally substituted amino, optionally substituted carbamoyl, and optionally substituted sulfamoyl, when substituted, is independently substituted with one or two substituent(s) selected from the group consisting of alkyl, alkenyl, alkynyl, cycloalkyl, cycloalkynyl, aryl, heteroaryl, acyl, alkyloxycarbonyl, alkenyloxycarbonyl, alkynyloxycarbonyl, alkyl sulfonyl, alkenylsulfonyl, alkynylsulfonyl, arylsulfonyl, and heteroarylsulfonyl.

Each substituent group A is independently selected from the group consisting of a halogen atom and phenyl optionally substituted with one to three substituent(s) selected from substituent group B.

Each substituent group B is independently selected from the group consisting of a halogen atom, alkyl, alkyloxy, cyano, and nitro.

Each substituent group C is independently selected from the group consisting of a halogen atom and alkyl.

Each substituent group D is independently selected from the group consisting of a halogen atom and alkyloxy.

In some versions, each of the one or more substituents on the substituted compounds described herein is independently halogen, unsubstituted alkyl, unsubstituted alkenyl, unsubstituted alkynyl, unsubstituted cycloalkyl, unsubstituted cycloalkenyl, hydroxyl, carboxyl, unsubstituted alkyloxy, unsubstituted alkenyloxy, unsubstituted alkynyloxy, unsubstituted cycloalkyloxy, unsubstituted cycloalkenyloxy, mercapto, unsubstituted alkylthio, unsubstituted alkenylthio, unsubstituted alkynylthio, unsubstituted alkylsulfinyl, unsubstituted alkylsulfonyl, unsubstituted alkylsulfonyloxy, unsubstituted cycloalkylthio, unsubstituted cycloalkylsulfinyl, unsubstituted cycloalkylsulfonyl, unsubstituted cycloalkylsulfonyloxy, unsubstituted cycloalkenylthio, unsubstituted cycloalkenylsulfinyl, unsubstituted cycloalkenylsulfonyl, unsubstituted cycloalkenylsulfonyloxy, unsubstituted amino, acyl, unsubstituted alkyloxycarbonyl, unsubstituted alkenyloxycarbonyl, unsubstituted alkynyloxycarbonyl, unsubstituted aryloxycarbonyl, unsubstituted carbamoyl, unsubstituted sulfamoyl, cyano, nitro, unsubstituted aryl, unsubstituted aryloxy, unsubstituted arylthio, unsubstituted arylsulfinyl, unsubstituted arylsulfonyl, unsubstituted arylsulfonyloxy, unsubstituted heteroaryl, unsubstituted heteroaryloxy, unsubstituted heteroarylthio, unsubstituted heteroarylsulfinyl, unsubstituted heteroarylsulfonyl, unsubstituted heteroarylsulfonyloxy, or an unsubstituted non-aromatic heterocyclic group.

In some versions, each of the one or more substituents on the substituted compounds described herein is independently halogen, unsubstituted C1-C6 alkyl, hydroxyl, carboxyl, unsubstituted C1-C6 alkyloxy, unsubstituted amino, acyl, unsubstituted alkyloxycarbonyl, unsubstituted carbamoyl, unsubstituted aryl, unsubstituted heteroaryl, or unsubstituted non-aromatic heterocyclic group.

In various versions, each of the one or more substituents on the substituted compounds described herein consists of no more than 30, no more than 25, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, no more than 5, no more than 4, no more than 3, no more than 2, no more than 1 covalently bonded atoms.

The term "halogen" refers to fluorine, chlorine, bromine, and iodine. Fluorine, chlorine, and bromine are preferred.

The term "hetero atom" refers to an oxygen atom, a sulfur atom, and a nitrogen atom.

The term "alkyl" includes a monovalent straight or branched hydrocarbon group having one to eight carbon atom(s). Examples include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, and the like. C1-C6 alkyl is preferred. C1-C4 alkyl or C1-C3 alkyl is further preferred. When a number of carbons is specified, it means "alkyl" having the carbon number within the range.

The term "alkenyl" includes a monovalent straight or branched hydrocarbon group having two to eight carbon atoms and one or more double bond(s). Examples include vinyl, allyl, 1-propenyl, 2-butenyl, 2-pentenyl, 2-hexenyl, 2-heptenyl, 2-octenyl, and the like. C2-C6 alkenyl is preferred. C2-C4 or C2-C3 alkenyl is further preferred.

The term "alkynyl" includes a monovalent straight or branched hydrocarbon group having two to eight carbon atoms and one or more triple bond(s). Examples include ethynyl, 1-propynyl, 2-propynyl, 2-butynyl, 2-pentynyl, 2-hexynyl, 2-heptynyl, 2-octynyl, and the like. C2-C6 alkynyl is preferred. C2-C4 or C2-C3 alkynyl is further preferred.

The term "cycloalkyl" includes a cycloalkyl having three to eight carbon atoms. Examples include cyclopropyl, cyclobutyl, cyclopentyl, cyclohexyl, cycloheptyl, cyclooctyl, and the like. C3-C6 cycloalkyl is preferred.

The term "cycloalkenyl" includes a cycloalkenyl having three to eight carbon atoms. Examples include cyclopropenyl, cyclobutenyl, cyclopentenyl, cyclohexenyl, cycloheptenyl, cyclooctenyl, and the like. C3-C6 cycloalkenyl is preferred.

The term "alkyloxy" includes a group wherein an oxygen atom is substituted with one "alkyl" as described herein. Examples include methyloxy, ethyloxy, n-propyloxy, isopropyloxy, n-butyloxy, isobutyloxy, sec-butyloxy, tert-butyloxy, n-pentyloxy, isopentyloxy, 2-pentyloxy, 3-pentyloxy, n-hexyloxy, isohexyloxy, 2-hexyloxy, 3-hexyloxy, n-heptyloxy, n-octyloxy, and the like. C1-C6 alkyloxy is preferred. C1-C4 alkyloxy or C1-C3 alkyloxy is further preferred. When a number of carbons is specified, it means "alkyloxy" having the carbon number within the range.

The term "alkenyloxy" includes a group wherein an oxygen atom is substituted with one "alkenyl" as described herein. Examples include vinyloxy, allyloxy, 1-propenyloxy, 2-butenyloxy, 2-pentenyloxy, 2-hexenyloxy, 2-heptenyloxy, 2-octenyloxy, and the like. C2-C6 alkenyloxy is preferred. Moreover, C2-C4 or C2-C3 alkenyloxy is further preferred. When a number of carbons is specified, it means "alkenyloxy" having the carbon number within the range.

The term "alkynyloxy" includes a group wherein an oxygen atom is substituted with one "alkynyl" as described herein. Examples include ethynyloxy, 1-propynyloxy, 2-propynyloxy, 2-butynyloxy, 2-pentynyloxy, 2-hexynyloxy, 2-heptynyloxy, 2-octynyloxy, and the like. C2-C6 alkynyloxy is preferred. C2-C4 or C2-C3 alkynyloxy is further preferred. When a number of carbons is specified, it means "alkynyloxy" having the carbon number within the range.

The term "cycloalkyloxy" includes a group wherein an oxygen atom is substituted with one "cycloalkyl" as described herein. Examples include cyclopropyloxy, cyclobutyloxy, cyclopentyloxy, cyclohexyloxy, cyclohepty-loxy, and cyclooctyloxy. C3-C6 cycloalkyloxy is preferred. When a number of carbons is specified, it means "cycloalkyloxy" having the carbon number within the range.

The term "cycloalkenyloxy" includes a group wherein an oxygen atom is substituted with one "cycloalkenyl" as described herein. Examples include cyclopropenyloxy, cyclobutenyloxy, cyclopentenyloxy, cyclohexenyloxy, cycloheptenyloxy, and cyclooctenyloxy. C3-C6 cycloalkenyloxy is preferred. When a number of carbons is specified, it means "cycloalkenyloxy" having the carbon number within the range.

The term "alkylthio" includes a group wherein a sulfur atom is substituted with one "alkyl" as described herein. Examples include methylthio, ethylthio, n-propylthio, isopropylthio, n-butylthio, isobutylthio, sec-butylthio, tert-butylthio, n-pentylthio, isopentylthio, 2-pentylthio, 3-pentylthio, n-hexylthio, isohexylthio, 2-hexylthio, 3-hexylthio, n-heptylthio, n-octylthio, and the like. C1-C6 Alkylthio is preferred. C1-C4 alkylthio is further preferred. C1-C3, C1-C2, or C1 alkylthio is further preferred. When a number of carbons is specified, it means "alkylthio" having the carbon number within the range.

The term "alkenylthio" includes a group wherein a sulfur atom is substituted with one "alkenyl" as described herein. Examples include vinylthio, allylthio, 1-propenylthio, 2-butenylthio, 2-pentenylthio, 2-hexenylthio, 2-heptenyl-thio, 2-octenylthio, and the like. C2-C6 Alkenylthio is preferred. C2-C4 or C2-C3 alkylthio is further preferred. When a number of carbons is specified, it means "alkenyl-thio" having the carbon number within the range.

The term "alkynylthio" includes a group wherein a sulfur atom is substituted with one "alkynyl" as described herein. Examples include ethynylthio, 1-propynylthio, 2-propynyl-thio, 2-butynylthio, 2-pentynylthio, 2-hexynylthio, 2-hepty-nylthio, 2-octynylthio, and the like. C2-C6 alkynylthio is preferred. C2-C4 or C2-C3 alkynylthio is further preferred. When a number of carbons is specified, it means "alkynyl-thio" having the carbon number within the range.

The term "alkylsulfinyl" includes a group wherein sulfinyl is substituted with one "alkyl" as described herein. Examples include methylsulfinyl, ethylsulfinyl, n-propy-lsulfinyl, isopropylsulfinyl, n-butylsulfinyl, isobutylsulfinyl, sec-butylsulfinyl, tert-butylsulfinyl, n-pentylsulfinyl, iso-pentylsulfinyl, 2-pentylsulfinyl, 3-pentylsulfinyl, n-hex-ylsulfinyl, isohexylsulfinyl, 2-hexylsulfinyl, 3-hexylsulfinyl, n-heptylsulfinyl, n-octylsulfinyl, and the like. C1-C6 alkylsulfinyl is preferred. C1-C4 or C1-C3 alkylsulfinyl is further preferred.

The term "alkylsulfonyl" includes a group wherein sulfonyl is substituted with one "alkyl" as described herein. Examples include methylsulfonyl, ethylsulfonyl, n-propy-lsulfonyl, isopropylsulfonyl, n-butylsulfonyl, isobutylsulfo-nyl, sec-butylsulfonyl, tert-butylsulfonyl, n-pentylsulfonyl, isopentylsulfonyl, 2-pentylsulfonyl, 3-pentylsulfonyl, n-hexylsulfonyl, isohexylsulfonyl, 2-hexylsulfonyl, 3-hex-ylsulfonyl, n-heptylsulfonyl, n-octylsulfonyl, and the like. C1-C6 alkylsulfonyl is preferred. C1-C4 or C1-C3 alkylsulfonyl is further preferred.

The term "alkylsulfonyloxy" includes a group wherein an oxygen atom is substituted with one "alkylsulfonyl" as described herein. Examples include methylsulfonyloxy, eth-ylsulfonyloxy, n-propylsulfonyloxy, isopropylsulfonyloxy, n-butylsulfonyloxy, isobutylsulfonyloxy, sec-butylsulfony-loxy, tert-butylsulfonyloxy, n-pentylsulfonyloxy, isopen-tylsulfonyloxy, 2-pentylsulfonyloxy, 3-pentylsulfonyloxy, n-hexylsulfonyloxy, isohexylsulfonyloxy, 2-hexylsulfony-loxy, 3-hexylsulfonyloxy, n-heptylsulfonyloxy, n-oc-tylsulfonyloxy, and the like. C1-C6 alkylsulfonyl is preferred. C1-C4 or C1-C3 alkylsulfonyl is further preferred.

The term "cycloalkylthio" includes a group wherein a sulfur atom is substituted with one "cycloalkyl" as described herein. Examples include cyclopropylthio, cyclobutylthio, cyclopentylthio, cyclohexylthio, cycloheptylthio, cyclooc-tylthio, and the like. C3-C6 cycloalkylthio is preferred. When a number of carbons is specified, it means "cycloal-kylthio" having the carbon number within the range.

The term "cycloalkylsulfinyl" includes a group in which sulfinyl is substituted with one "cycloalkyl" as described herein. Examples include cyclopropylsulfinyl, cyclobu-tylsulfinyl, cyclopentylsulfinyl, cyclohexylsulfinyl, cyclo-heptylsulfinyl, and cyclooctylsulfinyl. Preferably C3-C6 cycloalkylsulfinyl.

The term "cycloalkylsulfonyl" includes a group in which sulfonyl is substituted with one "cycloalkyl" as described herein. Examples include cyclopropylsulfonyl, cyclobu-tylsulfonyl, cyclopentylsulfonyl, cyclohexylsulfonyl, cyclo-heptylsulfonyl, and cyclooctylsulfonyl. C3-C6 cycloal-kylsulfonyl is preferred.

The term "cycloalkylsulfonyloxy" includes a group in which an oxygen atom is substituted with one "cycloal-kylsulfonyl" as described herein. Examples include cyclo-propylsulfonyloxy, cyclobutylsulfonyloxy, cyclopentyl sulfonyloxy, cyclohexyl sulfonyloxy, cycloheptylsulfony-loxy, and cyclooctylsulfonyloxy. C6-C3 cycloalkylsulfony-loxy is preferred.

The term "cycloalkenylthio" includes a group in which a sulfur atom is substituted with one "cycloalkenyl" as described herein. Examples include cyclopropenylthio, cyclobutenylthio, cyclopentenylthio, cyclohexenylthio, cycloheptenylthio, and cyclooctenylthio. C3-C6 cycloalk-enylthio is preferred. When a number of carbons is specified, it means "cycloalkenylthio" having the carbon number within the range.

The term "cycloalkenylsulfinyl" includes a group in which sulfinyl is substituted with one "cycloalkenyl" as described herein. Examples include cyclopropenylsulfinyl, cyclobutenylsulfinyl, cyclopentenylsulfinyl, cyclohex-enylsulfinyl, cycloheptenylsulfinyl, and cyclooctenylsulfi-nyl. C3-C6 cycloalkenylsulfinyl is preferred.

The term "cycloalkenylsulfonyl" includes a group in which sulfonyl is substituted with one "cycloalkenyl" as described herein. Examples include cyclopropenylsulfonyl, cyclobutenylsulfonyl, cyclopentenylsulfonyl, cyclohex-enylsulfonyl, cycloheptenylsulfonyl, and cyclooctenylsulfo-nyl. Preferably C3-C6 cycloalkenylsulfonyl is preferred.

The term "cycloalkenylsulfonyloxy" includes a group in which an oxygen atom is substituted with one "cycloalk-enylsulfonyl" described as described herein. Examples include cyclopropenylsulfonyloxy, cyclobutenylsulfony-loxy, cyclopentenylsulfonyloxy, cyclohexenylsulfonyloxy, cycloheptenylsulfonyloxy, and cyclooctenylsulfonyloxy. C3-C6 cycloalkenylsulfonyloxy is preferred.

The term "alkyloxycarbonyl" includes a group in which carbonyl is substituted with one "alkyloxy" as described herein. Examples include methyloxycarbonyl, ethyloxycarbonyl, n-propyloxycarbonyl, isopropyloxycarbonyl, n-butyloxycarbonyl, tert-butyloxycarbonyl, and n-pentyloxycarbonyl. C1-C6, C1-C4, or C1-C3 alkyloxycarbonyl is preferred. C1-C2 alkyloxycarbonyl is further preferred.

The term "alkenyloxycarbonyl" includes a group in which carbonyl is substituted with one "alkenyloxy" as described herein. Examples include vinyloxycarbonyl, allyloxycarbonyl, 1-propenyloxycarbonyl, 2-butenyloxycarbonyl, and 2-pentenyloxyarbonyl. C2-C6, C2-C4, or C2-C3 alkyloxycarbonyl is preferred.

The term "alkynyloxycarbonyl" includes a group in which carbonyl is substituted with one "alkynyloxy" as described herein. Examples include ethynyloxycarbonyl, 1-propynyloxycarbonyl, 2-propynyloxycarbonyl, 2-butynyloxyarbonyl, and 2-pentynyloxycarbonyl. C2-C6, C2-C4, or C2-C3 alkynyloxycarbonyl is preferred.

The term "acyl" includes alkylcarbonyl wherein the part of alkyl is "alkyl" as described herein, alkenylcarbonyl wherein the part of alkenyl is "alkenyl" as described herein, alkynylcarbonyl wherein the part of alkynyl is "alkynyl" as described herein, cycloalkylcarbonyl wherein the part of cycloalkyl is "cycloalkyl" as described herein, arylcarbonyl wherein the part of aryl is "aryl" as described herein, heteroarylcarbonyl wherein the part of heteroaryl is "heteroaryl" as described herein, and non-aromatic heterocyclo-carbonyl wherein the part of non-aromatic heterocyclic group is "non-aromatic heterocyclic group" as described herein. "Alkyl," "alkenyl," "alkynyl," "cycloalkyl," "aryl," "heteroaryl," and "non-aromatic heterocyclic group" may be substituted respectively with substituent groups exemplified in "optionally substituted alkyl," "optionally substituted alkenyl," "optionally substituted alkynyl," "optionally substituted cycloalkyl," "optionally substituted aryl," "optionally substituted heteroaryl," and "optionally substituted non-aromatic heterocyclic group" as described herein. Examples of the acyl group include acetyl, propionyl, butyroyl, cyclohexylcarbonyl, benzoyl, pyridinecarbonyl, and the like.

The term "optionally substituted amino" includes an amino group which may be substituted with one or two group(s) of "alkyl" as described herein, "alkenyl" as described herein, "alkynyl" as described herein, "cycloalkyl" as described herein, "cycloalkynyl" as described herein, "aryl" as described herein, "heteroaryl" as described herein, "acyl" as described herein, "alkyloxycarbonyl" as described herein, "alkenyloxycarbonyl" as described herein, "alkynyloxycarbonyl" as described herein, "alkyl sulfonyl," "alkenyl sulfonyl," "alkynyl sulfonyl," "aryl sulfonyl," and/or "heteroaryl sulfonyl" as described herein. Examples of the optionally substituted amino group include amino, methylamino, dimethylamino, ethylamino, diethylamino, ethylmethylamino, benzylamino, acetylamino, benzoylamino, methyloxycarbonylamino, and methanesulfonylamino. Amino, methylamino, dimethylamino, ethylmethylamino, diethylamino, acetylamino, and methanesulfonylamino are preferred.

The term "optionally substituted carbamoyl" includes an aminocarbonyl group wherein the part of optionally substituted amino is "optionally substituted amino" as described herein. Examples of the optionally substituted carbamoyl group includes carbamoyl, N-methylcarbamoyl, N,N-dimethylcarbamoyl, N-ethyl-N-methylcarbamoyl, N,N-diethylcarbamoyl, N-phenylcarbamoyl, N-benzylcarbamoyl, N-acetylcarbamoyl, and N-methylsulfonylcarbamoyl etc. Carbamoyl, N-methylcarbamoyl, N,N-dimethylcarbamoyl, and N-methylsulfonylcarbamoyl etc. are preferred.

The term "optionally substituted sulfamoyl" includes an aminosulfonyl group wherein the part of optionally substituted amino is "optionally substituted amino" as described herein. Examples of the optionally substituted sulfamoyl group include sulfamoyl, N-methylsulfamoyl, N,N-dimethylsulfamoyl, N-ethyl-N-methyl sulfamoyl, N,N-diethylsulfamoyl, N-phenylsulfamoyl, N-benzylsulfamoyl, N-acetylsulfamoyl, and N-methylsulfonylsulfamoyl etc. Sulfamoyl, N-methylsulfamoyl, N,N-dimethylsulfamoyl, and N-methylsulfonylsulfamoyl etc. are preferred.

The term "alkylene" means a straight or branched alkylene group having one to eight carbon atom(s). Examples include methylene, ethylene, 1-methylethylene, trimethylene, 1-methyltrimethylene, pentamethylene, hexamethylene, and the like. C1-C4 or C1-3 alkylenes are preferred. C1-C2 or C1 alkylene is further preferred.

The term "aryl" includes an aromatic monocyclic or aromatic fused cyclic hydrocarbons. It may be fused with "cycloalkyl" as described herein, "cycloalkenyl" as described herein or "non-aromatic heterocyclic group" as described herein at any possible position. Both of monocyclic ring and fused ring may be substituted at any position. Examples include phenyl, 1-naphthyl, 2-naphthyl, anthryl, tetrahydronaphthyl, 1,3-benzodioxolyl, 1,4-benzodioxanyl etc. Phenyl, 1-naphthyl, and 2-naphthyl are preferred. Phenyl is further preferred.

The term "non-aromatic heterocyclic group" includes a 5- to 7-membered non-aromatic heterocyclic ring containing one or more of heteroatom(s) selected independently from oxygen, sulfur, and nitrogen atoms or a multicyclic ring formed by fusing the two or more rings thereof. Examples include pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidyl (e.g., piperidino, 2-piperidyl), piperazinyl (e.g., 1-piperazinyl), indolinyl (e.g., 1-indolinyl), isoindolinyl (e.g., isoindolinyl), morpholinyl (e.g., morpholino, 3-morpholinyl) etc.

The term "heteroaryl" includes a 5- to 6-membered aromatic ring containing one or more of heteroatom(s) selected independently from oxygen, sulfur, and nitrogen atoms. It may be fused with "cycloalkyl" as described herein, "aryl" as described herein, "non-aromatic heterocyclic group" as described herein, or other heteroaryl at any possible position. The heteroaryl group may be substituted at any position whenever it is a monocyclic ring or a fused ring. Examples include pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), thiadiazolyl (e.g., 1,3,4-thiadiazolyl), indolidinyl (e.g., 2-indolidinyl, 6-indolidinyl), isoindolynyl (e.g., 2-isoindolynyl), indolyl (e.g., 1-indolyl, 2-indolyl, 3-indolyl), indazolyl (e.g., 3-indazolyl), purinyl (e.g., 8-purinyl), quinolidinyl (e.g., 2-quinolidinyl), isoquinolyl (e.g., 3-isoquinolyl), quinolyl (e.g., 2-quinolyl, 5-quinolyl), phtharazinyl (e.g., 1-phtharazinyl), naphthylidinyl (e.g., 2-naphthylidinyl), quinolanyl (e.g., 2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzoimidazolyl (e.g., 2-benzo-imidazolyl), benzoisoxazolyl (e.g., 3-benzoisoxazolyl), ben-zooxazolyl (e.g., 2-benzooxazolyl), benzooxadiazolyl (e.g., 4-benzooxadiazolyl), benzoisothiazolyl (e.g., 3-benzoisothi-azolyl), benzothiazolyl (e.g., 2-benzothiazolyl), benzofuryl (e.g., 3-benzofuryl), benzothienyl (e.g., 2-benzothienyl), dibenzothienyl (e.g., 2-dibenzothienyl), and benzodioxolyl (e.g., 1,3-benzodioxolyl), etc.

The term "aryloxy" includes a group in which an oxygen atom is substituted with one "aryl" as described herein. Examples include phenyloxy and naphthyloxy, etc.

The term "arylthio" includes a group in which a sulfur atom is substituted with one "aryl" as described herein. Examples include phenylthio and naphthylthio, etc.

The term "arylsulfinyl" includes a group in which sulfinyl is substituted with one "aryl" as described herein. Examples include phenylsulfinyl and naphthylsulfinyl, etc.

The term "arylsulfonyl" includes a group in which sulfo-nyl is substituted with one "aryl" as described herein. Examples include phenylsulfonyl and naphthylsulfoinyl, etc.

Examples of "arylsulfonyloxy" include phenylsulfony-loxy and naphthylsulfonyloxy, etc.

The term "aryloxycarbonyl" includes a group in which carbonyl is substituted with one "aryloxy" as described herein. Examples include phenyloxycarbonyl, 1-naphth-yloxycarbonyl and 2-naphthyloxycarbonyl, etc.

The term "heteroaryloxy" includes a group in which an oxygen atom is substituted with one "heteroaryl" as described herein. Examples include pyrrolyloxy, furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy, pyridazinyloxy, tetrazoly-loxy, oxadiazolyloxy, thiadiazolyloxy, indolidinyloxy, isoin-dolynyloxy, indolyloxy, indazolyloxy, purinyloxy, quinolidi-nyloxy, isoquinolyloxy, quinolyloxy, phtharazinyloxy, naphthylidinyloxy, quinolanyloxy, quinazolinyloxy, cinnoli-nyloxy, pteridinyloxy, carbazolyloxy, phenanthridinyloxy, acridinyloxy, dibenzofuranyloxy, benzoimidazolyloxy, ben-zoisoxazolyloxy, benzooxazolyloxy, benzooxadiazolyloxy, benzoisothiazolyloxy, benzothiazolyloxy, benzofuryloxy, benzothienyloxy, dibenzothienyloxy, and benzodioxolyloxy. Preferably furyloxy, thienyloxy, imidazolyloxy, pyrazoly-loxy, isothiazolyloxy, isoxazolyloxy, oxazolyloxy, thiazoly-loxy, pyridyloxy, pyrazinyloxy, pyrimidinyloxy, and pyridazinyloxy, etc.

The term "heteroarylthio" includes a group in which a sulfur atom is substituted with one "heteroaryl" as described herein. Examples include pyrrolylthio, furylthio, thienylthio, imidazolylthio, pyrazolylthio, isothiazolylthio, isoxazolyl-thio, oxazolylthio, thiazolylthio, pyridylthio, pyrazinylthio, pyrimidinylthio, pyridazinylthio, tetrazolylthio, oxadiaz-olylthio, thiadiazolylthio, indolidinylthio, isoindolynylthio, indolylthio, indazolylthio, purinylthio, quinolidinylthio, iso-quinolylthio, quinolylthio, phtharazinylthio, naphthylidinyl-thio, quinolanylthio, quinazolinylthio, cinnolinylthio, pte-ridinylthio, carbazolylthio, phenanthridinylthio, acridinylthio, dibenzofuranylthio, benzoimidazolylthio, benzoisoxazolylthio, benzooxazolylthio, benzooxadiazolyl-thio, benzoisothiazolylthio, benzothiazolylthio, benzofuryl-thio, benzothienylthio, dibenzothienylthio, and benzodiox-olylthio, etc. Preferably furylthio, thienylthio, imidazolylthio, pyrazolylthio, isothiazolylthio, isoxazolyl-thio, oxazolylthio, thiazolylthio, pyridylthio, pyrazinylthio, pyrimidinylthio, and pyridazinylthio, etc.

The term "heteroarylsulfinyl" includes a group in which sulfinyl is substituted with one "heteroaryl" as described herein. Examples include pyrrolylsulfinyl, furylsulfinyl, thienylsulfinyl, imidazolylsulfinyl, pyrazolylsulfinyl, isothi-azolylsulfinyl, isoxazolylsulfinyl, oxazolylsulfinyl, thiaz-olylsulfinyl, pyridylsulfinyl, pyrazinylsulfinyl, pyrimidi-nylsulfinyl, pyridazinylsulfinyl, tetrazolylsulfinyl, oxadiazolylsulfinyl, thiadiazolylsulfinyl, indolidinylsulfinyl, isoindolylsulfinyl, indolylsulfinyl, indazolylsulfinyl, puri-nylsulfinyl, quinolidinylsulfinyl, isoquinolylsulfinyl, qui-nolylsulfinyl, phtharazinylsulfinyl, naphthylidinylsulfinyl, quinolanylsulfinyl, quinazolinylsulfinyl, cinnolinylsulfinyl, pteridinylsulfinyl, carbazolylsulfinyl, phenanthridinylsulfi-nyl, acridinylsulfinyl, dibenzofuranylsulfinyl, benzoimida-zolylsulfinyl, benzoisoxazolylsulfinyl, benzooxazolylsulfi-nyl, benzooxadiazolylsulfinyl, benzoisothiazolylsulfinyl, benzothiazolylsulfinyl, benzofurylsulfinyl, benzothie-nylsulfinyl, dibenzothienylsulfinyl, and benzodioxolylsulfi-nyl. Furylsulfinyl, thienylsulfinyl, imidazolylsulfinyl, pyra-zolylsulfinyl, isothiazolylsulfinyl, isoxazolylsulfinyl, oxazolylsulfinyl, thiazolylsulfinyl, pyridylsulfinyl, pyrazi-nylsulfinyl, pyrimidinylsulfinyl, and pyridazinylsulfinyl are preferred.

The term "heteroarylsulfonyl" includes a group in which sulfonyl is substituted with one "heteroaryl" as described herein. Examples include pyrrolylsulfonyl, furylsulfonyl, thienylsulfonyl, imidazolylsulfonyl, pyrazolylsulfonyl, iso-thiazolylsulfonyl, isoxazolylsulfonyl, oxazolylsulfonyl, thi-azolylsulfonyl, pyridylsulfonyl, pyrazinylsulfonyl, pyrim-idinylsulfonyl, pyridazinylsulfonyl, tetrazolylsulfonyl, oxadiazolylsulfonyl, thiadiazolylsulfonyl, indolizinylsulfo-nyl, isoindolylsulfonyl, indolylsulfonyl, indazolylsulfonyl, purinylsulfonyl, quinolidinylsulfonyl, isoquinolylsulfonyl, quinolylsulfonyl, phtharazinylsulfonyl, naphthilidinylsulfo-nyl, quinolanylsulfonyl, quinazolinylsulfonyl, cinnolinyl sulfonyl, pteridinyl sulfonyl, carbazolylsulfonyl, phenanthridinylsulfonyl, acridinylsulfonyl, dibenzofura-nylsulfonyl, benzoimidazolylsulfonyl, benzoisoxa-zolylsulfonyl, benzooxazolylsulfonyl, benzooxadiaz-olylsulfonyl, benzoisothiazolylsulfonyl, benzothia-zolylsulfonyl, benzofurylsulfonyl, benzothienylsulfonyl, dibenzothienylsulfonyl, and benzodioxolylsulfonyl, etc. Furylsulfonyl, thienylsulfonyl, imidazolylsulfonyl, pyra-zolylsulfonyl, isothiazolylsulfonyl, isoxazolylsulfonyl, oxa-zolylsulfonyl, thiazolylsulfonyl, pyridylsulfonyl, pyrazi-nylsulfonyl, pyrimidinylsulfonyl, and pyridazinylsulfonyl are preferred.

The term "heteroarylsulfonyloxy" includes a group in which an oxygen atom is substituted with one "heteroar-ylsulfonyl" as described herein. Examples include pyrro-lylsulfonyloxy, furylsulfonyloxy, thienylsulfonyloxy, imida-zolylsulfonyloxy, pyrazolylsulfonyloxy, isothiazol-ylsulfonyloxy, isoxazolylsulfonyloxy, oxazolylsulfonyloxy, thiazolylsulfonyloxy, pyridylsulfonyloxy, pyrazinylsulfony-loxy, pyrimidinylsulfonyloxy, pyridazinylsulfonyloxy, tetra-zolylsulfonyloxy, oxadiazolylsulfonyloxy, thiadiaz-olylsulfonyloxy, indolizinylsulfonyloxy, isoindolyl-sulfonyloxy, indolylsulfonyloxy, indazolylsulfonyloxy, puri-nylsulfonyloxy, quinolidinylsulfonyloxy, isoquinolylsulfo-nyloxy, quinolylsulfonyloxy, phtharazinylsulfonyloxy, naphthilidinylsulfonyloxy, quinolanyl sulfonyloxy, qui-nazolinylsulfonyloxy, cinnolinylsulfonyloxy, pteridi-nylsulfonyloxy, carbazolylsulfonyloxy, phenanthridi-nylsulfonyloxy, acridinylsulfonyloxy, dibenzofura-nylsulfonyloxy, benzoimidazolylsulfonyloxy, benzoisoxa-zolylsulfonyloxy, benzooxazolylsulfonyloxy, benzooxadiaz-olylsulfonyloxy, benzoisothiazolylsulfonyloxy, benzothiaz-olylsulfonyloxy, benzofuryl sulfonyloxy, benzo-thienylsulfonyloxy, dibenzothienylsulfonyloxy, and benzodioxolylsulfonyloxy, etc. Furylsulfonyloxy, thienylsulfonyloxy, imidazolylsulfonyloxy, pyrazolylsulfonyloxy, isothiazolylsulfonyloxy, isoxazolylsulfonyloxy, oxazolylsulfonyloxy, thiazolylsulfonyloxy, pyridylsulfonyloxy, pyrazinylsulfonyloxy, pyrimidinylsulfonyloxy, and pyridazinylsulfonyloxy are preferred.

The term "aromatic carbocyclic ring" includes an aromatic monocyclic or aromatic fused carbocyclic ring. Examples include a benzene ring, a naphthalene ring, and an anthracene ring. A benzene ring is preferred.

The term "aromatic heterocyclic ring" includes an aromatic monocyclic or aromatic fused heterocyclic ring. Examples include a pyrrole ring, a furan ring, a thiophen ring, a pyrazole ring, an imidazole ring, an isothiazole ring, an isoxazole ring, an oxazole ring, a thiazole ring, a pyrazine ring, a pyrimidine ring, a pyridazine ring, a tetrazole ring, an oxadiazole ring, a thiadiazole ring, an indolizine ring, an isoindole ring, an indole ring, an indazole ring, a purine ring, a quinolidine ring, an isoquinoline ring, a quinoline ring, a phtharazine ring, a naphthyridine ring, a quinolane ring, a quinazoline ring, a cinnoline ring, a pteridine ring, a carbazole ring, a phenanthridine ring, an acridine ring, a dibenzofuran ring, a benzimidazole ring, a benzisoxazole ring, a benzoxazole ring, a benzoxadiazole ring, a benzisothiazole ring, a benzothiazole ring, a benzofuran ring, a benzothiophene ring, a dibenzothiophene ring, and a benzodixolane ring are exemplified. Preferably a pyridine ring, a furan ring, and a thiophen ring are exemplified.

The term "C1-C6 alkylene" includes a straight or branched alkylene group having one to six carbon atom(s). Examples include $-CH_2-$, $-CH(CH_3)-$, $-C(CH_3)_2-$, $-CH_2CH_2-$, $-CH(CH_3)CH_2-$, $-C(CH_3)_2CH_2-$, $-CH_2CH_2CH_2-$, $-CH_2CH_2CH_2CH_2-$, $-CH_2CH_2CH_2CH_2-$, and $-CH_2CH_2CH_2CH_2CH_2CH_2-$. Preferred are $-CH_2-$, $-CH_2CH_2-$, $-CH_2CH_2CH_2-$, and $-CH_2CH_2CH_2CH_2-$.

The term "alkylene optionally containing one or two heteroatom(s)" of "optionally substituted alkylene optionally containing one or two heteroatom(s)" includes a straight or branched alkylene group having one to six carbon atoms, optionally containing one or two heteroatom(s) which may be substituted with "alkyl" as described herein. Examples include $-CH_2-$, $-CH(CH_3)-$, $-C(CH_3)_2-$, $-CH_2CH_2-$, $-CH_2CH_2CH_2-$, $-CH_2CH_2CH_2CH_2-$, $-CH_2CH_2CH_2CH_2O-$, $-CH_2CH_2CH_2CH_2CH_2-$, $-CH_2O-$, $-OCH_2-$, $-CH_2CH_2O-$, $-OCH_2CH_2-$, $-CH_2S-$, $-SCH_2-$, $-CH_2CH_2S-$, $-SCH_2CH_2-$, $-CH_2CH_2OCH_2CH_2-$, $-OCH_2CH_2O-$, $-OCH_2O-$, $-NHCH_2-$, $-N(CH_3)CH_2-$, $-N^+(CH_3)_2CH_2-$, $-NHCH_2CH_2CH_2-$, and $-N(CH_3)CH_2CH_2CH_2-$, etc. Preferred are $-CH_2-$, $-CH_2CH_2-$, $-CH_2CH_2CH_2-$, $-CH_2CH_2CH_2CH_2-$, $-OCH_2CH_2O-$, $-OCH_2O-$, and $-N(CH_3)CH_2CH_2CH_2-$.

The term "alkenylene optionally containing one or two heteroatom(s)" of "optionally substituted alkenylene optionally containing one or two heteroatom(s)" includes a straight or branched alkenylene group having two to six carbon atoms, optionally containing one or two heteroatom(s) which may be substituted with "alkyl" as described herein. Examples include $-CH=CHCH=CH-$, $-CH=CHO-$, $-OCH=CH-$, $-CH=CHS-$, $-SCH=CH-$, $-CH=CHNH-$, $-NHCH=CH-$, $-CH=CH-CH=N-$, and $-N=CH-CH=CH-$. Preferred are, $-CH=CHCH=CH-$, $-CH=CHCH=N-$, and $-N=CHCH=CH-$.

The term "alkynylene optionally containing one or two heteroatom(s)" includes a straight or branched alkynylene group having two to six carbon atoms, optionally containing one or two heteroatom(s) which may be substituted with "alkyl" as described herein. Examples include $-C\equiv CCH_2-$, $-CH_2C\equiv CCH_2-$, $-CH_2C\equiv CCH_2O-$, $-OCH_2C\equiv CH-$, $-CH_2C\equiv CCH_2S-$, $-SCH_2C\equiv CH-$, $-CH_2C\equiv CCH_2NH-$, $-NHCH_2C\equiv CH-$, $-CH_2C\equiv CCH_2N(CH_3)-$, and $-N(CH_3)CH_2C\equiv CH-$. Especially, $-CH_2C\equiv CCH_2-$, and $-OCH_2C\equiv CH-$ are preferred.

The term "3- to 8-membered nitrogen-containing non-aromatic heterocyclic ring" includes a ring of any of the formulas described as such in U.S. Pat. No. 8,143,285, which is incorporated herein by reference in its entirety.

The term "3- to 8-nitrogen-containing aromatic heterocyclic ring" includes a 3- to 8-membered aromatic heterocyclic ring containing one or more of nitrogen atom(s), and further optionally an oxygen atom and/or sulfur atom in the ring. Examples include pyrrolyl (e.g., 1-pyrrolyl, 2-pyrrolyl, 3-pyrrolyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), and thiadiazolyl (e.g., 1,3,4-thiadiazolyl).

The term "4- to 8-membered nitrogen-containing heterocyclic ring containing one or two nitrogen atom(s)" means a ring of any of the formulas described as such in U.S. Pat. No. 8,143,285, which is incorporated herein by reference in its entirety.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Summary

Enzymatic cascades are desirable in synthetic methodologies for their abilities to efficiently generate products under mild conditions, without need for purification of intermediate. However, promiscuous cascades that can synthesize a range of products are challenging to develop because they require catalysts with complementary substrate scopes. Standard protein engineering methods screen mutant libraries for activity on a single substrate and often lead to biocatalysts with limited or poorly characterized substrate scopes, hindering the development of promiscuous biocatalytic cascades. We use an innovative engineering approach to identify mutations that provide broad increases in activity with diverse substituted substrates called Substrate Multiplexed Screening (SUMS). Instead of screening for activity on a single substrate, SUMS allows multiple substrates to compete for the enzyme active site and we analyze the product distribution to discern how mutation changes both the activity and the promiscuity of the catalyst.

The following examples focus at least in part on L-tryptophan (Trp) decarboxylase (TDC), an enzyme that catalyzes the decarboxylation of Trp to form tryptamine. Tryptamines are desirable synthons of highly bioactive pharmacophores, and their formation is a committed step in biosynthesis of indole alkaloids. We investigated the TDC from *Ruminococcus gnavus* (RgnTDC), an enzyme that natively catalyzes the decarboxylation of Trp to form tryptamine (FIG. 2). RgnTDC is an exceptional decarboxylase with many Trp analogs but struggles with the highly bioactive 4- and 5-substituted substrates. Such poor activity with non-native substrates is a recurring limitation among biocatalysts. To overcome this limitation, we sought to engineer RgnTDC to improve its substrate scope.

Our engineering approach identified several important observations. Mutations at W349 improve activity with 5-substituted tryptophans. Many mutations at L355 greatly increase activity with 4-substituted Trps. Notably, L355A is activating for bulkier substrates, such as 4-CN-Trp and 4-OMe-Trp. F98V and F98M increase activity with 2- and 6-substituted Trps. L339V and V99A are activating for 2- and 4-substituted Trps.

Figure 3:
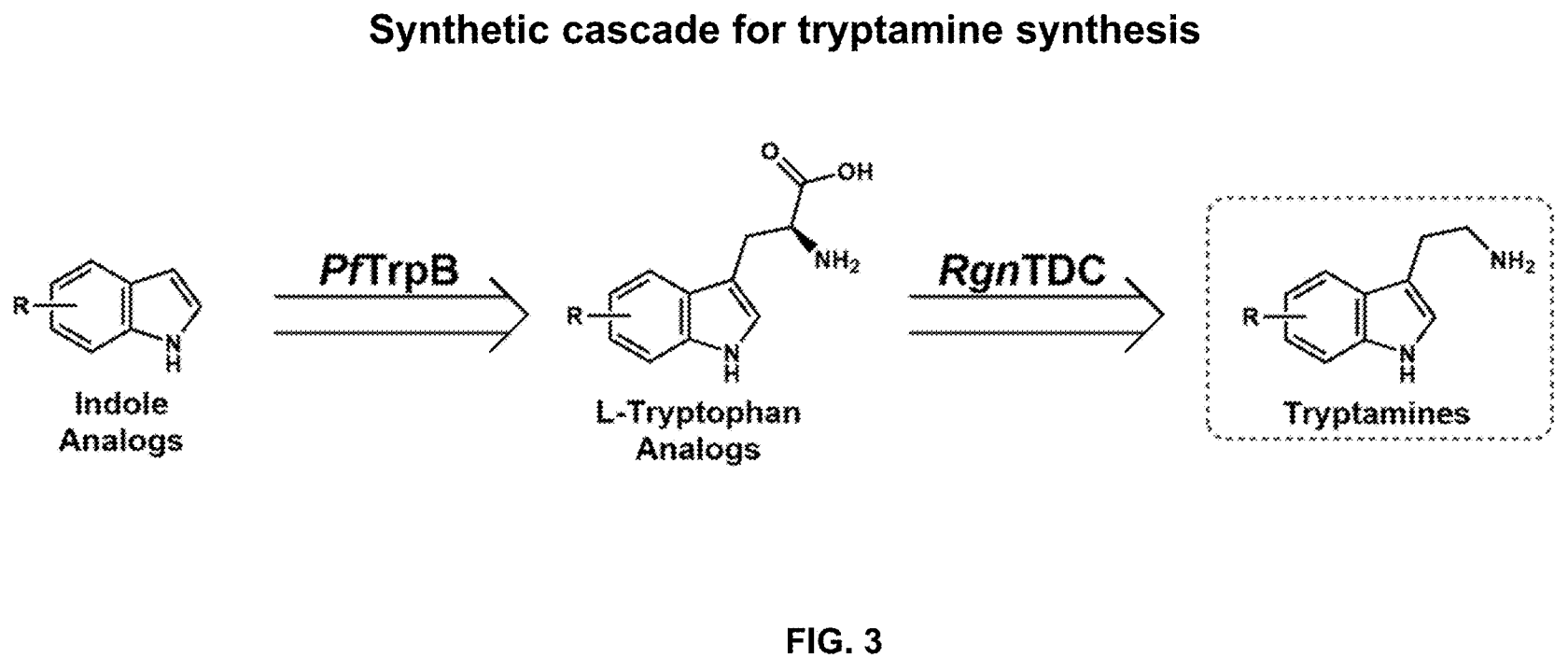

In addition to engineering RgnTDC, we engineer biocatalytic cascades to produce pharmacologically active substituted tryptamines (FIG. 3), Background Biocatalysts are prized for their ability to perform well-defined transformations. However, the use of enzymes in practical chemical synthesis is often hampered by their small or poorly understood substrate scopes.[1] The limitations of a narrow substrate scope are compounded if multiple enzymes are used in concert.[2-4] When the goal of research is to produce a chemically diverse array of products, each enzyme must have a complementary substrate scope to access the intended products. Using traditional protein engineering approaches, activity can readily be increased on a model compound.[5-7] Recent advances in both smart library design[8-11] and screening speed[12-15] have aided efforts to engineer activated enzymes. However, if the resultant catalysts have a limited scope, then protein engineering must be tediously repeated to generate activity with additional substrates.[11,16-18] Hence, screening for activity on just one substrate necessarily overlooks mutations that are activating for substrates not included in the screen, and can inadvertently create enzymes with narrow substrate scopes.[17-19] Methods that enable direct assessment of catalyst promiscuity would overcome this recurring barrier and enable the development and application of biocatalysts for organic synthesis, both as single enzymes and in multi-enzyme cascade settings.

An alternative to single-substrate screening is to screen with multiple substrates to obtain information on catalyst promiscuity. Previously, these approaches have gone by various names including fingerprinting, multi-substrate, or multiplexed assays.[20-22] The method used herein is referred to as substrate multiplexed screening (SUMS), which is screening in which substrates are in direct competition (FIG. 4).

We used SUMS as a method to monitor enzyme promiscuity directly during protein engineering. We sought to use indoles as precursors for the synthesis of substituted tryptamines. Tryptamines are desirable synthons of highly bioactive pharmacophores, and their formation is a committed step in biosynthesis of indole alkaloids.[29,30] Applying bioretrosynthetic logic, we chose the L-tryptophan (Trp) decarboxylase from *Ruminococcus gnavus* (RgnTDC).[31] As outlined above, RgnTDC is an exceptional decarboxylase with many Trp analogs but struggles with the highly bioactive 4- and 5-substituted substrates.[30] Such poor activity with non-native substrates is a recurring limitation among biocatalysts; one that is especially limiting in a cascade setting. For the synthesis of these substituted Trp analogs, we selected the β-subunit of tryptophan synthase from the thermophilic archaeon *Pyrococcus furiosus* (PfTrpB), which catalyzes the bimolecular condensation of L-serine (Ser) and indole analogs (FIG. 13). Previously, PfTrpB was evolved for high activity at 75° C. in the absence of its native allosteric partner, TrpA.[32] We chose an engineered PfTrpB variant, 2B9, to generate libraries for analysis by SUMS.[33] Although 2B9 has high activity with a variety of substrate analogs at 75° C., its activity decreases at lower temperatures, which causes a shift in the rate-limiting step.[34] Here, we employ SUMS approaches to rapidly assess the substrate scope of these distinct enzymes and efficiently construct bioactive molecules through a promiscuous, one-pot two-enzyme cascade.

Methods

Screening of RgnTDC Site-Saturation Libraries

Cell pellets were thawed and then resuspended in lysis buffer (50 mM potassium phosphate buffer (pH=8.0), 1 mg/mL Hen Egg White Lysozyme (GoldBio), 0.2 mg/mL DNaseI (GoldBio), 1 mM MgCl$_2$, and 300 μM pyridoxal 5'-phosphate (PLP)). A volume of 600 μL lysis buffer per well was used. After 45 min of shaking at 37° C., the resulting lysate was then spun down at 4000×g to pellet cell debris. Then, 180 μL of the resulting supernatant was added to 20 μL of a substrate mixture in a separate reaction plate. Final substrate concentrations are as follows: W349X 5-substituted-Trp screen: 2 mM each of 5-methoxytryptophan, 5-ethoxytryptophan, 5-methoxy-2-methyltryptophan, 5-carboxamidotryptophan, and 5-acetyltryptophan; W349X single-substrate screen: 2 mM 5-methoxytryptophan; Active-site site-saturation mutagenesis screens: 2 mM each of 2-methyltryptophan, 4-bromotryptophan, 5-methoxytryptophan, and 6-chlorotryptophan; 0.2 mM 7-iodotryptophan and 0.2 mM tryptophan. Reactions were incubated at 37° C. for 4 h, quenched via addition of 150 μL 1:1 acetonitrile: 1 M HCl, and centrifuged at 4000×g for 10 min. 200 μL of the quenched reaction mixture supernatant was filtered into a 96-well plate for UPLC-MS analysis. Data were collected on an Acquity UHPLC with an Acquity QDA MS detector (Waters) using an Intrada Amino Acid column (Imtakt). Tryptamine product m/z ion counts were used to quantify product formation from the tryptophan reaction mixture from corresponding standard curves.

Cascade Synthesis and Isolation of Tryptamines 4-6 mmol (1.4 mmol for 6-chloroindole) of the corresponding indole analog was added to a 1 L Erlenmeyer flask and dissolved in 20 mL MeOH. 12 mmol serine was added, and the resulting solution was diluted up to just under 500 mL with 50 mM potassium phosphate buffer pH=8.0. PLP was added such that the final concentration was 300 μM. Then, a H275E mutant of PfTrpB (SEQ ID NO:3) was added at 0.05% mol catalyst relative to the indole analog. The solution was incubated at 75° C. for 16 h. (H275E was found to be activating at 75° C.). Following UPLC-MS analysis of conversion, the solution was cooled to 37° C., upon which RgnTDC was added at 0.02-0.2% mol catalyst relative to the indole. The solutions were incubated at 37° C. for 24 h. Solutions were then evaporated down to 50-100 mL. To break emulsions, the solutions were acidified with 6 M HCl until pH<1, 100 mL ethyl acetate (EtOAc) was added, and the resulting mixtures were centrifuged at 4000×g for 10 min. These solutions were added to a separatory funnel, the aqueous layer was drained, and the organic layer removed. This was repeated twice more, with 2 mL 6 M HCl added in between extractions. Then, the aqueous layer was alkalized with 6 M NaOH until pH>12. Tryptamine products were then extracted 3× with 150 mL EtOAc, with 2 mL 6 M NaOH added in between extractions to the aqueous layer. Organic layers were pooled, dried with sodium sulfate, filtered, and evaporated down to 5-10 mL. Solutions were transferred to 20 mL scintillation vials, evaporated to near dryness (some tryptamines were observed as liquids at 50° C.), and dried under vacuum overnight. Dried samples were weighed and submitted for 1H and 13C NMR analysis.

Results

Analysis of Underlying Kinetics of Substrate Completion Reactions

The sparse applications of direct-competition screening methods for biocatalysis in the past have acknowledged the significant complexities associated with multiplexed screening. But little information is available about how to design an effective multiplexed screen and how screening outcomes relate to underlying enzymatic properties. Therefore, before we began screening mutant libraries, we investigated many variables, such as substrate choice, relative substrate concentrations, and assay duration, all of which impact the observed product profile. To facilitate connecting the SUMS output to the underlying kinetics, we measured traditional Michaelis-Menten parameters with a variety of substituted Trp analogs using RgnTDC. In general, when multiple substrates are competing for an active site, each substrate acts as a competitive inhibitor for all other substrates.[35] For a unimolecular reaction under initial velocity conditions with equimolar substrates in competition with one another, the product abundances will be exactly proportional to the catalytic efficiencies ($k_{cat}/K_M$) of the individual reactions in isolation (FIG. 5).[35,36] As has been described, this relationship holds true even when the individual substrate concentrations exceed their KMs.[35,36] Correspondingly, comparison of these data to results from multiplexed reactions showed that the ratio of the catalytic efficiencies is deterministic of the product ratios while in the initial velocity regime. As has long been appreciated in enzymology, such multiplexed activity measurements are a true measure of specificity and provide rich kinetic information about enzyme function.[37]

Figure 5:
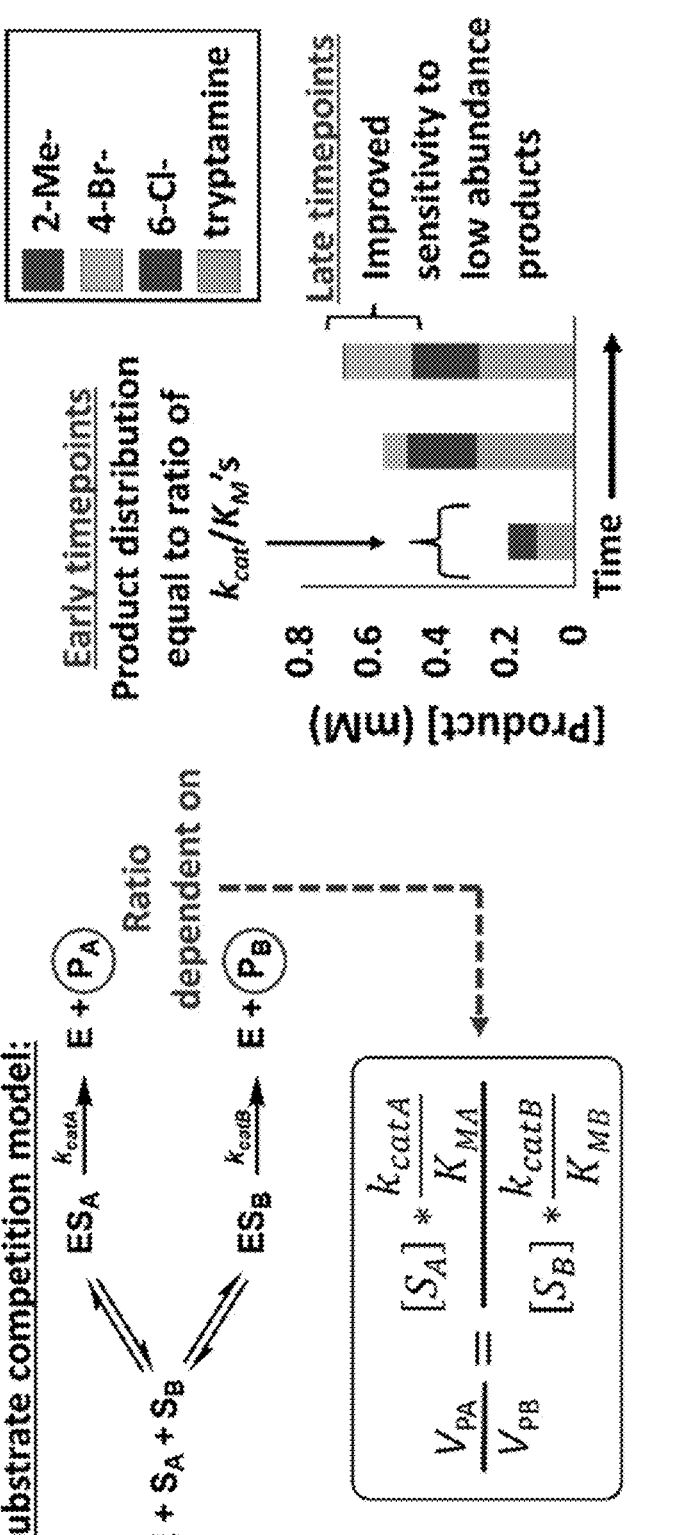
FIG. 5. Substrate competition model with equation describing relative rates of product formation (Left). Comparison between timepoints for a substrate-multiplexed reaction, and the effect of time on the overall product distribution for a four-substrate reaction of RgnTDC with 2-Me-, 4-Br—, 6-Cl—, and Trp (Right). Stacked bars represent concentrations of products (from top to bottom: 2-Me-, 4-Br—, 6-Cl—, and Trp). 2-Me- and 4-Br— were not detected at the earliest timepoint. 2-Me- was not detected at the middle timepoint.

To capture enzyme stability effects and achieve high conversions, effective screening conditions for biocatalysis applications often utilize longer reaction times beyond the initial velocity regime. When reactions are run to higher conversion, the product profile becomes uncoupled from the underlying kinetics and is, instead, a heuristic readout of reactivity that can be tuned to match the goals of biocatalysis research (FIG. 5). We posited that by screening on a mixture with both highly reactive and inert substrates, we could identify catalysts that retain the ability to operate at high turnover numbers as well as identify desirable increases in activity with multiple sluggish substrates.

Assessment of Substrate Scopes

Figure 6:
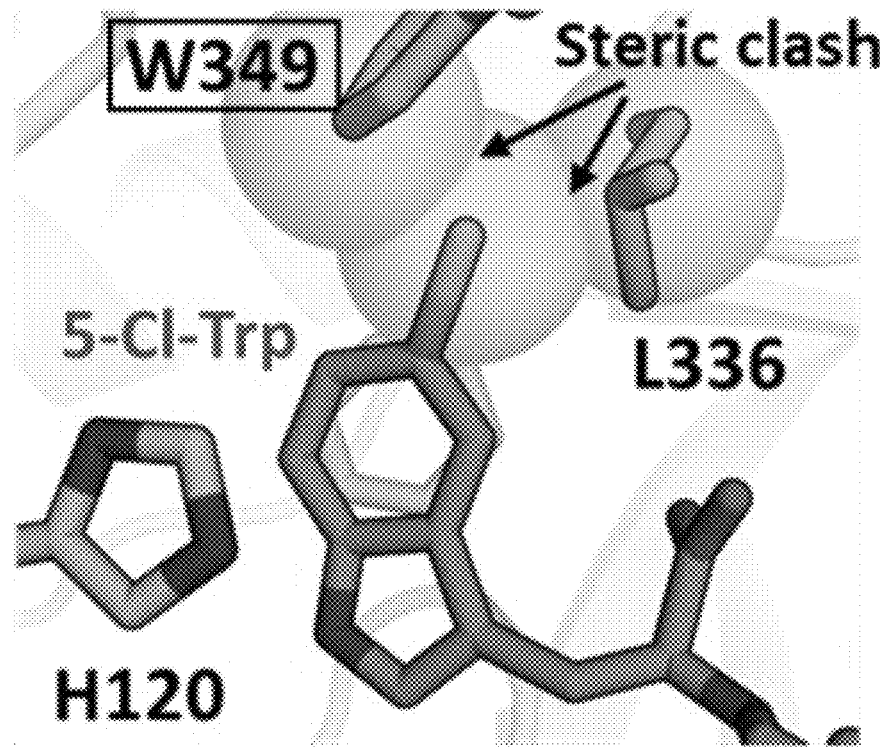
FIG. 6. RgnTDC active-site model of 5-chlorotryptophan, modelled from PDB ID: 4OBV. The potential steric interaction of the 5-chloro-substituent with the W349 and L336 residues is highlighted.
Figure 8:
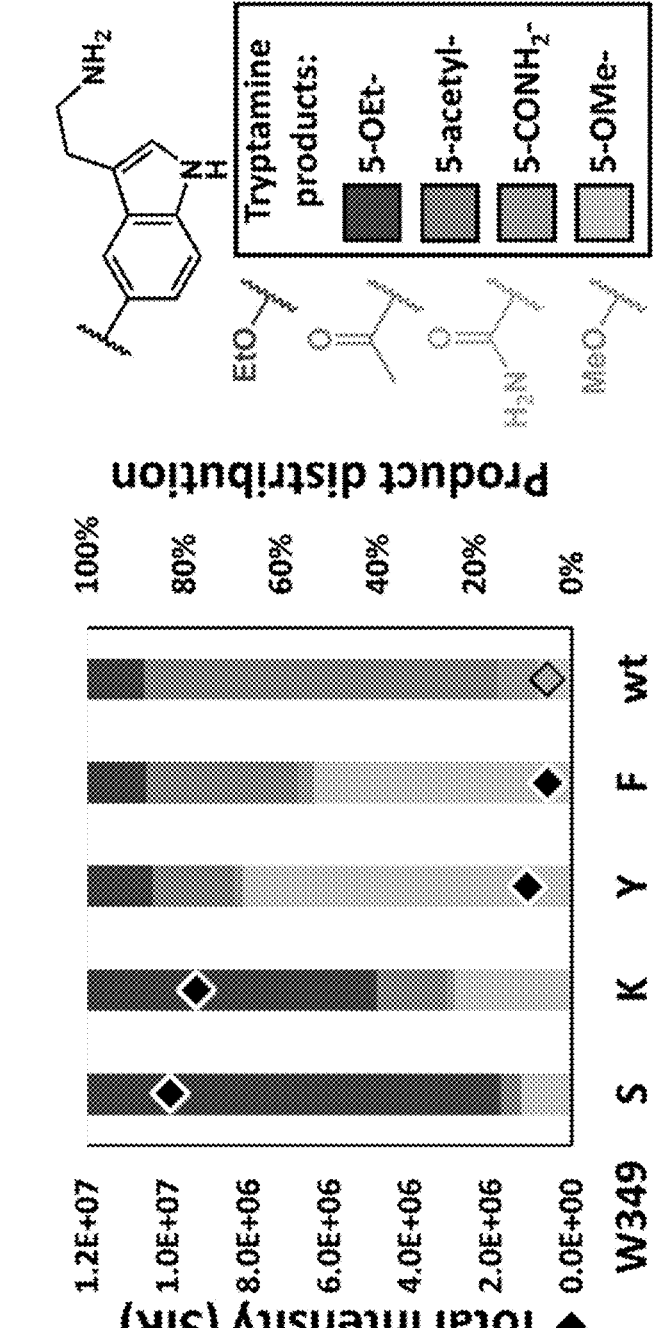
FIG. 8. SUMS results from a W349X library with 5-OEt-, 5-acetyl-, 5-$CONH_2$—, 5-OMe-, and 2-Me, 5-OMe-Trp. Stacked bars indicate relative abundances of each product (from top to bottom: 5-OEt-, 5-acetyl-, 5-$CONH_2$—, and 5-OMe-), and black diamonds indicate total intensity of single ion retention (SIR) for each product's unique m/z. No product was observed from 2-Me, 5-OMe-Trp.

We began engineering for higher RgnTDC activity with 5-substituted Trp analogs, as structure-based modelling suggested W349 forms preclusive steric interactions with these substrates (FIG. 6). We screened a site-saturation mutagenesis (SSM) library, which exchanges the native residue for each other proteinogenic amino acid, at W349 with a mixture of five substrates. For most of the substrates, we found that many mutations increased activity, and that increases in activity varied among the different substrates (FIG. 7). The structurally conservative mutations W349Y and W349F increased activity most with 5-OMe-Trp relative to other substrates, whereas the smaller W349S mutation had the highest activity increase with 5-OEt-Trp and produced the most total product. From this screen, W349K was identified as the most generally improved variant because it produced only slightly less 5-OEt-tryptamine than W349S and formed the most product with all other substrates (FIG. 8).

Figure 9:
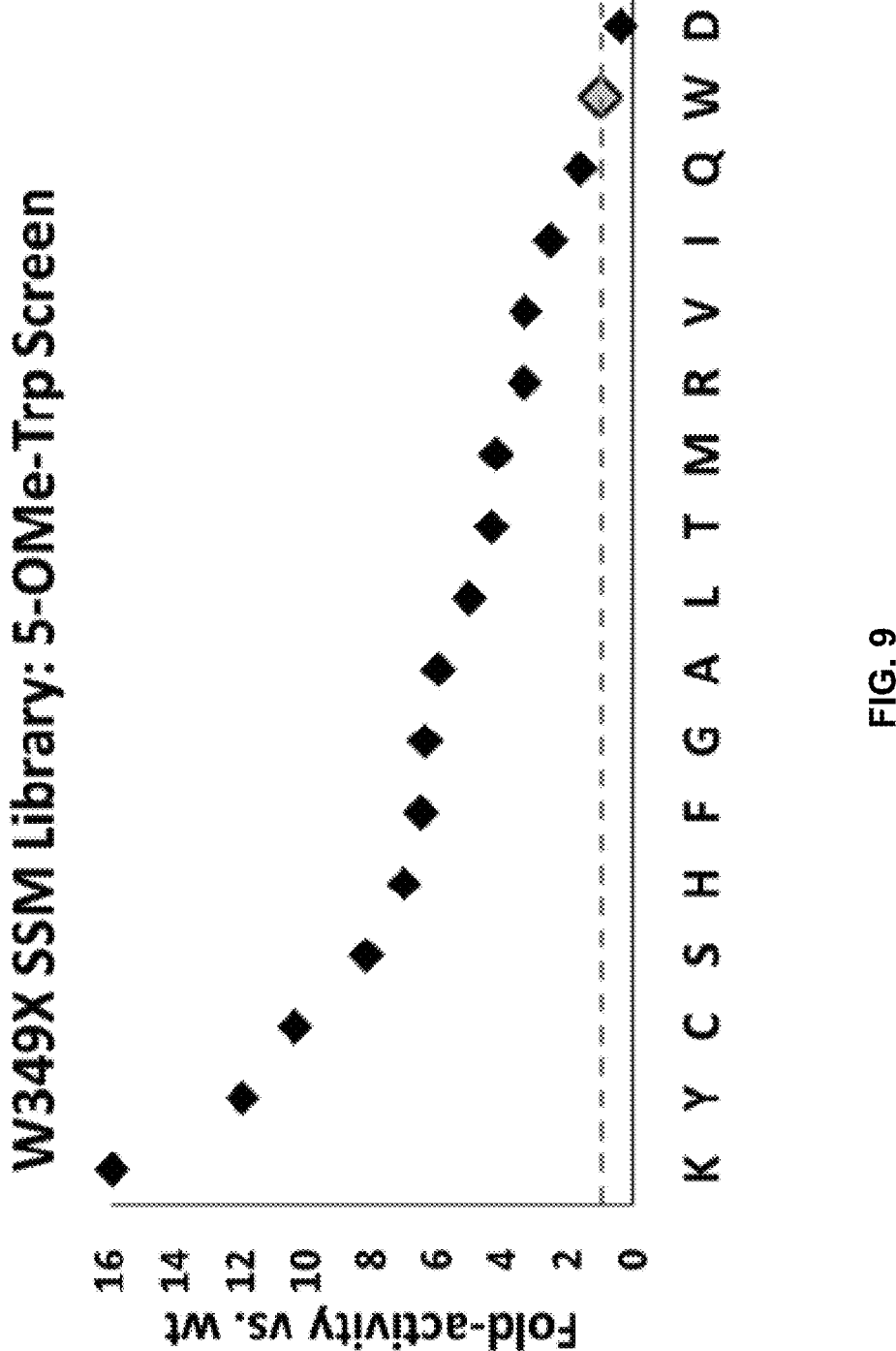
FIG. 9. Fold-activity relative to wild-type from a single-substrate screen of the W349X SSM library with 5-OMe-Trp corresponding to classical protein engineering techniques. Fold-activities were determined relative to wild-type (wt) RgnTDC wells from absorbance at 280 nm. Depicted fold-activities represent averaged fold-activities relative to wt activity for all wells with the above given sequence.

To contrast the promiscuity information from SUMS with traditional approaches, we also performed a single-substrate screen with 5-OMe-Trp on the same W349 library (FIG. 9). As before, we found that almost any mutation increased activity with 5-OMe-Trp. However, there was a poor correlation between activity on 5-OMe-Trp and general activation on 5-substituted Trp analogs. Although W349K was the most activating mutation in both screens, mutations such as W349Y appeared to be highly reactive with 5-OMe-Trp but only poorly tolerate other Trp analogs. These results illustrate how SUMS can immediately identify shifts in both substrate promiscuity and activity with no greater screening effort than would be required for a more traditional, but less informative, approach.

Figure 10A:
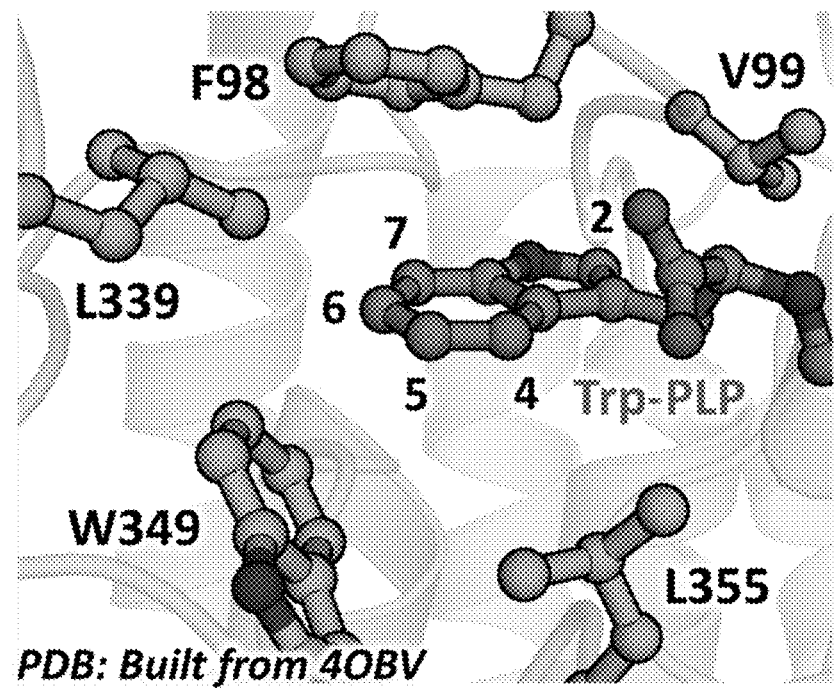
FIGS. 10A-10B. Active-site models of RgnTDC (built from PDB ID: 4OBV)[31] with residues highlighted at which mutations were found that significantly altered promiscuity or improved activity.
Figure 10B:
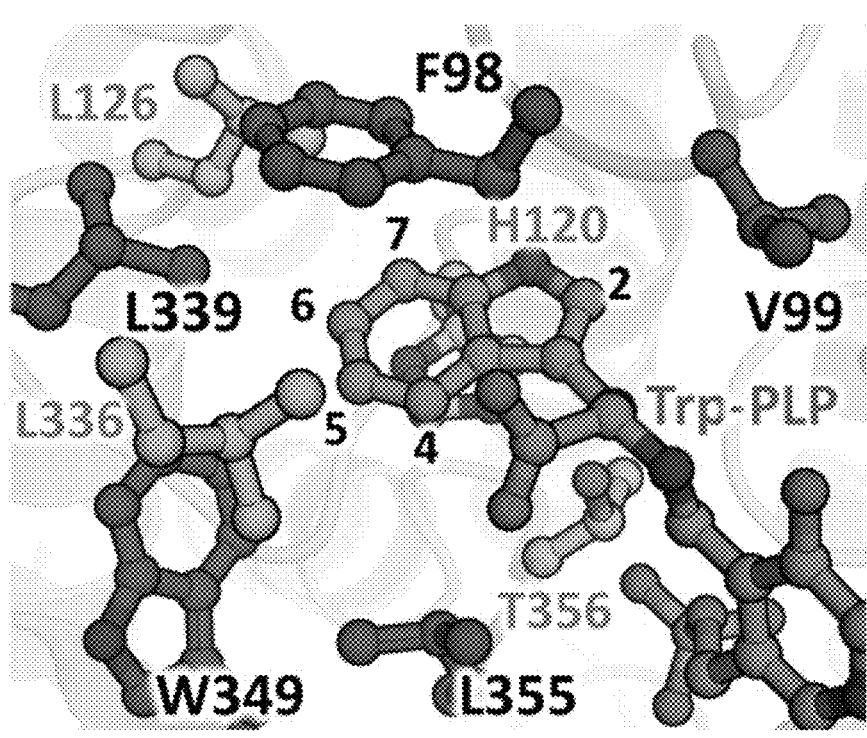

We next screened a mixture of Trp analogs that were each substituted at a different position against a set of nine active-site saturation libraries (FIGS. 10A-10B). From these screens, we found that mutation at two positions, L126 (data not shown) and H120 (FIG. 11C), had only modest impacts on activity and specificity. Mutation at L336 (data not shown) and T356 (data not shown) resulted in many catalytically feeble enzymes, and the variants that retained activity had promiscuity profiles that were similar to wild-type. For the other sites, mutation caused large changes to apparent specificity while retaining significant catalytic activity (11A, 11B, and 11D-11F). For example, we observed >50-fold activity increases with several TDC-Trp analog pairs, such as L355M with 4-Br-Trp (FIGS. 11F and 12A) and F98V with 2-Me-Trp (FIGS. 11A and 12A). Screening with this more diverse substrate mixture also revealed that W349K maintains high activity with non-5-substituted-Trp substrates like 6-Cl-Trp (FIGS. 11E and 12A). Other mutations, such as V99A (FIG. 11B) and L339V (FIG. 11D), were less strongly activating for 2-Me-Trp and 4-Br-Trp but retained broad activity for substituted Trp analogs.

Identified Variants have Improved Single-Substrate Activity

As with single-substrate library screening, validation of hits identified from SUMS is an essential step. While there are many confounding factors that make relative activity in competition distinct from activity on single substrates, there is nevertheless no additional burden in the validation process, which we undertook with the RgnTDC variants. Turnover numbers from these single substrate reactions trended well with multiplexed screening results, with the most active variants showing large increases in single-substrate activity (FIG. 12B). SUMS therefore enabled the parallel engineering of RgnTDC variants for improved activity with multiple challenging substrates.

Characterization of RgnTDC Identified Variants

To understand the kinetic determinants of substrate promiscuity shifts for RgnTDC variants, we measured Michaelis-Menten parameters (FIG. 12C). We found that $k_{cat}/K_M$ values correlated well with observed activities in competition, even though we did not screen under initial velocity conditions. All activated variants showed higher $k_{cat}$ values with their more reactive substrates when compared to wild-type. Notably, there were significant variation in changes to $K_M$ values for activated TDC variants, and such effects were difficult to rationalize for many mutations from structural analysis. For example, we initially hypothesized that mutation at W349 would increase activity by reducing steric clashes in the active site by both decreasing $K_M$ and increasing $k_{cat}$. The W349K mutation, however, accelerates decarboxylation of 5-OMe-Trp exclusively by increasing $k_{cat}$, with minimal impact to $K_M$ values. This result is puzzling, as one might naïvely assume a more flexible residue like Lys pays a higher entropic cost to bind a substrate, manifesting in a higher $K_M$ value than the native Trp residue. The F98V mutation increased $k_{cat}$ with 6-substituted Trp analogs, despite having no apparent steric interactions. Equally perplexing is the case of the L355M mutation. Molecular modeling indicates 4-substituted Trp analogs would form deleterious steric clashes with L355, and rational approaches to engineering would prescribe mutation to smaller sidechains. While the small L355A mutation improved activity on 4-Br-Trp, the conservative L355M mutation was even more activating and had a decreased $K_M$ for both Trp and 4-Br-Trp compared to wild-type RgnTDC. We highlight these unexpected findings as an advantage of interrogating active-site libraries with SUMS, as such mutations could have been missed entirely by screening with the wrong pairings of substrate and mutational site.

Cascade Catalysis is Empowered by Enzymes with Complementary Specificity

Figure 14A:
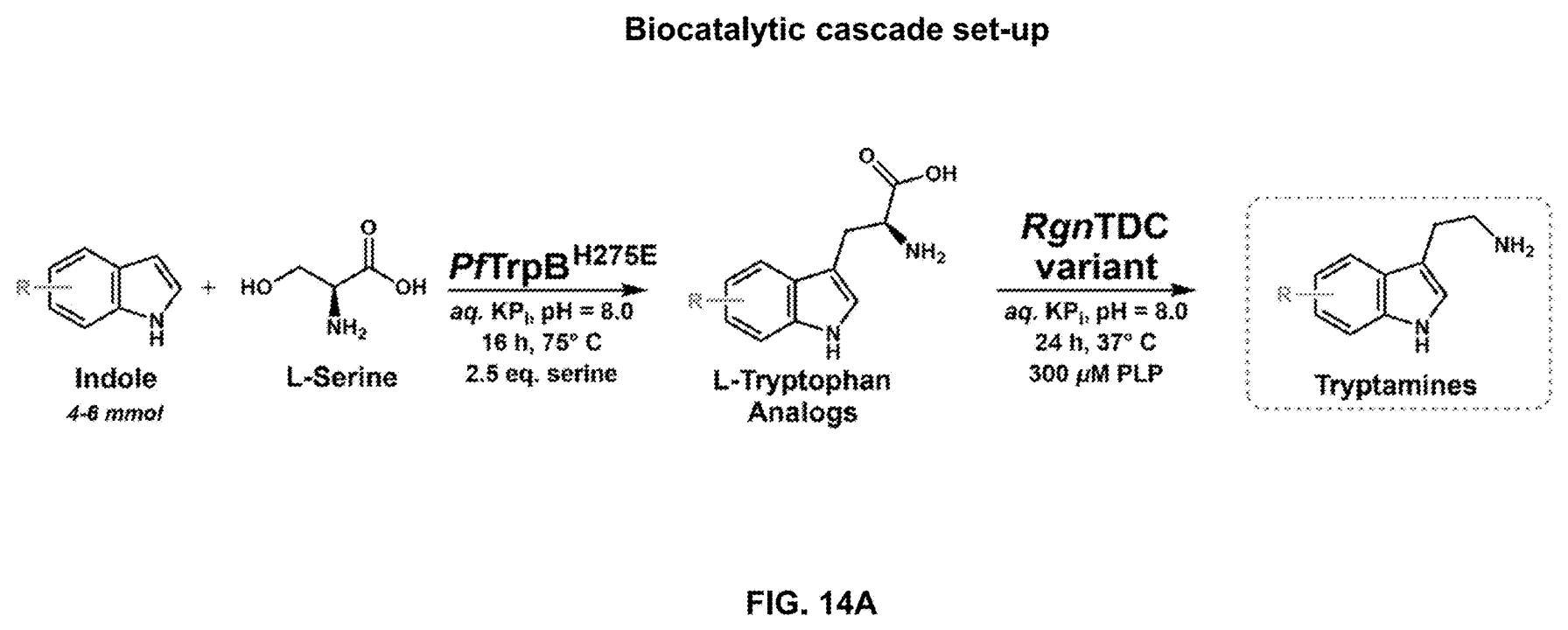
Figure 14B:
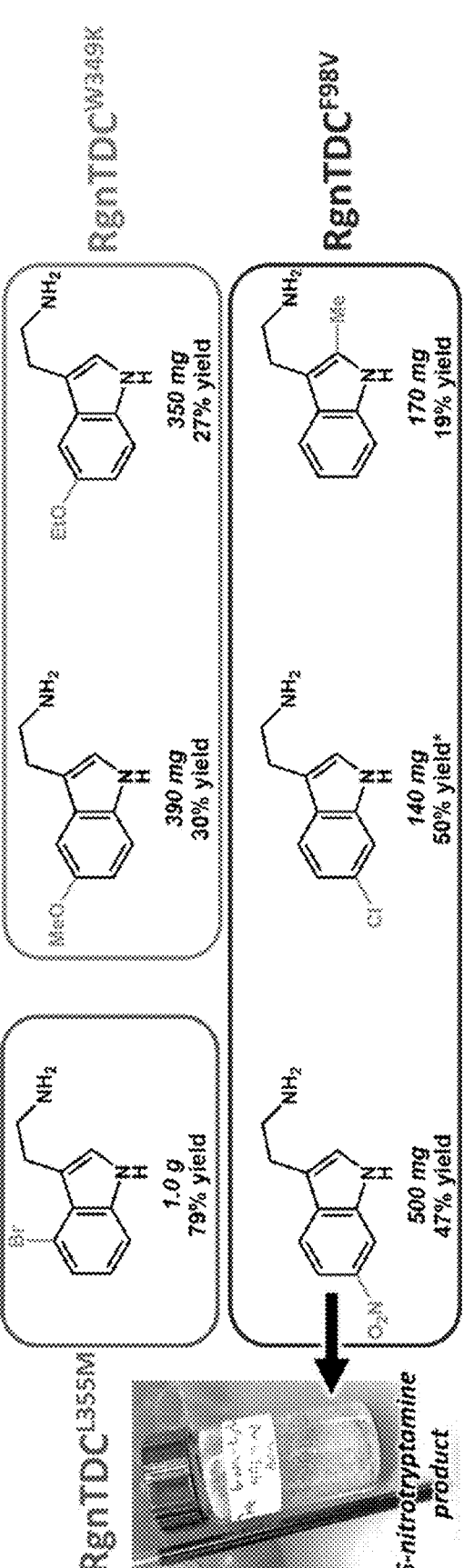

Last, we sought to demonstrate the practical utility of the enzymes produced herein. Many enzymes are more synthetically useful when employed in cascades, which can overcome thermodynamic limitations and obviate the need for purification of intermediates.[4] To this end, we performed mmol syntheses of diverse tryptamine analogs, including 5-OMe-tryptamine and 5-OEt-tryptamine, known serotonin receptor agonists,[43] and 2-Me-tryptamine and 4-Br-tryptamine, which were particularly challenging products for the original parent cascade.[30] Each product was made in a telescoped biocatalytic cascade with the H275E PfTrpB variant and an engineered RgnTDC variant and isolated with improved yields compared to reactions with the parent enzymes (FIG. 14A-14B). Although no TDC variant was identified with improved activity for all Trp analogs, the direct assessment of substrate scope provided by SUMS allowed us to select an optimal catalyst for each tryptamine product.

Discussion

A central limitation to the synthetic application of many enzymes is their unpredictable and too-often poor substrate scope when compared to organic methodology.[44] This limitation is particularly difficult to overcome for biosynthetic cascades due to the requirement of overlapping substrate scopes for all enzymes of the cascade. Traditional protein engineering excels at increasing activity on a single substrate but provides no selective pressure to improve activity across a broad substrate scope. Here, used SUMS to immediately inform the activity and promiscuity of an enzyme from a single experiment. Previous approaches have been used to guide engineering where an enzyme with the ability to act on complex mixtures of substrates was the desired outcome. Here, we provided catalysts with improved activity in single-substrate reactions. We further detailed unique advantages when screening for broad activity on multiple substrates, facilitating discovery of desirable biocatalysts. We then leveraged these catalysts for an improved biosynthetic cascade route for the synthesis of desirable, bioactive analogs of tryptophan and tryptamine.

Because activity in competition is not identical to activity on isolated substrates, the information herein is more than the sum of its parts. We emphasize that the application of SUMS here does not focus on absolute specificity, since screening does not take place under initial velocity conditions or with identical substrate concentrations. Instead, we use SUMS to identify changes in the ratios of the products for all mutations screened, including those that appear neutral with respect to one or more substrates in the reaction. This sensitivity to changes in product distribution allowed to identify distal mutations that influence the active site by altering substrate promiscuity, even if the overall effect is deactivating. A shift in promiscuity for the PfTrpB H275R variant led us to screen other mutations at this site, revealing the generally activated H275E variant. These examples highlights the engineering advantage of screening for both activity and promiscuity. By screening site-saturation mutagenesis libraries at sites that engage in cooperative effects with the active site, regardless of their change in activity, an activating mutation may be found.

Conclusion

We show here the successful engineering of enzymes with improved activity on multiple compounds simultaneously. These examples establishes the utility for engineering of biocatalytic cascades. By directly assessing enzyme activity on substrates in competition, we provide uniquely rich promiscuity information that has hitherto been underutilized during engineering campaigns.

References

1. Goodwin, N. C., Morrison, J. P., Fuerst, D. E. & Hadi, T. Biocatalysis in Medicinal Chemistry: Challenges to Access and Drivers for Adoption. *ACS Med. Chem. Lett.* 10, 1363-1366 (2019).
2. Sattler, J. H. et al. Redox Self-Sufficient Biocatalyst Network for the Amination of Primary Alcohols. *Angew. Chemie* 51, 9156-9159 (2012).
3. Staudt, S. et al. Direct Oxidation of Cycloalkanes to Cycloalkanones with Oxygen in Water. *Angew. Chemie* 52, 2359-2363 (2013).
4. Schrittwieser, J. H., Velikogne, S., Hall, M. & Kroutil, W. Artificial Biocatalytic Linear Cascades for Preparation of Organic Molecules. *Chemical Reviews* vol. 118 270-348 (2018).
5. Savile, C. K. et al. Biocatalytic Asymmetric Synthesis of Chiral Amines from Ketones Applied to Sitagliptin Manufacture. *Science* (80-.). 329, 305-310 (2010).
6. Huffman, M. A. et al. Design of an in vitro biocatalytic cascade for the manufacture of islatravir. *Science* (80-.). 368, 1255-1259 (2020).

7. Truppo, M. D. Biocatalysis in the Pharmaceutical Industry: The Need for Speed. *ACS Med. Chem. Lett.* 8, 476-480 (2017).

8. Sandström, A. G., Wikmark, Y., Engström, K., Nyhlén, J. & Bäckvall, J. E. Combinatorial reshaping of the *Candida antarctica* lipase A substrate pocket for enantioselectivity using an extremely condensed library. *PNAS* 109, 78-83 (2012).

9. Fox, R. J. et al. Improving catalytic function by ProSAR-driven enzyme evolution. *Nat. Biotechnol.* 25, 338-344 (2007).

10. Amin, N. et al. Construction of stabilized proteins by combinatorial consensus mutagenesis. *Protein Eng. Des. Sel.* 17, 787-793 (2004).

11. Reetz, M. T., Bocola, M., Carballeira, J. D., Zha, D. & Vogel, A. Expanding the range of substrate acceptance of enzymes: Combinatorial active-site saturation test. *Angew. Chemie—Int. Ed.* 44, 4192-4196 (2005).

12. Diefenbach, X. W. et al. Enabling Biocatalysis by High-Throughput Protein Engineering Using Droplet Microfluidics Coupled to Mass Spectrometry. *ACS Omega* 3, 1498-1508 (2018).

13. McLaren, D. G. et al. High-Throughput Mass Spectrometry for Hit Identification: Current Landscape and Future Perspectives. *SLAS Discov.* 26, 168-191 (2021).

14. Obexer, R. et al. Emergence of a catalytic tetrad during evolution of a highly active artificial aldolase. (2016) doi:10.1038/NCHEM.2596.

15. Ye, L., Yang, C. & Yu, H. From molecular engineering to process engineering: development of high-throughput screening methods in enzyme directed evolution. *Appl. Microbiol. Biotechnol.* 2017 1022 102, 559-567 (2017).

16. Andorfer, M. C., Park, H. J., Vergara-Coll, J. & Lewis, J. C. Directed evolution of RebH for catalyst-controlled halogenation of indole C—H bonds. *Chem. Sci.* 7, 3720-3729 (2016).

17. Romney, D. K., Murciano-Calles, J., Wehrmüller, J. E. & Arnold, F. H. Unlocking Reactivity of TrpB: A General Biocatalytic Platform for Synthesis of Tryptophan Analogues. *J. Am. Chem. Soc.* 139, 10769-10776 (2017).

18. Romney, D. K., Sarai, N. S. & Arnold, F. H. Nitroalkanes as Versatile Nucleophiles for Enzymatic Synthesis of Noncanonical Amino Acids. *ACS Catal.* 9, acscatal.9b02089 (2019).

19. Andorfer, M. C. et al. Understanding Flavin-Dependent Halogenase Reactivity via Substrate Activity Profiling. *ACS Catal.* 7, 1897-1904 (2017).

20. Goddard, J., Reymond, J. & Uni, V. Enzyme Activity Fingerprinting with Substrate Cocktails. *JAGS Commun.* 11116-11117 (2004).

21. Kim, H. et al. A multi-substrate screening approach for the identification of a broadly applicable Diels-Alder catalyst. *Nat. Commun.* 1-6 (2019) doi:10.1038/s41467-019-08374-z.

22. Stanisic, A., Husken, A. & Kries, H. HAMA: a multiplexed LC-MS/MS assay for specificity profiling of adenylate-forming enzymes. *Chem. Sci.* 10, 10395-10399 (2019).

23. Kuo, Y. M., Henry, R. A. & Andrews, A. J. Measuring specificity in multi-substrate/product systems as a tool to investigate selectivity in vivo. *Biochim. Biophys. Acta—Proteins Proteomics* 1864, 70-76 (2016).

24. Joiner, C. M., Levine, Z. G., Aonbangkhen, C., Woo, C. M. & Walker, S. Aspartate Residues Far from the Active Site Drive O-GlcNAc Transferase Substrate Selection. *J. Am. Chem. Soc.* 141, 12974-12978 (2019).

25. Desai, B. J. & Gonzalez, R. L. Multiplexed genomic encoding of non-canonical amino acids for labeling large complexes. *Nat. Chem. Biol.* 16, 1129-1135 (2020).

26. Weeks, A. M. & Wells, J. A. Engineering peptide ligase specificity by proteomic identification of ligation sites. *Nat. Chem. Biol.* 14, 50-57 (2018).

27. Wang, L., Xie, J. & Schultz, P. G. Expanding the genetic code. *Annu. Rev. Biophys. Biomol. Struct.* 35, 225-249 (2006).

28. Knorrscheidt, A. et al. Simultaneous screening of multiple substrates with an unspecific peroxygenase enabled modified alkane and alkene oxyfunctionalisations. *Catal. Sci. Technol.* 6058-6064 (2021) doi:10.1039/d0cy02457k.

29. Fricke, J., Blei, F. & Hoffmeister, D. Enzymatic Synthesis of Psilocybin. *Angew. Chemie—Int. Ed.* 56, 12352-12355 (2017).

30. McDonald, A. D., Perkins, L. J. & Buller, A. R. Facile in Vitro Biocatalytic Production of Diverse Tryptamines. *ChemBioChem* 20, 1939-1944 (2019).

31. Williams, B. B. et al. Discovery and characterization of gut microbiota decarboxylases that can produce the neurotransmitter tryptamine. *Cell Host Microbe* 16, 495-503 (2014).

32. Buller, A. R. et al. Directed evolution of the tryptophan synthase β-subunit for stand-alone function recapitulates allosteric activation. *Proc. Natl. Acad. Sci.* 112, 14599-14604 (2015).

33. Herger, M. et al. Synthesis of β-Branched Tryptophan Analogues Using an Engineered Subunit of Tryptophan Synthase. *J. Am. Chem. Soc.* 138, 8388-8391 (2016).

34. Buller, A. R. et al. Directed evolution mimics allosteric activation by stepwise tuning of the conformational ensemble. *J. Am. Chem. Soc.* 140, 7256-7266 (2018).

35. Cornish-Bowden, A. Enzyme Specificity: Its Meaning in the General Case. *J. theor. Biol.* 108, 451-457 (1984).

36. Fersht, A. *Structure and Mechanism in Protein Science: A Guide to Enzyme Catalysis and Protein Folding.* (W. H. Freeman and Company, 1999).

37. Buller, A. R., Van Roye, P., Murciano-Calles, J. & Arnold, F. H. Tryptophan Synthase Uses an Atypical Mechanism To Achieve Substrate Specificity. *Biochemistry* 55, 7043-7046 (2016).

38. Heilmann, H. D. On the mechanism of action of *Escherichia coli* tryptophan synthase Steady-state investigations. *BBA—Enzymol.* (1978) doi:10.1016/0005-2744(78)90092-X.

39. Wrenbeck, E. E., Azouz, L. R. & Whitehead, T. A. Single-mutation fitness landscapes for an enzyme on multiple substrates reveal specificity is globally encoded. *Nat. Commun.* 8, 1-10 (2017).

40. Watkins-Dulaney, E., Straathof, S. & Arnold, F. Tryptophan Synthase: Biocatalyst Extraordinaire. *ChemBioChem* vol. 22 5-16 (2021).

41. Matthews, B. W. Structural and genetic analysis of protein stability. *Annual Review of Biochemistry* vol. 62 139-160 (1993).

42. Bloom, J. D., Labthavikul, S. T., Otey, C. R. & Arnold, F. H. Protein stability promotes evolvability. *Proc. Natl. Acad. Sci. U.S.A.* 103, 5869-5874 (2006).

43. Glennon, R. A. Higher-End Serotonin Receptors: 5-HT5, 5-HT6, and 5-HT7. *J. Med. Chem.* 46, 2795-2812 (2003).

44. Reetz, M. T. What are the Limitations of Enzymes in Synthetic Organic Chemistry? *Chem. Rec.* 16, 2449-2459 (2016).

EXEMPLARY EMBODIMENTS OF THE INVENTION

1. An unnatural, mutant protein comprising an amino acid sequence at least 90% identical to SEQ ID NO:1, wherein:

the amino acid sequence comprises one or more of:

a residue other than phenylalanine at a position corresponding to position 98 of SEQ ID NO:1;

a residue other than valine at a position corresponding to position 99 of SEQ ID NO:1;

a residue other than histidine at a position corresponding to position 120 of SEQ ID NO:1;

a residue other than leucine at a position corresponding to position 126 of SEQ ID NO:1;

a residue other than leucine at a position corresponding to position 339 of SEQ ID NO:1;

a residue other than tryptophan at a position corresponding to position 349 of SEQ ID NO:1; and a residue other than leucine at a position corresponding to position 355 of SEQ ID NO:1.

2. The protein of exemplary embodiment 1, wherein the amino acid sequence comprises one or more of:

a residue other than phenylalanine at a position corresponding to position 98 of SEQ ID NO:1;

a residue other than valine at a position corresponding to position 99 of SEQ ID NO:1;

a residue other than leucine at a position corresponding to position 339 of SEQ ID NO:1;

a residue other than tryptophan at a position corresponding to position 349 of SEQ ID NO:1; and a residue other than leucine at a position corresponding to position 355 of SEQ ID NO:1.

3. The protein of any one of exemplary embodiments 1-2, wherein the amino acid sequence comprises one or more of:

methionine or valine at a position corresponding to position 98 of SEQ ID NO:1;

alanine at a position corresponding to position 99 of SEQ ID NO:1;

valine at a position corresponding to position 339 of SEQ ID NO:1;

lysine, phenylalanine, serine, or tryptophan at a position corresponding to position 349 of SEQ ID NO:1; and alanine or methionine at a position corresponding to position 355 of SEQ ID NO:1.

4. The protein of any one of exemplary embodiments 1-3, wherein the protein exhibits activity in decarboxylating a tryptophan analog substrate.

5. The protein of any one of exemplary embodiments 1-4, wherein the protein exhibits activity in decarboxylating a substituted tryptophan substrate comprising a substituent at one or more of a 2 position, a 4 position, a 5 position, a 6 position, or a 7 position on the substituted tryptophan.

6. The protein of any one of exemplary embodiments 1-5, wherein the protein exhibits an increased activity with respect to a protein comprising an amino acid sequence 100% identical to SEQ ID NO:1, wherein the increased activity comprises increased activity in decarboxylating a substituted tryptophan substrate.

7. The protein of any one of exemplary embodiments 1-5, wherein the protein exhibits an increased activity with respect to a protein comprising an amino acid sequence 100% identical to SEQ ID NO:1, wherein the increased activity comprises any one or more of:

increased activity in decarboxylating a substituted tryptophan substrate comprising a substituent at any one or more of a 2 position, a 4 position, a 5 position, a 6 position, or a 7 position on the substituted tryptophan;

increased activity in decarboxylating a first substrate relative to a second substrate, wherein the first substrate is not the second substrate, wherein the first substrate is selected from the group consisting of any one or more of 2-substituted tryptophan, 4-substituted tryptophan, 5-substituted tryptophan, 6-substituted tryptophan, and 7-substituted tryptophan, and wherein the second substrate is selected from the group consisting of any one or more of unsubstituted tryptophan, 2-substituted tryptophan, 4-substituted tryptophan, 5-substituted tryptophan, 6-substituted tryptophan, and 7-substituted tryptophan; and increased combined activity in decarboxylating any two or more different substrates, wherein the two more different substrates are selected from the group consisting of unsubstituted tryptophan, one or more 2-substituted tryptophans, one or more 4-substituted tryptophans, one or more 5-substituted tryptophans, one or more 6-substituted tryptophans, and one or more 7-substituted tryptophans.

8. The protein of any one of exemplary embodiments 1-7, wherein the amino acid sequence comprises methionine at a position corresponding to position 98 of SEQ ID NO:1.

9. The protein of any one of exemplary embodiments 1-7, wherein the amino acid sequence comprises valine at a position corresponding to position 98 of SEQ ID NO:1.

10. The protein of any one of exemplary embodiments 1-7, wherein the amino acid sequence comprises alanine at a position corresponding to position 99 of SEQ ID NO:1.

11. The protein of any one of exemplary embodiments 1-7, wherein the amino acid sequence comprises valine at a position corresponding to position 339 of SEQ ID NO:1.

12. The protein of any one of exemplary embodiments 1-7, wherein the amino acid sequence comprises lysine at a position corresponding to position 349 of SEQ ID NO:1.

13. The protein of any one of exemplary embodiments 1-7, wherein the amino acid sequence comprises phenylalanine at a position corresponding to position 349 of SEQ ID NO:1.

14. The protein of any one of exemplary embodiments 1-7, wherein the amino acid sequence comprises serine at a position corresponding to position 349 of SEQ ID NO:1.

15. The protein of any one of exemplary embodiments 1-7, wherein the amino acid sequence comprises tryptophan at a position corresponding to position 349 of SEQ ID NO:1.

16. The protein of any one of exemplary embodiments 1-7, wherein the amino acid sequence comprises alanine at a position corresponding to position 355 of SEQ ID NO:1.

17. The protein of any one of exemplary embodiments 1-7, wherein the amino acid sequence comprises methionine at a position corresponding to position 355 of SEQ ID NO:1.

18. The protein of any one of exemplary embodiments 1-17, wherein protein comprising an amino acid sequence at least 95% identical to SEQ ID NO:1

19. The protein of any one of exemplary embodiments 1-17, wherein protein comprising an amino acid sequence at least 99% identical to SEQ ID NO:1

20. A method of generating a product, the method comprising contacting a substrate with the protein of any one of exemplary embodiments 1-19 to thereby generate the product, wherein the substrate comprises a tryptophan analog.

21. The method of exemplary embodiment 20, wherein the substrate comprises substituted tryptophan and the product comprises substituted tryptamine.

22. The method of exemplary embodiment 21, wherein the substituted tryptophan comprises a substituent at any one or more of a 2 position, a 4 position, a 5 position, a 6 position, or a 7 position on the substituted tryptophan.

23. The method of any one of exemplary embodiments 20-22, further comprising generating the substrate, wherein generating the substrate comprises contacting an upstream substrate with a tryptophan synthase to thereby generate the substrate, wherein the upstream substrate comprises an indole analog.

24. The method of exemplary embodiment 23, wherein the upstream substrate comprises substituted indole.

25. The method of exemplary embodiment 24, wherein the substituted indole comprises a substituent at any one or more of a 2 position, a 4 position, a 5 position, a 6 position, or a 7 position on the substituted indole.

26. The method of any one of exemplary embodiments 23-25, wherein the contacting the upstream substrate with the tryptophan synthase to thereby generate the substrate and the contacting the substrate with the protein to thereby generate the product are performed intracellularly.

27. The method of any one of exemplary embodiments 23-25, wherein the contacting the upstream substrate with the tryptophan synthase to thereby generate the substrate and the contacting the substrate with the protein to thereby generate the product are performed in vitro.

28. The method of any one of exemplary embodiments 20-25, wherein the contacting the substrate with the protein to thereby generate the product is performed intracellularly.

29. The method of any one of exemplary embodiments 20-25, wherein the contacting the substrate with the protein to thereby generate the product is performed in vitro.

---

What is claimed is:

1. An unnatural, mutant protein comprising an amino acid sequence at least 90% identical to SEQ ID NO:1, wherein: the amino acid sequence comprises one or more of:

a residue other than phenylalanine at a position corresponding to position 98 of SEQ ID NO:1;

a residue other than valine at a position corresponding to position 99 of SEQ ID NO: 1;

a residue other than histidine at a position corresponding to position 120 of SEQ ID NO:1;

a residue other than leucine at a position corresponding to position 126 of SEQ ID NO:1;

a residue other than leucine at a position corresponding to position 339 of SEQ ID NO:1;

a residue other than tryptophan at a position corresponding to position 349 of SEQ ID NO:1; and a residue other than leucine at a position corresponding to position 355 of SEQ ID NO: 1; and the protein exhibits activity in decarboxylating a tryptophan analog substrate.

2. The protein of claim 1, wherein the amino acid sequence comprises one or more of:

a residue other than phenylalanine at a position corresponding to position 98 of SEQ ID NO:1;

a residue other than valine at a position corresponding to position 99 of SEQ ID NO: 1;

a residue other than leucine at a position corresponding to position 339 of SEQ ID NO:1;

a residue other than tryptophan at a position corresponding to position 349 of SEQ ID NO:1; and a residue other than leucine at a position corresponding to position 355 of SEQ ID NO:1.

3. The protein of claim 1, wherein the amino acid sequence comprises one or more of:

methionine or valine at a position corresponding to position 98 of SEQ ID NO: 1;

alanine at a position corresponding to position 99 of SEQ ID NO:1;

valine at a position corresponding to position 339 of SEQ ID NO:1;

lysine, phenylalanine, serine, or tyrosine at a position corresponding to position 349 of SEQ ID NO:1; and alanine or methionine at a position corresponding to position 355 of SEQ ID NO: 1.

4. The protein of claim 3, wherein the protein comprises an amino acid sequence at least 95% identical to SEQ ID NO:1.

5. The protein of claim 1, wherein the amino acid sequence comprises a residue other than tryptophan at a position corresponding to position 349 of SEQ ID NO: 1.

6. The protein of claim 1, wherein the amino acid sequence comprises lysine, phenylalanine, serine, or tyrosine at a position corresponding to position 349 of SEQ ID NO:1.

7. The protein of claim 1, wherein the protein exhibits activity in decarboxylating a substituted tryptophan substrate comprising a substituent at one or more of a 2 position, a 4 position, a 5 position, a 6 position, and a 7 position on the substituted tryptophan.

8. The protein of claim 1, wherein the protein exhibits an increased activity with respect to a protein comprising an amino acid sequence 100% identical to SEQ ID NO:1, wherein the increased activity comprises increased activity in decarboxylating a substituted tryptophan substrate.

9. The protein of claim 1, wherein the protein exhibits an increased activity with respect to a protein comprising an amino acid sequence 100% identical to SEQ ID NO:1, wherein the increased activity comprises any one or more of:

increased activity in decarboxylating a substituted tryptophan substrate comprising a substituent at any one or more of a 2 position, a 4 position, a 5 position, a 6 position, and a 7 position on the substituted tryptophan;

increased activity in decarboxylating a first substrate relative to a second substrate, wherein the first substrate is not the second substrate, wherein the first substrate is selected from the group consisting of any one or more of 2-substituted tryptophan, 4-substituted tryptophan, 5-substituted tryptophan, 6-substituted tryptophan, and 7-substituted tryptophan, and wherein the second substrate is selected from the group consisting of any one or more of unsubstituted tryptophan, 2-substituted tryptophan, 4-substituted tryptophan, 5-substituted tryptophan, 6-substituted tryptophan, and 7-substituted tryptophan; and increased combined activity in decarboxylating any two or more different substrates, wherein the two more different substrates are selected from the group consisting of unsubstituted tryptophan, one or more 2-substituted tryptophans, one or more 4-substituted tryptophans, one or more 5-substituted tryptophans, one or more 6-substituted tryptophans, and one or more 7-substituted tryptophans.

10. The protein of claim 1, wherein the protein comprises an amino acid sequence at least 95% identical to SEQ ID NO:1.

11. The protein of claim 1, wherein the protein comprises an amino acid sequence at least 99% identical to SEQ ID NO:1.

12. A method of generating a product, the method comprising contacting a substrate with the protein of claim 1 to thereby generate the product, wherein the substrate comprises a tryptophan analog.

13. The method of claim 12, wherein the substrate comprises substituted tryptophan and the product comprises substituted tryptamine.

14. The method of claim 13, wherein the substituted tryptophan comprises a substituent at any one or more of a 2 position, a 4 position, a 5 position, a 6 position, and a 7 position on the substituted tryptophan.

15. The method of claim 12, further comprising generating the substrate, wherein generating the substrate comprises contacting an upstream substrate with a tryptophan synthase to thereby generate the substrate, wherein the upstream substrate comprises an indole analog.

16. The method of claim 15, wherein the upstream substrate comprises substituted indole.

17. The method of claim 16, wherein the substituted indole comprises a substituent at any one or more of a 2 position, a 4 position, a 5 position, a 6 position, and a 7 position on the substituted indole.

18. The method of claim 15, wherein the contacting the upstream substrate with the tryptophan synthase to thereby generate the substrate and the contacting the substrate with the protein to thereby generate the product are performed intracellularly.

19. The method of claim 15, wherein the contacting the upstream substrate with the tryptophan synthase to thereby generate the substrate and the contacting the substrate with the protein to thereby generate the product are performed in vitro.

20. The method of claim 12, wherein the contacting the substrate with the protein to thereby generate the product is performed intracellularly.

21. The method of claim 12, wherein the contacting the substrate with the protein to thereby generate the product is performed in vitro.

* * * * *